(12) United States Patent
Raillard et al.

(10) Patent No.: US 8,580,850 B2
(45) Date of Patent: Nov. 12, 2013

(54) ANHYDROUS AND HEMIHYDRATE CRYSTALLINE FORMS OF AN (R)-BACLOFEN PRODRUG, METHODS OF SYNTHESIS AND METHODS OF USE

(75) Inventors: Stephen P. Raillard, Mountain View, CA (US); Suresh K. Manthati, Sunnyvale, CA (US); Sudhir Joshi, Visp (CH)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 13/572,367

(22) Filed: Aug. 10, 2012

(65) Prior Publication Data

US 2013/0041026 A1 Feb. 14, 2013

Related U.S. Application Data

(60) Provisional application No. 61/508,286, filed on Aug. 11, 2011.

(51) Int. Cl.
| | | |
|---|---|---|
| C07C 271/22 | (2006.01) |
| C07C 269/08 | (2006.01) |
| A61P 19/00 | (2006.01) |
| A61P 11/00 | (2006.01) |
| A61P 29/00 | (2006.01) |
| A61P 25/30 | (2006.01) |
| A61P 1/04 | (2006.01) |
| A61K 31/27 | (2006.01) |

(52) U.S. Cl.
USPC .............................................. 514/487; 560/30

(58) Field of Classification Search
USPC .............................................. 514/487; 560/30
See application file for complete search history.

(56) References Cited

U.S. PATENT DOCUMENTS

| | | | |
|---|---|---|---|
| 4,126,684 | A | 11/1978 | Robson et al. |
| 5,006,560 | A | 4/1991 | Kreutner et al. |
| 5,719,185 | A | 2/1998 | Bountra et al. |
| 6,117,908 | A | 9/2000 | Andrews et al. |
| 7,109,239 | B2 | 9/2006 | Gallop et al. |
| 7,227,028 | B2 | 6/2007 | Gallop et al. |
| 2002/0151529 | A1 | 10/2002 | Cundy et al. |
| 2003/0133951 | A1 | 7/2003 | Coe et al. |
| 2003/0171303 | A1 | 9/2003 | Gallop et al. |
| 2003/0176398 | A1 | 9/2003 | Gallop et al. |
| 2004/0006132 | A1 | 1/2004 | Gallop et al. |
| 2004/0014940 | A1 | 1/2004 | Raillard et al. |
| 2004/0138305 | A1 | 7/2004 | Dooley et al. |
| 2004/0180959 | A1 | 9/2004 | Dooley et al. |
| 2007/0032500 | A1 | 2/2007 | Sun et al. |
| 2007/0082939 | A1 | 4/2007 | Lippa et al. |

FOREIGN PATENT DOCUMENTS

| | | |
|---|---|---|
| EP | 1178034 | 2/2002 |
| WO | 91/08740 | 6/1991 |
| WO | 01/08675 | 2/2001 |
| WO | 01/26638 | 4/2001 |
| WO | 01/90052 | 11/2001 |
| WO | 02/096404 | 12/2002 |
| WO | 2005/019163 | 3/2005 |
| WO | 2008/086492 | 7/2008 |
| WO | 2009/096985 | 8/2009 |

OTHER PUBLICATIONS

Addolorato et al., "Baclofen efficacy in reducing alcohol craving and intake: a preliminary double-blind randomized controlled study," *Alcohol & Alcoholism* (2002) 37(5):504-508.
Ahmadi-Abhari et al., "Baclofen versus clonidine in the treatment of opiates withdrawal, side-effects aspect: a double-blind randomized controlled trial," *J Clin Pharm Ther.* (2001) 26:67-71.
Aley et al., "Vincristine hyperalgesia in the rat: a model of painful vincristine neuropathy in humans," *Neurosci.* (1996), 73(1): 259-265.
Anghinah et al., "Effect of baclofen on pain in diabetic neuropathy," *Muscle & Nerve* (1994) 17(8):958-9.
Argoff, "Pharmacologic management of chronic pain," *JAOA Supp. 3* (2002), 102(9): S21-S26.
Assadi et al., "Baclofen for maintenance treatment of opioid dependence: a randomized double-blind placebo-controlled clinical trial," *BMC Psychiatry* (2003), 3(16) (10 pages).
Authier et al., "Assessment of allodynia and hyperalgesia after cisplatin administration to rats," *Neurosci. Lett.* (2000), 291: 73-76.
Backonja et al., "Gabapentin dosing for neuropathic pain: evidence from randomaized, placebo-controlled clinical trials," *Clin. Ther.* (2003), 25: 81-104.
Balerio et al., "Baclofen analgesia: involvement of the GABAergic system," *Pharm. Res.* (2002) 46(3):281-286.
Baron, "Mechanisms of disease: neuropathic pain—a clinical perspective," *Nat. Clin. Pract. Neurol.* (2006), 2(2): 95-106.
Becker et al., "Intrathecal baclofen alleviates autonomic dysfunction in severe brain injury," *J Clin. Neurosci.* (2000) 7(4):316-319.
Beggs et al., "Neuropathic pain: symptoms, models and mechanisms," *Drug Dev. Res.* (2006), 67: 289-301.
Bennett et al., "A peripheral mononeuropathy in rat that produces disorders of pain sensation like those seen in man," *Pain* (1988), 33: 87-107.
Blackshaw et al., "Inhibition of transient LES relaxations and reflux in ferrets by GABA receptor agonists," *Am. J. Physiol.* (1999), 277: G867-G874.
Bowery, "$GABA_B$ receptors and their significance in mammalian pharmacology," *Trends Pharmacol. Sci.* (1989) 10:401-407.
Brebner et al., "A potential role for $GABA_B$ agonists in the treatment of psychostimulant addiction," *Alcohol & Alcoholism* (2002) 37(5):478-484.
Caira, "Crystalline Polymorphism of Organic Compounds," *Topics in Current Chemistry* (1998) 198, pp. 163-208.

(Continued)

*Primary Examiner* — San-Ming Hui
*Assistant Examiner* — Kathrien Cruz
(74) *Attorney, Agent, or Firm* — Dorsey and Whitney LLP

(57) ABSTRACT

Crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate, pharmaceutical compositions comprising such compounds, methods of making and methods of using the same are disclosed.

20 Claims, 4 Drawing Sheets

(56) References Cited

OTHER PUBLICATIONS

Castell et al., "XP19986 decreases reflux and is well tolerated in GERD patients," *Am J. Gastroenterology* (2006) 101(suppl 2)(52), S59 and poster presentation at American College of Gastroenterology 2006 Annual Meeting, Oct. 20-25, 2006, Las Vegas, NV.

Castell et al., "R-baclofen prodrug XP19986 decreases reflux episodes and is well tolerated in GERD patients," *Gastroenterology* (2007) suppl. A, 486 and poster presentation at Digestive Disease Week Meeting, May 19-24, 2007, Washington D.C.

Cavaletti et al., "Experimental peripheral neuropathy induced in adult rats by repeated intraperitoneal administration of Taxol," *Exp. Neurol.* (1995), 133: 64-72.

Chacur et al., "A new model of sciatic inflammatory neuritis (SIN): induction of unilateral and bilateral mechanical allodynia following acute unilateral peri-sciatic immune activation in rats," *Pain* (2001), 94: 231-244.

Chai et al., "Influence of aminooxyacetic acid, a γ-aminobutyrate transaminase inhibitor, on hereditary spastic defect in the mouse," *Proc. Soc. Exptl. Biol. Med.* (1962), 109: 491-495.

Chan et al., "Action of anti-tussive drugs on the emetic reflex of *Suncus murinus* (house musk shrew)," *Eur. J. Pharmacol.* (2007) 559:196-201.

Chaplan et al., "Quantitative assessment of tactile allodynia in the rat paw," *J. Neurosci. Meth.* (1994), 53: 55-63.

Ciccaglione et al., "Effect of acute and chronic administration of the $GABA_B$ agonist baclofen on 24 hour pH metry and symptoms in control subjects and in patients with gastro-oesophageal reflux disease," *Gut* (2003) 52:464-470.

Cousins et al., "$GABA_B$ receptor agonists for the treatment of drug addiction: a review of recent findings," *Drug and Alcohol Depend.* (2002) 65:209-220.

Crofford et al., "Pregabalin for the treatment of fibromyalgia syndrome," *Arth. Rheum.* (2005), 52(4): 1264-1273.

Dapas et al., "Baclofen for the treatment of acute low-back syndrome—a double-blind comparison with placebo," *Spine* (1985) 10(4):345-349.

De Leo et al., "Characterization of a neuropathic pain model: sciatic cryoneurolysis in the rat," *Pain* (1994), 56: 9-16.

De Vry et al., "Pharmacological characterization of the chronic pain construction injury model of neuropathic pain," *Eur. J. Pharmacol.* (2004), 491: 137-148.

Decosterd et al., "Spared nerve injury: an animal model of persistent peripheral neuropathic pain," *Pain* (2000), 87: 149-158.

Dicpinigaitis et al., "Antitussive effect of the GABA-agonist baclofen," *Chest* (1997) 111:996-999.

Dicpinigaitis et al., "Inhibition of capsaicin-induced cough by the γ-am inobutyric acid agonist baclofen," *J Clin Pharmacol* (1998) 38:364-367.

Dirig et al., "Intrathecal baclofen and muscimol, but not midazolam, are antinociceptive using the rat-formalin model," *JPET* (1995), 275(1): 219-227.

Dunham et al., "A note on a simple apparatus for detecting neurological deficit in rats and mice," *J. Am. Pharm. Assoc.* (1957), 46(3): 208-09.

Eaton, "Common animal models for spasticity and pain," *J. Rehab. Res. Dev.* (2003), 40(4): 41S-54S.

Endo et al., "The ferret: a cytotoxic drug-induced emesis model," *Biogenic Amines* (2004), 18(3-6): 419-434.

Fattore et al., "Baclofen antagonizes intravenous self-administration of nicotine in mice and rats," *Alcohol & Alcoholism* (2002), 37(5): 495-498.

Flannery et al., "Baclofen for alcohol dependence: a preliminary open-label study," *Alcohol Clin. Exp. Res.* (2004) 28(10):1517-1523.

Fox et al., "Critical evaluation of the streptozotocin model of painful diabetic neuropathy in the rat," *Pain* (1999), 81: 307-316.

Fox et al., "Comparative activity of the anti-convulsants oxcarbazepine, carbamazepine, lamotrigine and gabapentin in a model of neuropathic pain in the rat and guinea-pig," *Pain* (2003), 105: 355-362.

Freitag, "Preventative treatment for migraine and tension-type headaches: do drugs having effects on muscle spasm and tone have a role?," *CNS Drugs* (2003) 17(6), 373-381.

Freynhagen et al., "Efficacy of pregabalin in neuropathic pain evaluated in a 12-week, randomised, double-blind, milticentre, placebo-controlled trial of flexible- and fixed-dose regimens," *Pain* (2005), 115: 254-263.

Fromm et al., "Baclofen in the treatment of trigeminal neuralgia: double-blind study and long-term follow-up," *Ann. Neurol.* (1984) 15:240-244.

Fromm et al., "Role of inhibitory mechanisms in trigeminal neuralgia," *Neurology* (1981) 31:683-687.

Gatscher et al., "Combined intrathecal baclofen and morphine infusion for the treatment of spasticity related pain and central deafferentiation pain," *Acta Neurochir* (2001) 79(Suppl):75-76.

Gidal et al., "New and emerging treatment options for neuropathic pain," *Am. J. Manag. Care* (2006), 12: S269-S278.

Gruenthal et al., "Gabapentin for the treatment of spasticity in patients with spinal cord injury," *Spinal Cord* (1997), 35: 686-689.

Guay, "Pregabalin in neuropathic pain: a more "pharmaceutically elegant" gabapentin?," *Am. J. Geriat.r Pharmacother.* (2005), 3(4): 274-287.

Haney et al., "Effects of baclofen on cocaine self-administration: opioid- and nonopioid-dependent volunteers," *Neuropsychopharmacology* (2006) 31:1814-21.

Hao et al., "Allodynia-like effects in rat after ischaemic spinal cord injury photochemically induced by laser irradiation," *Pain* (1991), 45: 175-185.

Hefferan et al., "Development of baclofen tolerance in a rat model of chronic spasticity and rigidity," *Neurosci. Lett.* (2006), 403: 195-200.

Heinzerling et al., "Randomized, placebo-controlled trial of baclofen and gabapentin for the treatment of methamphetamine dependence," *Drug Alcohol Depend.* (2006) 85:177-184.

Hering-Hanit et al., "Baclofen in cluster headache," *Headache* (2000) 40:48-51.

Hering-Hanit, "Baclofen for prevention of migraine," *Cephalalgia* (1999) 19:589-591.

Herman et al., "Intrathecal baclofen suppresses central pain in patients with spinal lesions," A pilot study, *Clin J Pain* (1992) 8:338-345.

Herzberg et al., "Peripheral nerve exposure to HIV viral envelope protein gp120 induces neuropathic pain and spinal gliosis," *J. Neuroimmunol.* (2001), 116: 29-39.

Hornby et al., "Central mechanisms of lower esophageal sphincter control," *Gastroenterol. Clin. N. Am.* (2002) 31(4 Suppl):S11-S20.

Hwang et al., "The effect of spinal GABA receptor agonists on tactile allodynia in a surgically-induced neuropathic pain model in the rat," *Pain* (1997) 70:15-22.

Irwin, "Comprehensive observational assessment: la. A systematic, quantitative procedure for assessing the behavioral and physiologic state of the mouse," *Psychopharmacologia* (1968), 13: 222-257.

Jensen et al., "The clinical picture of neuropathic pain," *Eur. J. Pharmacol.* (2001), 429: 1-11.

Joseph et al., "Novel mechanism of enhanced nociception in a model of AIDS therapy-induced painful neuropathy in the rat," *Pain* (2004), 107: 147-158.

Kakinohana et al., "Development of GABA-sensitive spasticity and rigidity in rats after transient spinal cord ischemia: a qualitative and quantitative electrophysiological and histopathological study," *Neurosci.* (2006), 141: 1569-1583.

Katz, "Management of spasticity," *Am. J. Phys. Med. Rehab.* (1988) 67(3), 108-16.

Kehl et al., "A new animal model for assessing mechanisms and management of muscle hyperalgesia," *Pain* (2000), 85: 333-343.

Kim and Chung, "An experimental model for peripheral neuropathy produced by segmental spinal nerve ligation in the rat," *Pain* (1992), 50: 355-363.

Krach, "Pharmacotherapy of spasticity: oral medications and intrathecal baclofen," *J. Child Neurol.* (2001) 16:31-36.

Kupers et al., "Photochemically-induced ischemia of the rat sciatic nerve produces a dose-dependent and highly reproducible mechanical, heat and cold allodynia, and signs of spontaneous pain," *Pain* (1998), 76: 45-59.

(56) References Cited

OTHER PUBLICATIONS

Lal et al., "Arbaclofen placarbil, a novel R-baclofen prodrug: improved absorption, distribution, metabolism, and elimination properties compared with R-baclofen," *J Pharmacology Experimental Therapeutics* (2009) 330:911-921.

Lehmann et al., "Activation of the $GABA_B$ receptor inhibits transient lower esophageal sphincter relaxation in dogs," *Gastroenterology* (1999), 117: 1147-1154.

Lewis et al., "Animal models of cough: literature review and presentation of a novel cigarette smoke-enhanced cough model in the guinea-pig," *Pulm. Pharm. Ther.* (2007), 20: 325-333.

Li et al., "Effects of baclofen on spinal reflexes and persistent inward currents in motoneurons of chronic spinal rats with spasticity," *J. Neurophysiol.* (2004), 92: 2694-2703.

Lidums et al., "Control of transient lower esophageal sphincter relaxations and reflux by the $GABA_B$ agonist baclofen in normal subjects," *Gastroenterology* (2000) 118:7-13.

Ligresti et al., "New potent and selective inhibitors of anandamide reuptake with antispastic activity in a mouse model of multiple sclerosis," *Br. J. Pharm.* (2006), 147: 83-91.

Liu et al., "Pica—a model of nausea? Species differences in response to cisplatin," *Physiol. Behav.* (2005), 85: 271-277.

Lombard et al., "Deafferentiation hypersensitivity in the rat after dorsal rhizotomy: a possible animal model of chronic pain," *Pain* (1979), 6: 163-174.

Loscher and Schmidt, "Which animal models should be used in the search for now antiepileptic drugs? A proposal based on experimental and clinical considerations," *Epilepsy Res.* (1988), 2: 145-181.

Maccioni et al., "Baclofen-induced reduction of alcohol reinforcement in alcohol-preferring rats," *Alcohol* (2005), 36: 161-168.

Malik et al., "Differential effects of dexamethasone, ondansetron and tachykinin $NK_1$ receptor agonist (GR205171) on cisplatin-induced changes in behaviour, food intake, pica and gastric function in rats," *Eur. J. Pharmacol.* (2007), 555: 164-173.

Markou et al., "Role of γ-aminobutyric acid (GABA) and metabotropic glutamate receptors in nicotine reinforcement: potential pharmacotherapies for smoking cessation," *Ann N.Y. Acad. Sci.* (2004) 1025:491-503.

Meleger et al., "Neck and back pain: musculoskeletal disorders," *Neurol. Clin.* (2007) 25:419-438.

Milligan et al., "Thermal hyperalgesia and mechanical allodynia produced by intrathecal administration of the human immunodeficiency virus-1 (HIV-1) envelope glycoprotein gp120," *Brain Res.* (2000), 861: 105-116.

Misgeld et al., "A physiological role for $GABA_B$ receptors and the effects of baclofen in the mammalian central nervous system," *Prog. Neurobiol.* (1995) 46:423-462.

Mosconi and Kruger, "Fixed diameter polyethylene cuffs applied to the rat sciatic nerve induce a painful neuropathy: ultrastructural morphometric analysis of axonal alterations," *Pain* (1996), 64: 37-57.

Patel et al., "The effects of $GABA_B$ agonists and gabapentin on mechanical hyperalgesia in models of neuropathic and inflammatory pain in the rat," *Pain* (2001) 90(3):217-26.

Polomano et al., "A painful peripheral neuropathy in the rat produced by the chemotherapeutic drug, paclitaxel," *Pain* (2001), 94: 293-304.

Priebe et al., "Effectiveness of gabapentin on controlling spasticity: a quantitative study," *Spinal Cord* (1997), 35: 171-175.

Raphael et al., "Long-term experience with implanted intrathecal drug administration systems for failed back syndrome and chronic mechanical low back pain," *BMC Musculoskeletal Disorders* (2002) 3(17): 1-8.

Reis et al., "Baclofen, an agonist at peripheral $GABA_B$ receptors, induces antinociception via activation of TEA-sensitive potassium channels," *Br J Pharmacol* (2006) 149(6):733-739.

Rhodes et al., "Nausea, vomiting, and retching: complex problems in palliative care," *CA Cancer J. Clin.* (2001), 51: 232-248.

Ringel et al., "Glossopharyngeal neuralgia: successful treatment with baclofen," *Ann Neurol* (1987) 21(5):514-515.

Sanger et al., "Classification and definition of disorders causing hypertonia in childhood," *Pediatrics* (2003), 111: e89-e97.

Seltzer et al., "A novel behavioral model of neuropathic pain disorders produced in rats by partial sciatic nerve injury," *Pain* (1990), 43: 205-218.

Shimizu et al., "$GABA_B$ receptors do not mediate inhibitory actions of gabapentin on the spinal reflux in rats," *J. Pharmacol. Sci.* (2004), 96: 444-449.

Sindrup and Jensen, "Efficacy of pharmacological treatments of neuropathic pain: an update and effect related to mechanism of drug action," *Pain* (1999), 83: 389-400.

Slart et al., "An animal model of pain produced by systemic administration of an immumotherapeutic anti-ganglioside antibody," *Pain* (1997), 69: 119-125.

Slonimski et al., "Intrathecal baclofen in pain management," *Reg Anesth Pain Med* (2004) 29(3) :269-276.

Smith et al., "Increased sensitivity to the antinociceptive activity of (+/−)-baclofen in an animal model of chronic neuropathic, but not chronic inflammatory hyperalgesia," *Neuropharmacology* (1994) 33(9):1103-1108.

Spano et al., "The $GABA_B$ receptor agonist baclofen prevents heroin-induced reinstatement of heroin-seeking behavior in rats," *Neuropharmacol.* (2007), 52: 1555-1562.

Stakeberg and Lehmann, "Influence of different intragastric stimuli on triggering of transient lower oesophageal sphincter relaxation in the dog," *Neurogastroenterol. Mot.* (1999), 11: 125-132.

Steeves et al., "Guidelines for the conduct of clinical trials for spinal cord injury (SCI) as developed by the ICCP panel: clinical trial outcome measures," *Spinal Cord* (2007), 45: 206-221.

Suzuki et al., "Effect of a selective $GABA_B$ receptor agonist baclofen on the μ-opioid receptor agonist-induced antinociceptive, emetic and rewarding effects," *Neuropharmacology* (2005) 49:1121-1131.

Taylor-Gjevre et al., "Anti-glutamic acid decarboxylase antibodies in a patient with systemic lupus erythematosus and fibromyalgia symptoms," *Lupus* (2005) 14:486-488.

Tuszynski et al., "Guidelines for the conduct of clinical trials for spinal cord injury as developed by the ICCP panel: clinical trial inclusion/exclusion criteria and ethics," *Spinal Cord* (2007), 45: 222-231.

Van Herwaadren et al., "The effect of baclofen on gastro-oesophageal reflux, lower oesophageal sphincter function and reflux symptoms in patients with reflux disease," *Aliment. Pharmacol. Ther.* (2002) 16:1655-1662.

Van Hilten et al., "Intrathecal baclofen for the treatment of dystonia in patients with reflex sympathetic dystrophy," *N Engl J Med* (2000) 343:625-630.

Vela et al., "Baclofen decreases acid and non-acid post-prandial gastro-oesophageal reflux measured by combined multichannel intraluminal impedance and Ph," *Aliment Pharmacol Ther* (2003) 17:243-251.

Von Heijne et al., "Effects of intrathecal morphine, baclofen, clonidine and R-PIA on the acute allodynia-like behaviours after spinal cord ischaemia in rats," *Eur. J. Pain* (2001), 5: 1-10.

Wall et al., "Autotomy following peripheral nerve lesions: experimental anaesthesia dolorosa," *Pain* (1979), 7: 103-113.

Wright and Rang, "The spastic mouse and the search for an animal model of spasticity in human beings," *Clin. Orthop. Relat. Res.* (1990), 253: 12-19.

Zhang et al., "Establishment of a spastic cerebral palsy model in rats," *Chin. J. Clin. Rehab.* (2006), 10(38): 150-151. English language abstract only.

Zhang et al., "Control of transient lower oesophageal sphincter relaxations and reflux by the $GABA_B$ agonist baclofen in patients with gastro-oesophageal reflux disease," *Gut* (2002) 50:19-24.

Zuniga et al., "Intrathecal baclofen: a useful agent in the treatment of well-established complex regional pain syndrome," *Reg Anesth Pain Med* (2002) 27:90-93.

PCT International Search Report and Written Opinion dated Nov. 19, 2012, PCT Appl. No. PCT/US2012/050379, 12 pages.

ANHYDROUS AND HEMIHYDRATE CRYSTALLINE FORMS OF AN (R)-BACLOFEN PRODRUG, METHODS OF SYNTHESIS AND METHODS OF USE

This application claims the benefit under 35 U.S.C. §119 (e), of U.S. Provisional Patent Application No. 61/508,286 filed Aug. 11, 2011, which is incorporated herein by reference in its entirety.

FIELD

Crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate, pharmaceutical compositions comprising such compounds, methods of making such compounds and methods of using such compounds are disclosed.

BACKGROUND

In general, crystalline forms of drugs are utilized in dosage forms rather than amorphous forms of drugs, in part, because of their superior stability. For example, in many situations, an amorphous drug converts to a crystalline drug form upon storage. Because amorphous and crystalline forms of a drug typically have different physical/chemical properties, potencies and/or bioavailabilities, such interconversion is undesirable for safety reasons in pharmaceutical administration.

Polymorphs are crystals of the same molecule which have different physical properties because the crystal lattice contains a different arrangement of molecules. For example, certain polymorphs can include different hydration states that incorporate water into the crystalline structure without chemical alteration of the molecule itself. In that regard, certain compounds can exist in anhydrous and hydrated forms, where the hydrated forms can include, for example, hydrates, dihydrates, trihydrates, and the like, or partial hydrates such as hemihydrates. The different physical properties exhibited by polymorphs can affect important pharmaceutical parameters such as storage, stability, compressibility, density (important in formulation and product manufacturing) and dissolution rates (important in determining bioavailability). Stability differences may result from changes in chemical reactivity (e.g., differential hydrolysis or oxidation, such that a dosage form discolors more rapidly when the dosage form contains one polymorph rather than another polymorph), mechanical changes (e.g., tablets crumble on storage as a kinetically favored crystalline form converts to a thermodynamically more stable crystalline form) or both (e.g., tablets of one polymorph are more susceptible to breakdown at high humidity). Solubility differences between polymorphs may, in extreme situations, result in transitions to crystalline forms that lack potency and/or are toxic. In addition, the physical properties of a particular crystalline form may be important in pharmaceutical processing. For example, one particular crystalline form may form solvates more readily or may be more difficult to filter and wash free of impurities than other forms (e.g., particle shape and size distribution might be different between one crystalline form relative to other forms).

Regulatory agencies such as the United States Food and Drug Administration closely regulate the polymorphic content of the active component of a drug in solid dosage forms. In general, regulatory agencies require batch-by-batch monitoring for polymorphic drugs if anything other than the pure, thermodynamically preferred polymorph is marketed. Accordingly, medical and commercial reasons favor synthesizing and marketing the most thermodynamically stable polymorph of a crystalline drug substance in solid drugs, which is substantially free of other, less favored polymorphs.

(3R)-4-{[(1S)-2-methyl-1-(2-methylpropanoyloxy)propoxy]carbonylamino}-3-(4-chlorophenyl)butanoic acid, (1),

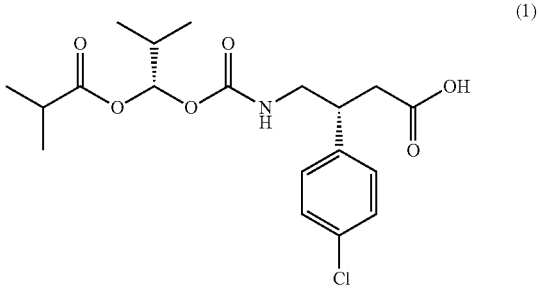 [SMILES: CC(C)C(=O)O[C@@H](OC(=O)NC[C@H](CC(=O)O)c1ccc(Cl)cc1)C(C)C]

(1)

is a prodrug of the GABA$_B$ agonist, (R)-baclofen. (3R)-4-{[(1S)-2-methyl-1-(2-methylpropanoyloxy)propoxy]carbonylamino}-3-(4-chlorophenyl)butanoic acid, (1) exhibits high bioavailability as R-baclofen when dosed either orally or directly into the colon of a mammal (see, for example, Gallop et al., U.S. Pat. Nos. 7,109,239 and 7,227,028).

SUMMARY

Crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate are disclosed.

In a first aspect, crystalline (3R)-4-{[(1S)-2-methyl-1-(2-methylpropanoyloxy)propoxy]carbonylamino}-3-(4-chlorophenyl)butanoic acid hemihydrate, which exhibits characteristic scattering angles (2θ) at least at 4.04°±0.2°, 6.47°±0.2°, 15.68°±0.2°, 18.91°±0.2° and 22.42°±0.2° in an X-ray powder diffractogram measured using Cu—K$_\alpha$ radiation, is provided.

In a second aspect, pharmaceutical compositions are provided comprising crystalline (3R)-4-{[(1S)-2-methyl-1-(2-methylpropanoyloxy)propoxy]carbonylamino}-3-(4-chlorophenyl)butanoic acid hemihydrate, which exhibits characteristic scattering angles (2θ) at least at 4.04°±0.2°, 6.47°±0.2°, 15.68°±0.2°, 18.91°±0.2° and 22.42°±0.2° in an X-ray powder diffractogram measured using Cu—K$_\alpha$ radiation and a pharmaceutically acceptable vehicle.

In a third aspect, methods of preparing crystalline (3R)-4-{[(1S)-2-methyl-1-(2-methylpropanoyloxy)propoxy]carbonylamino}-3-(4-chlorophenyl)butanoic acid hemihydrate, which exhibits characteristic scattering angles (2θ) at least at 4.04°±0.2°, 6.47°±0.2°, 15.68°±0.2°, 18.91°±0.2° and 22.42°±0.2° in an X-ray powder diffractogram measured using Cu—K$_\alpha$ radiation are provided, by steps comprising providing a solution comprising 1-((2,5-dioxopyrrolidin-1-yl-oxycarbonyloxy)-2-methylpropyl-2-methylpropanoate prepared as a racemic mixture, (R)-baclofen, water and a solvent; and adjusting the temperature of the solution or suspension to provide crystalline (3R)-4-{[(1S)-2-methyl-1-(2-methylpropanoyloxy)propoxy]carbonylamino}-3-(4-chlorophenyl)butanoic acid hemihydrate.

In a fourth aspect, methods of treating a disease or disorder in a patient are provided comprising administering to a patient in need of such treatment a therapeutically effective amount of a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate, wherein the disease or disorder is selected from spasticity, gastroesophageal reflux disease, emesis, cough, substance addiction and abuse, neuropathic pain and musculoskeletal pain.

In a fifth aspect, kits are provided comprising a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating a disease or disorder chosen from selected from spasticity, gastroesophageal reflux disease, emesis, cough, substance addiction and abuse, neuropathic pain and musculoskeletal pain.

In a sixth aspect, crystalline (3R)-4-{[(1S)-2-methyl-1-(2-methylpropanoyloxy)propoxy]carbonylamino}-3-(4-chlorophenyl)butanoic acid anhydrate, which exhibits characteristic scattering angles (2θ) at least at 4.33°±0.2°, 4.76°±0.2°, 11.06°±0.2° and 11.61°±0.2° in an X-ray powder diffractogram measured using Cu—K$_\alpha$ radiation, is provided.

In a seventh aspect, pharmaceutical compositions are provided comprising crystalline (3R)-4-{[(1S)-2-methyl-1-(2-methylpropanoyloxy)propoxy]carbonylamino}-3-(4-chlorophenyl)butanoic acid anhydrate, which exhibits characteristic scattering angles (2θ) at least at 4.33°±0.2°, 4.76°±0.2°, 11.06°±0.2° and 11.61°±0.2° in an X-ray powder diffractogram measured using Cu—K$_\alpha$ radiation and a pharmaceutically acceptable vehicle.

In a eighth aspect, methods of preparing crystalline (3R)-4-{[(1S)-2-methyl-1-(2-methylpropanoyloxy)propoxy]carbonylamino}-3-(4-chlorophenyl)butanoic acid anhydrate, which exhibits characteristic scattering angles (2θ) at least at 4.33°±0.2°, 4.76°±0.2°, 11.06°±0.2° and 11.61°±0.2° in an X-ray powder diffractogram measured using Cu—K$_\alpha$ radiation are provided, by steps comprising providing a solution comprising 1-((2,5-dioxopyrrolidin-1-yl-oxycarbonyloxy)-2-methylpropyl-2-methylpropanoate prepared as a racemic mixture, (R)-baclofen, water and a solvent; adjusting the temperature of the solution or suspension to provide crystalline (3R)-4-{[(1S)-2-methyl-1-(2-methylpropanoyloxy)propoxy]carbonylamino}-3-(4-chlorophenyl)butanoic acid hemihydrate and (3R)-4-{[(1R)-2-methyl-1-(2-methylpropanoyloxy)propoxy]carbonylamino}-3-(4-chlorophenyl)butanoic acid; and converting crystalline (3R)-4-{[(1S)-2-methyl-1-(2-methylpropanoyloxy)propoxy]carbonylamino}-3-(4-chlorophenyl)butanoic acid hemihydrate into crystalline (3R)-4-{[(1S)-2-methyl-1-(2-methylpropanoyloxy)propoxy]carbonylamino}-3-(4-chlorophenyl)butanoic acid anhydrate by drying and/or by recrystallization.

In a ninth aspect, methods of treating a disease or disorder in a patient are provided comprising administering to a patient in need of such treatment a therapeutically effective amount of a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate, wherein the disease or disorder is selected from spasticity, gastroesophageal reflux disease, emesis, cough, substance addiction and abuse, neuropathic pain and musculoskeletal pain.

In a tenth aspect, kits are provided comprising a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating a disease or disorder chosen from selected from spasticity, gastroesophageal reflux disease, emesis, cough, substance addiction and abuse, neuropathic pain and musculoskeletal pain.

DETAILED DESCRIPTION

Definitions

Figure 1:
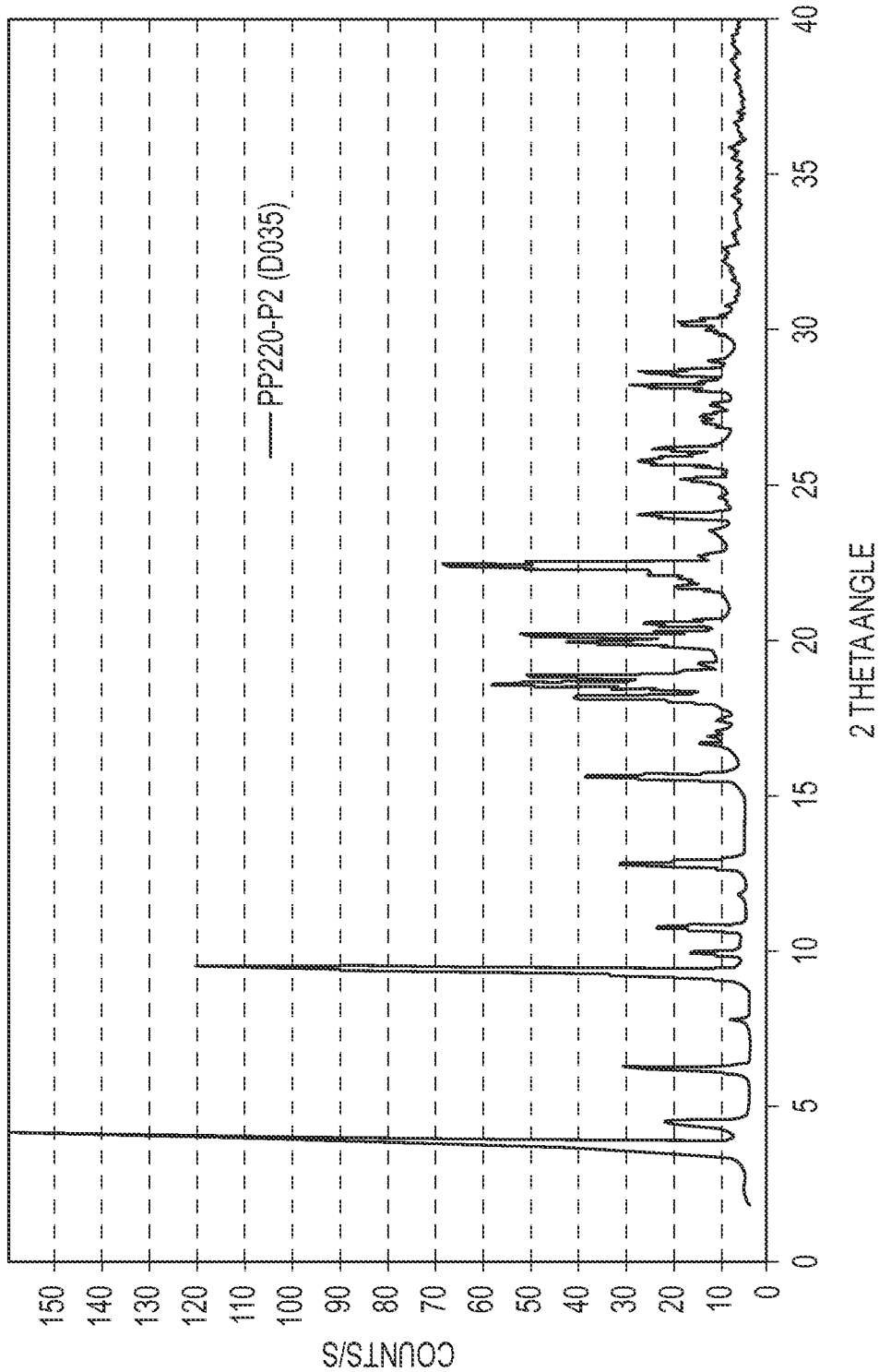
FIG. 1 shows an X-ray powder diffractogram of crystalline (3R)-4-{[(1S)-2-methyl-1-(2-methylpropanoyloxy)propoxy]carbonylamino}-3-(4-chlorophenyl)butanoic acid hemihydrate.

"Bioavailability" refers to the amount of a drug that reaches the systemic circulation of a patient following administration of the drug or prodrug thereof to the patient and may be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or prodrug thereof to the patient, and $T_{max}$ is the time to the maximum concentration ($C_{max}$) of a drug in the plasma or blood of a patient following administration of a dose of the drug or prodrug thereof to the patient.

"Crystalline" means having a regularly repeating arrangement of molecules.

"Crystalline (3R)-4-{[(1S)-2-methyl-1-(2-methylpropanoyloxy)propoxy]carbonylamino}-3-(4-chlorophenyl)butanoic acid anhydrate" refers to a compound in which crystalline (3R)-4-{[(1S)-2-methyl-1-(2-methylpropanoyloxy)propoxy]carbonylamino}-3-(4-chlorophenyl)butanoic acid is not associated with water molecules. Other chemical names for crystalline (3R)-4-{[(1S)-2-methyl-1-(2-methylpropanoyloxy)propoxy]carbonylamino}-3-(4-chlorophenyl)butanoic acid anhydrate include, without limitation, anhydrous crystalline (3R)-4-{[(1S)-2-methyl-1-(2-methylpropanoyloxy)propoxy]carbonylamino}-3-(4-chlorophenyl)butanoic acid.

"Crystalline (3R)-4-{[(1S)-2-methyl-1-(2-methylpropanoyloxy)propoxy]carbonylamino}-3-(4-chlorophenyl)butanoic acid hemihydrate" refers to a compound in which crystalline (3R)-4-{[(1S)-2-methylpropanoyloxy)propoxy]carbonylamino}-3-(4-chlorophenyl)butanoic acid is associated with water molecules, including fractional water molecules. For example, crystalline (3R)-4-{[(1S)-2- methyl-1-(2-methylpropanoyloxy)propoxy]carbonylamino}-3-(4-chlorophenyl)butanoic acid hemihydrate may contain less than one molar fraction of water, including fractional moles of water, per mole of crystalline (3R)-4-{[(1S)-2-methyl-1-(2-methylpropanoyloxy)propoxy]carbonylamino}-3-(4-chlorophenyl)butanoic acid. In some embodiments, crystalline (3R)-4-{[(1S)-2-methyl-1-(2-methylpropanoyloxy)propoxy]carbonylamino}-3-(4-chlorophenyl)butanoic acid hemihydrate contains one-half of one molar fraction of water per mole of crystalline (3R)-4-{[(1S)-2-methyl-1-(2-methylpropanoyloxy)propoxy]carbonylamino}-3-(4-chlorophenyl)butanoic acid. The molecules of water may be incorporated into the crystal lattice or loosely bound to the crystal lattice. In certain embodiments, the fractional equivalent of one-half molecule of water per molecule of crystalline (3R)-4-{[(1S)-2-methyl-1-(2-methylpropanoyloxy)propoxy]carbonylamino}-3-(4-chlorophenyl)butanoic acid is incorporated into the crystalline lattice and any additional water content is bound to the exterior of the crystalline lattice.

"Disease" refers to a disease, disorder, condition, symptom, or indication. This term is used interchangeably with the phrase "disease or disorder."

"Dosage form" refers to a form of a formulation that contains an amount of active agent or prodrug of an active agent, for example the (R)-baclofen prodrug (3R)-4-{[(1S)-2-methyl-1-(2-methylpropanoyloxy)propoxy]carbonylamino}-3-(4-chlorophenyl)butanoic acid (1), which can be administered to a patient to achieve a therapeutic effect. An oral dosage form is intended to be administered to a patient via the mouth and swallowed. Examples of oral dosage forms include capsules, tablets, and liquid suspensions. A dose of a drug may include one or more dosage forms administered simultaneously or over a period of time.

"Patient" includes mammals, such as for example, humans.

"Pharmaceutical composition" refers to a composition comprising at least one compound provided by the present disclosure and at least one pharmaceutically acceptable vehicle with which the compound is administered to a patient.

"Pharmaceutically acceptable" refers to approved or approvable by a regulatory agency of a federal or a state government, listed in the U.S. Pharmacopeia, or listed in other generally recognized pharmacopeia for use in mammals, including humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing, with which crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate can be administered to a patient, which does not destroy the pharmacological activity thereof, and which is nontoxic when administered in doses sufficient to provide a therapeutically effective amount of one or both of the compounds.

"Prodrug" refers to a derivative of an active compound (such as a drug) that undergoes a transformation under the conditions of use, such as within the body, to release the active compound or drug. Prodrugs are frequently, but not necessarily, pharmacologically inactive until converted into the active compound or drug. Prodrugs can be obtained by bonding a promoiety (defined herein), typically via a functional group, to a drug. For example, the (R)-baclofen prodrug (3R)-4-{[(1S)-2-methyl-1-(2-methylpropanoyloxy)propoxy]carbonylamino}-3-(4-chlorophenyl)butanoic acid (1) is metabolized within a patient's body to form the parent drug (R)-baclofen.

"Promoiety" refers to a group bonded to a drug, typically to a functional group of the drug, via one or more bonds that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach, or the agent may be supplied exogenously. For example, the promoiety of (3R)-4-{[(1S)-2-methyl-1-(2-methylpropanoyloxy)propoxy]carbonylamino}-3-(4-chlorophenyl)butanoic acid is:

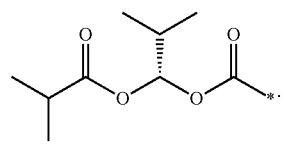

"Sustained release" refers to release of a therapeutic or preventive amount of a drug or an active metabolite thereof over a period of time that is longer than that of an immediate release formulation of the drug. For oral formulations, the term "sustained release" typically means release of the drug within the gastrointestinal tract lumen over a time period ranging, for example, from about 2 to about 30 hours, and in certain embodiments, over a time period ranging from about 4 to about 24 hours. Sustained release formulations achieve therapeutically effective concentrations of the drug in the systemic circulation over a prolonged period of time relative to that achieved by oral administration of an immediate release formulation of the drug.

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. A "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. A therapeutically effective amount in any given instance can be readily ascertained by those skilled in the art and/or is capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

Reference is now made in detail to certain embodiments of compounds, dosage forms, compositions, methods of synthesis and methods of use. The disclosed embodiments are not intended to be limiting of the claims. To the contrary, the claims are intended to cover all alternatives, modifications, and equivalents.

Crystalline (3R)-4-{[(1S)-2-methyl-1-(2-methylpropanoyloxy)propoxy]carbonylamino}-3-(4-chlorophenyl)butanoic acid (3R)-4-{[(1S)-2-methyl-1-(2-methylpropanoyloxy)propoxy]carbonylamino}-3-(4-chlorophenyl)butanoic acid (1) has the following structure:

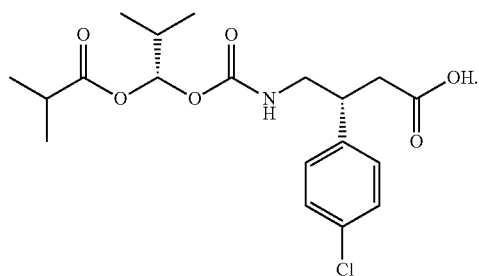

(1)

The synthesis of (3R)-4-{[(1S)-2-methyl-1-(2-methylpropanoyloxy)propoxy]carbonylamino}-3-(4-chlorophenyl)butanoic acid has been previously described in Gallop et al., U.S. Pat. Nos. 7,109,239 and 7,227,028, and in Gallop et al., PCT Publication No. WO 2005/019163 (see, e.g., PCT Publication No. WO 2005/019163, Example 82). A crystalline form of (3R)-4-{[(1S)-2-methyl-1-(2-methylpropanoyloxy)propoxy]carbonylamino}-3-(4-chlorophenyl)butanoic acid has also been previously described (see, e.g., PCT Publication Nos. WO 2008/086492 and WO 2009/096985). It is believed that the crystalline form disclosed in these publications is the anhydrate polymorph of (3R)-4-{[(1S)-2-methyl-1-(2-methylpropanoyloxy)propoxy]carbonylamino}-3-(4-chlorophenyl)butanoic acid. The x-ray powder diffractogram data of the anhydrate presented in this disclosure has not been previously described.

The inventors of the present disclosure have now discovered that a hemihydrate form of crystalline (3R)-4-{[(1S)-2-methyl-1-(2-methylpropanoyloxy)propoxy]carbonylamino}-3-(4-chlorophenyl)butanoic acid exists. The hemihydrate polymorph is also disclosed herein. Thus, crystalline (3R)-4-{[(1S)-2-methyl-1-(2-methylpropanoyloxy)propoxy]carbonylamino}-3-(4-chlorophenyl)butanoic acid can be prepared in more than one polymorphic crystalline form.

Crystalline (3R)-4-{[(1S)-2-methyl-1-(2-methylpropanoyloxy)propoxy]carbonylamino}-3-(4-chlorophenyl)butanoic acid hemihydrate In certain embodiments, crystalline (3R)-4-{[(1S)-2-methyl-1-(2-methylpropanoyloxy)propoxy]carbonylamino}-3-(4-chlorophenyl)butanoic acid exists as a hemihydrate. Crystalline (3R)-4-{[(1S)-2-methyl-1-(2-methylpropanoyloxy)propoxy]carbonylamino}-3-(4-chlorophenyl)butanoic acid hemihydrate is a solid exhibiting a highly ordered crystalline lattice as evidenced by an extensive pattern of both low-angle and high-angle reflections within the X-ray powder diffraction (XRPD) diffractogram.

Reference to crystalline (3R)-4-{[(1S)-2-methyl-1-(2-methylpropanoyloxy)propoxy]carbonylamino}-3-(4-chlorophenyl)butanoic acid hemihydrate includes all possible tautomeric forms of the conventional chemical structure for this compound and all isotopically labeled derivatives of this compound (e.g., $^2H$, $^3H$, $^{13}C$, $^{14}C$, $^{15}N$, $^{17}O$, $^{18}O$, etc.).

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits characteristic scattering angles (2θ) at least at 4.04°±0.2°, 6.47°±0.2°, 15.68°±0.2°, 18.91°±0.2° and 22.42°±0.2° in an X-ray powder diffractogram measured using Cu—K$_\alpha$ radiation.

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits characteristic scattering angles (2θ) at least at 4.04°±0.2°, 6.47°±0.2°, 9.46°±0.2°, 10.10°±0.2°, 10.87°±0.2°, 12.88°±0.2°, 15.68°±0.2°, 18.91°±0.2°, 19.96°±0.2°, 20.23°±0.2°, 22.42°±0.2°, 28.07°±0.2° and 28.53°±0.2° in an X-ray powder diffractogram measured using Cu—K$_\alpha$ radiation.

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits characteristic scattering angles (2θ) at least at 4.04°±0.2°, 6.47°±0.2°, 7.97°±0.2°, 9.46°±0.2°, 10.10°±0.2°, 10.87°±0.2°, 12.88°±0.2°, 15.68°±0.2°, 16.72°±0.2°, 18.16°±0.2°, 18.91°±0.2°, 19.33°±0.2°, 19.96°±0.2°, 20.23°±0.2°, 20.62°±0.2°, 21.76°±0.2°, 22.42°±0.2°, 23.55°±0.2°, 24.02°±0.2°, 25.13°±0.2°, 25.61°±0.2°, 26.09°±0.2°, 28.07°±0.2°, 28.53°±0.2°, 29.87°±0.2°, 30.45°±0.2°, 30.74°±0.2°, 31.52°±0.2°, 32.60°±0.2°, 35.94°±0.2° and 36.63°±0.2° in an X-ray powder diffractogram measured using Cu—K$_\alpha$ radiation.

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits the characteristic scattering angles (2θ) in an X-ray powder diffractogram measured using Cu—K$_\alpha$ radiation shown in FIG. 1.

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits a strong characteristic Raman spectrum band at 110 cm$^{-1}$.

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits characteristic Raman spectrum bands at least at 110 cm$^{-1}$ and 84 cm$^{-1}$.

In certain embodiments, crystalline (3R)-4-{[(1S)-2-methyl-1-(2-methylpropanoyloxy)propoxy]carbonylamino}-3-

(4-chlorophenyl)butanoic acid hemihydrate exhibits characteristic Raman spectrum bands at least at 779 cm$^{-1}$, 110 cm$^{-1}$ and 84 cm$^{-1}$.

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits characteristic Raman spectrum bands at least at 1744 cm$^{-1}$, 1600 cm$^{-1}$, 1453 cm$^{-1}$, 1290 cm$^{-1}$, 1238 cm$^{-1}$, 1201 cm$^{-1}$, 954 cm$^{-1}$, 872 cm$^{-1}$, 779 cm$^{-1}$, 635 cm$^{-1}$, 362 cm$^{-1}$, 315 cm$^{-1}$, 110 cm$^{-1}$ and 84 cm$^{-1}$.

Figure 2:
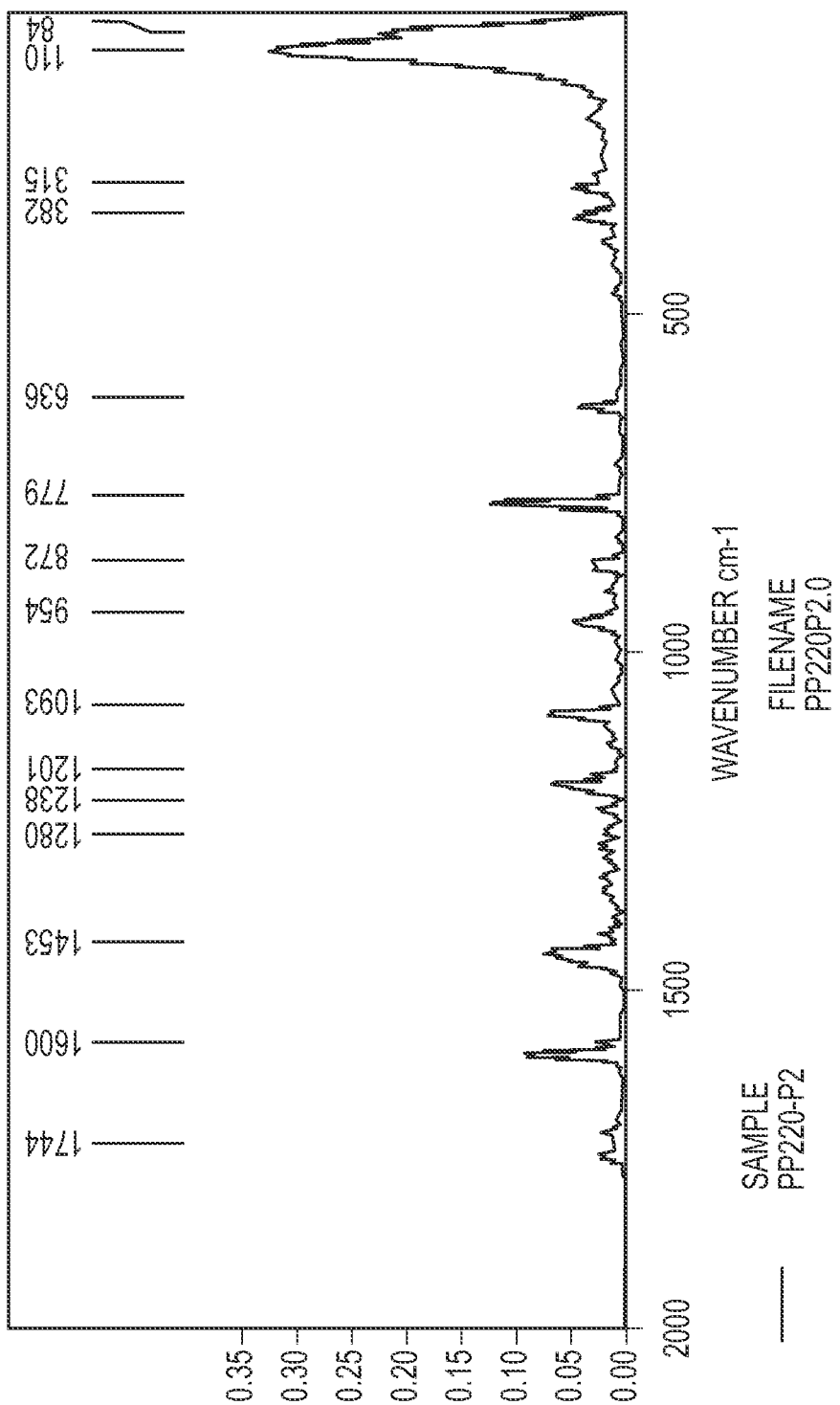
FIG. 2 shows a Raman spectrum of crystalline (3R)-4-{[(1S)-2-methyl-1-(2-methylpropanoyloxy)propoxy]carbonylamino}-3-(4-chlorophenyl)butanoic acid hemihydrate in the region from 50 to 2000 cm$^{-1}$.

In certain embodiments, crystalline (3R)-4-{[(1S)-2-methyl-1-(2-methylpropanoyloxy)propoxy]carbonylamino}-3-(4-chlorophenyl)butanoic acid hemihydrate exhibits the characteristic Raman spectrum in the region from 50 cm$^{-1}$ to 2000 cm$^{-1}$ shown in FIG. 2.

Crystalline (3R)-4-{[(1S)-2-methyl-1-(2-methylpropanoyloxy)propoxy]carbonylamino}-3-(4-chlorophenyl)butanoic acid hemihydrate can be characterized by the presence of two phase changes upon thermal decomposition. For example, in certain embodiments two points of thermal decomposition can be observed via TG-FTIR analysis. Additionally, in certain embodiments two melting point peaks can be observed using DSC analysis. The first phase transition can be attributed to the loss of water, which is characteristic of the hemihydrate polymorph. In certain embodiments, both phase changes can be attributable to the hemihydrate from of crystalline (3R)-4-{[(1S)-2-methyl-1-(2-methylpropanoyloxy)propoxy]carbonylamino}-3-(4-chlorophenyl)butanoic acid.

In certain embodiments, crystalline (3R)-4-{[(1S)-2-methyl-1-(2-methylpropanoyloxy)propoxy]carbonylamino}-3-(4-chlorophenyl)butanoic acid hemihydrate is generated at room temperature in an acetonitrile/water mixture having a critical water activity ($a_{wet}$) of greater than or equal to about 0.75±0.05. In certain embodiments, crystalline (3R)-4-{[(1S)-2-methyl-1-(2-methylpropanoyloxy)propoxy]carbonylamino}-3-(4-chlorophenyl)butanoic acid hemihydrate is generated at room temperature in an acetonitrile/water mixture having a water activity ($a_w$) of about 0.8. In certain embodiments, crystalline (3R)-4-{[(1S)-2-methyl-1-(2-methylpropanoyloxy)propoxy]carbonylamino}-3-(4-chlorophenyl)butanoic acid hemihydrate is generated at room temperature in an acetonitrile/water mixture having a $a_w$ of about 0.9. In certain embodiments, crystalline (3R)-4-{[(1S)-2-methyl-1-(2-methylpropanoyloxy)propoxy]carbonylamino}-3-(4-chlorophenyl)butanoic acid hemihydrate is generated at room temperature in an acetonitrile/water mixture having a $a_w$ selected from about 0.8 and about 0.9.

In certain embodiments, crystalline (3R)-4-{[(1S)-2-methyl-1-(2-methylpropanoyloxy)propoxy]carbonylamino}-3-(4-chlorophenyl)butanoic acid hemihydrate undergoes thermal decomposition and loses about 2.1% of its total weight at a temperature ranging from about 80° C. to about 130° C. using a thermogravimetric analyzer (TG) coupled with a Fourier-transform infrared (FTIR) spectrometer at a scan rate of about 10 K/min. In some embodiments, the 2.1% weight loss is attributable to water loss.

In certain embodiments, crystalline (3R)-4-{[(1S)-2-methyl-1-(2-methylpropanoyloxy)propoxy]carbonylamino}-3-(4-chlorophenyl)butanoic acid hemihydrate undergoes thermal decomposition at a temperature ranging from about 170° C. to about 190° C. using a thermogravimetric analyzer (TG) coupled with a Fourier-transform infrared (FTIR) spectrometer at a scan rate of about 10 K/min.

In certain embodiments, crystalline (3R)-4-{[(1S)-2-methyl-1-(2-methylpropanoyloxy)propoxy]carbonylamino}-3-(4-chlorophenyl)butanoic acid hemihydrate undergoes a first thermal decomposition at a temperature ranging from about 80° C. to about 130° C., and undergoes a second thermal decomposition at a temperature ranging from about 170° C. to about 190° C., using a thermogravimetric analyzer (TG) coupled with a Fourier-transform infrared (FTIR) spectrometer at a scan rate of about 10 K/min. In certain embodiments, crystalline (3R)-4-{[(1S)-2-methyl-1-(2-methylpropanoyloxy)propoxy]carbonylamino}-3-(4-chlorophenyl)butanoic acid hemihydrate loses about 2.1% of its total weight during the first thermal decomposition. In some embodiments, the 2.1% weight loss is attributable to water loss.

In certain embodiments, crystalline (3R)-4-{[(1S)-2-methyl-1-(2-methylpropanoyloxy)propoxy]carbonylamino}-3-(4-chlorophenyl)butanoic acid hemihydrate undergoes a melt/phase transition at a temperature ranging from about 90° C. to about 110° C. using differential scanning calorimetry at a heating rate of 20 K/min. In certain embodiments the thermal decomposition occurs at about 100° C. and in certain embodiments at about 99.8° C. In certain embodiments, crystalline (3R)-4-{[(1S)-2-methyl-1-(2-methylpropanoyloxy)propoxy]carbonylamino}-3-(4-chlorophenyl)butanoic acid hemihydrate undergoes a melt/phase transition at a temperature ranging from about 105° C. to about 125° C. using differential scanning calorimetry at a heating rate of 20 K/min. In certain embodiments the thermal decomposition occurs at about 115° C. and in certain embodiments at about 114.8° C.

In certain embodiments, crystalline (3R)-4-{[(1S)-2-methyl-1-(2-methylpropanoyloxy)propoxy]carbonylamino}-3-(4-chlorophenyl)butanoic acid hemihydrate undergoes a first melt/phase transition at a temperature ranging from about 90° C. to about 110° C., and also undergoes a second melt/phase transition at a temperature ranging from about 105° C. to about 125° C. using differential scanning calorimetry at a heating rate of 20 K/min. In certain embodiments the first thermal decomposition occurs at about 100° C. and the second thermal decomposition occurs at about 115° C. In certain embodiments the first thermal decomposition occurs at about 99.8° C. and the second thermal decomposition occurs at about 114.8° C.

In certain embodiments, crystalline (3R)-4-{[(1S)-2-methyl-1-(2-methylpropanoyloxy)propoxy]carbonylamino}-3-(4-chlorophenyl)butanoic acid hemihydrate is hygroscopic. In certain embodiments, crystalline (3R)-4-{[(1S)-2-methyl-1-(2-methylpropanoyloxy)propoxy]carbonylamino}-3-(4-chlorophenyl)butanoic acid hemihydrate is slightly hygroscopic above about 60% relative humidity. In certain embodiments, crystalline (3R)-4-{[(1S)-2-methyl-1-(2-methylpropanoyloxy)propoxy]carbonylamino}-3-(4-chlorophenyl)butanoic acid hemihydrate comprises from about 2 wt%-about 3 wt % water. In certain embodiments, crystalline (3R)-4-{[(1S)-2-methyl-1-(2-methylpropanoyloxy)propoxy]carbonylamino}-3-(4-chlorophenyl)butanoic acid hemihydrate contains about 2.15 wt % water at 50% relative humidity as measured by dynamic vapor sorption. In certain embodiments, crystalline (3R)-4-{[(1S)-2-methyl-1-(2-methylpropanoyloxy)propoxy]carbonylamino}-3-(4-chlorophenyl)butanoic acid hemihydrate contains about 3 wt % water at 95% relative humidity as measured by dynamic vapor sorption.

Crystalline (3R)-4-{[(1S)-2-methyl-1-(2-methylpropanoyloxy)propoxy]carbonylamino}-3-(4-chlorophenyl)butanoic acid anhydrate In certain embodiments, crystalline (3R)-4-{[(1S)-2-methyl-1-(2-methylpropanoyloxy)propoxy]carbonylamino}-3-(4-chlorophenyl)butanoic acid exists as an anhydrate. Crystalline (3R)-4-{[(1S)-2-methyl-1-(2-methylpropanoyloxy)propoxy]carbonylamino}-3-(4-chlorophenyl)butanoic acid anhydrate is a solid exhibiting a highly ordered crystalline lattice as evidenced by an extensive pattern of both low-angle and high-angle reflections within the X-ray powder diffraction (XRPD) diffractogram Reference to crystalline (3R)-4-{[(1S)-2-methyl-1-(2-methylpropanoyloxy)propoxy]carbonylamino}-3-(4-chlorophenyl)butanoic acid anhydrate includes all possible tautomeric forms of the conventional chemical structure for this compound and all isotopically labeled derivatives of this compound (e.g., $^2H$, $^3H$, $^{13}C$, $^{14}C$, $^{15}N$, $^{17}O$, $^{18}O$, etc.).

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits characteristic scattering angles (2θ) at least at 4.33°±0.2°, 4.76°±0.2°, 11.06°±0.2° and 11.61°±0.2° in an X-ray powder diffractogram measured using Cu—$K_\alpha$ radiation.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits characteristic scattering angles (2θ) at least at 4.33°±0.2°, 4.76°±0.2°, 5.83°±0.2°, 9.07°±0.2°, 9.46°±0.2°, 10.54°±0.2°, 11.06°±0.2°, 11.61°±0.2°, 12.94°±0.2°, 17.46°±0.2°, 17.84°±0.2°, 18.01°±0.2°, 19.36°±0.2°, 20.01°±0.2° and 21.26°±0.2° in an X-ray powder diffractogram measured using Cu—$K_\alpha$ radiation.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits characteristic scattering angles (2θ) at least at 4.33°±0.2°, 4.76°±0.2°, 5.83°±0.2°, 6.93°±0.2°, 9.07°±0.2°, 9.46°±0.2°, 10.54°±0.2°, 11.06°±0.2°, 11.61°±0.2°, 12.94°±0.2°, 15.25°±0.2°, 16.55°±0.2°, 17.46°±0.2°, 17.84°±0.2°, 18.01°±0.2°, 18.41°±0.2°, 18.69°±0.2°, 18.93°±0.2°, 19.36°±0.2°, 20.01°±0.2°, 20.46°±0.2°, 21.26°±0.2°, 21.75°±0.2°, 22.19°±0.2°, 22.56°±0.2°, 23.35°±0.2°, 23.85°±0.2°, 24.84°±0.2°, 25.96°±0.2°, 26.78°±0.2°, 27.29°±0.2°, 28.69°±0.2°, 29.39°±0.2°, 31.22°±0.2°, 32.35°±0.2°, 33.47°±0.2°, 34.62°±0.2° and 36.08°±0.2° in an X-ray powder diffractogram measured using Cu—$K_\alpha$ radiation.

Figure 3:
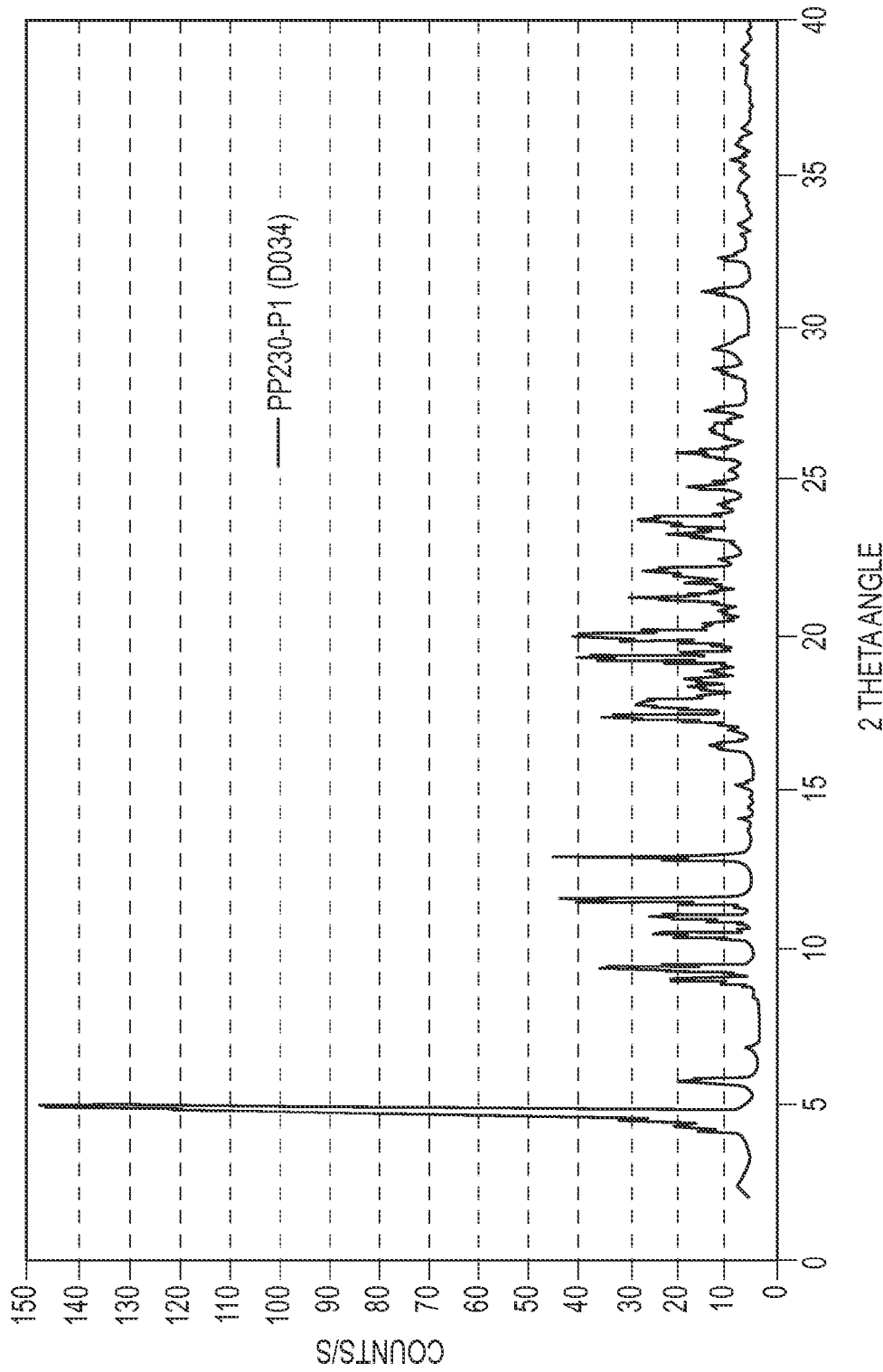
FIG. 3 shows an X-ray powder diffractogram of crystalline (3R)-4-{[(1S)-2-methyl-1-(2-methylpropanoyloxy)propoxy]carbonylamino}-3-(4-chlorophenyl)butanoic acid anhydrate.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits the characteristic scattering angles (2θ) in an X-ray powder diffractogram measured using Cu—$K_\alpha$ radiation shown in FIG. 3.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits a strong characteristic Raman spectrum band at 119 cm$^{-1}$.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits characteristic Raman spectrum bands at least at 119 cm$^{-1}$ and 85 cm$^{-1}$.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits characteristic Raman spectrum bands at least at 1599 cm$^{-1}$, 1447 cm$^{-1}$, 798 cm$^{-1}$, 119 cm$^{-1}$ and 85 cm$^{-1}$.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits characteristic Raman spectrum bands at least at 1747 cm$^{-1}$, 1599 cm$^{-1}$, 1447 cm$^{-1}$, 1412 cm$^{-1}$, 1335 cm$^{-1}$, 1203 cm$^{-1}$, 1092 cm$^{-1}$, 954 cm$^{-1}$, 868 cm$^{-1}$, 798 cm$^{-1}$, 637 cm$^{-1}$, 401 cm$^{-1}$, 348 cm$^{-1}$, 317 cm$^{-1}$, 244 cm$^{-1}$, 119 cm$^{-1}$ and 85 cm$^{-1}$.

Figure 4:
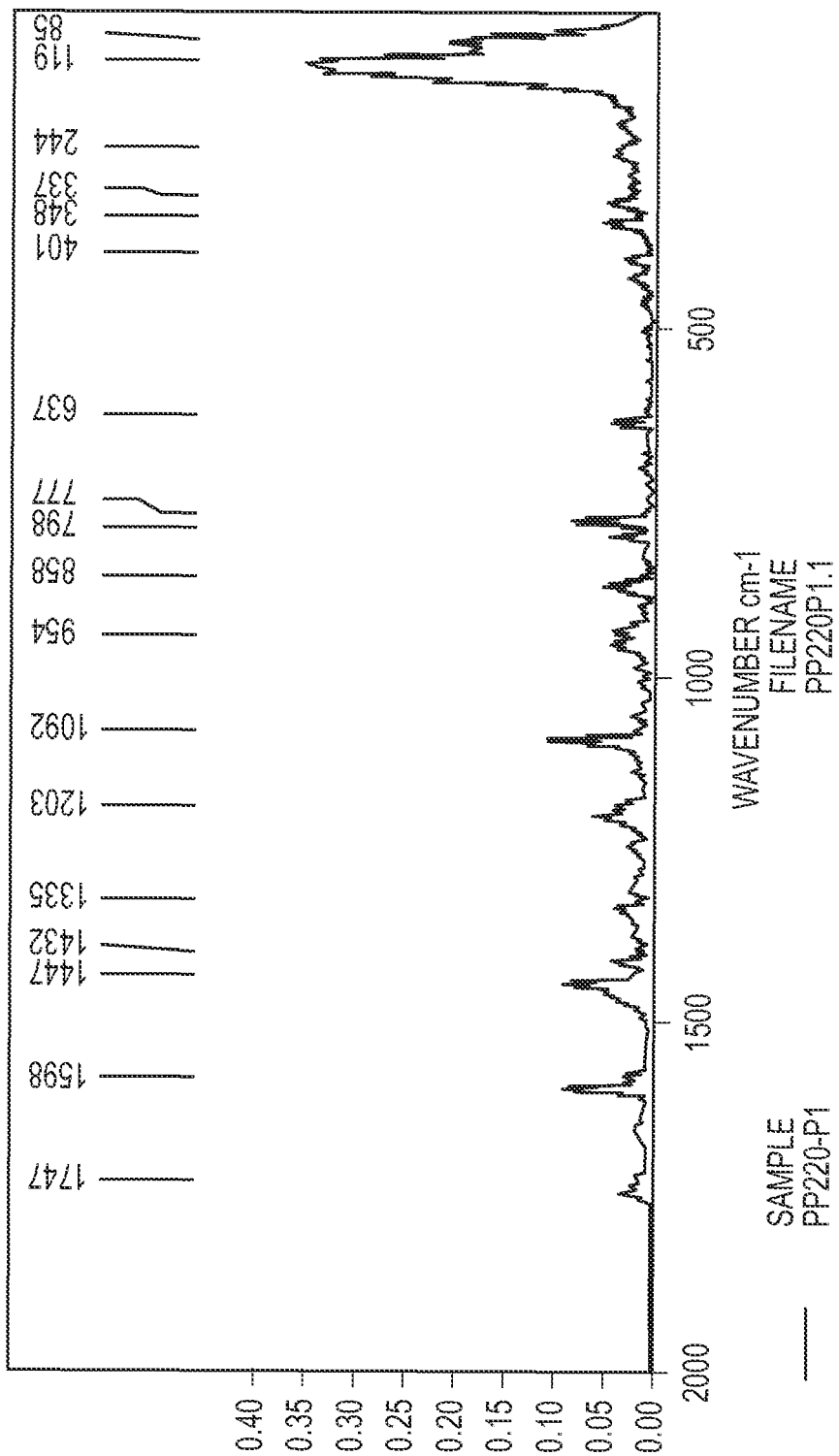
FIG. 4 shows a Raman spectrum of crystalline (3R)-4-{[(1S)-2-methyl-1-(2-methylpropanoyloxy)propoxy]carbonylamino}-3-(4-chlorophenyl)butanoic acid anhydrate in the region from 50 to 2000 cm$^{-1}$.

In certain embodiments, crystalline (3R)-4-{[(1S)-2-methyl-1-(2-methylpropanoyloxy)propoxy]carbonylamino}-3-(4-chlorophenyl)butanoic acid anhydrate exhibits the characteristic Raman spectrum in the region from 50 cm$^{-1}$ to 2000 cm$^{-1}$ shown in FIG. 4.

In certain embodiments, crystalline (3R)-4-{[(1S)-2-methyl-1-(2-methylpropanoyloxy)propoxy]carbonylamino}-3-(4-chlorophenyl)butanoic acid anhydrate is generated at room temperature in an acetonitrile/water mixture having a critical water activity ($a_{wet}$) of less than or equal to about 0.75±0.05. In certain embodiments, crystalline (3R)-4-{[(1S)-2-methyl-1-(2-methylpropanoyloxy)propoxy]carbonylamino}-3-(4-chlorophenyl)butanoic acid anhydrate is generated at room temperature in an acetonitrile/water mixture having a water activity ($a_{wet}$) of about 0.7. In certain embodiments, crystalline (3R)-4-{[(1S)-2-methyl-1-(2-methylpropanoyloxy)propoxy]carbonylamino}-3-(4-chlorophenyl)butanoic acid anhydrate is generated at room temperature in an acetonitrile/water mixture having a $a_w$ of about 0.6. In certain embodiments, crystalline (3R)-4-{[(1S)-2-methyl-1-(2-methylpropanoyloxy)propoxy]carbonylamino}-3-(4-chlorophenyl)butanoic acid anhydrate is generated at room temperature in an acetonitrile/water mixture having a $a_w$ of about 0.5. In certain embodiments, crystalline (3R)-4-{[(1S)-2-methyl-1-(2-methylpropanoyloxy)propoxy]carbonylamino}-3-(4-chlorophenyl)butanoic acid anhydrate is generated at room temperature in an acetonitrile/water mixture having a $a_w$ of about 0.4. In certain embodiments, crystalline (3R)-4-{[(1S)-2-methyl-1-(2-methylpropanoyloxy)propoxy]carbonylamino}-3-(4-chlorophenyl)butanoic acid anhydrate is generated at room temperature in an acetonitrile/water mixture having a $a_w$ of about 0.3. In certain embodiments, crystalline (3R)-4-{[(1S)-2-methyl-1-(2-methylpropanoyloxy)propoxy]carbonylamino}-3-(4-chlorophenyl)butanoic acid anhydrate is generated at room temperature in an acetonitrile/water mixture having a $a_w$ selected from about 0.7, about 0.6, about 0.5, about 0.4 and about 0.3.

In certain embodiments, crystalline (3R)-4-{[(1S)-2-methyl-1-(2-methylpropanoyloxy)propoxy]carbonylamino}-3-(4-chlorophenyl)butanoic acid anhydrate undergoes thermal decomposition at a temperature ranging from about 170° C. to about 190° C. using a thermogravimetric analyzer (TG) coupled with a Fourier-transform infrared (FTIR) spectrometer at a scan rate of about 10 K/min.

In certain embodiments, crystalline (3R)-4-{[(1S)-2-methyl-1-(2-methylpropanoyloxy)propoxy]carbonylamino}-3-(4-chlorophenyl)butanoic acid anhydrate undergoes a melt/phase transition at a temperature ranging from about 120° C. to about 140° C. using differential scanning calorimetry at a heating rate of 20 K/min. In certain embodiments, the melt/phase transition occurs at about 131° C. and in certain embodiments at about 131.3° C.

In certain embodiments, crystalline (3R)-4-{[(1S)-2-methyl-1-(2-methylpropanoyloxy)propoxy]carbonylamino}-3-(4-chlorophenyl)butanoic acid anhydrate is not hygroscopic. In certain embodiments, crystalline (3R)-4-{[(1S)-2-methyl-1-(2-methylpropanoyloxy)propoxy]carbonylamino}-3-(4-chlorophenyl)butanoic acid anhydrate contains less than about 0.05 wt % water at 50% relative humidity as measured by dynamic vapor sorption. In certain embodiments, crystalline (3R)-4-{[(1S)-2-methyl-1-(2-methylpropanoyloxy)propoxy]carbonylamino}-3-(4-chlorophenyl)butanoic acid anhydrate contains less than about 0.1 wt % water at 95% relative humidity as measured by dynamic vapor sorption.

Methods of Synthesis

In certain embodiments, crystalline (3R)-4-{[(1S)-2-methyl-1-(2-methylpropanoyloxy)propoxy]carbonylamino}-3-(4-chlorophenyl)butanoic acid anhydrate can be synthesized by: (i) forming a solution of diastereomers comprising (3R)-4-{[(1S)-2-methyl-1-(2-methylpropanoyloxy)propoxy]carbonylamino}-3-(4-chlorophenyl)butanoic acid and (3R)-4-{[(1R)-2-methyl-1-(2-methylpropanoyloxy)propoxy]carbonylamino}-3-(4-chlorophenyl)butanoic acid; (ii) selectively crystallizing the (3R)-4-{[(1S)-2-methylpropanoyloxy)propoxy]carbonylamino}-3-(4-chlorophenyl)butanoic acid diastereomer as a hemihydrate; and (iii) separating the crystalline (3R)-4-{[(1S)-2-methyl-1-(2-methylpropanoyloxy)propoxy]carbonylamino}-3-(4-chlorophenyl)butanoic acid hemihydrate diastereomer from the solution. In certain embodiments, the solution is water-containing or aqueous.

In certain embodiments, crystalline (3R)-4-{[(1S)-2-methyl-1-(2-methylpropanoyloxy)propoxy]carbonylamino}-3-(4-chlorophenyl)butanoic acid hemihydrate can be converted into crystalline (3R)-4-{[(1S)-2-methyl-1-(2-methylpropanoyloxy)propoxy]carbonylamino}-3-(4-chlorophenyl)butanoic acid anhydrate by a method selected from drying and recrystallization.

Crystalline (3R)-4-{[(1S)-2-methyl-1-(2-methylpropanoyloxy)propoxy]carbonylamino}-3-(4-chlorophenyl)butanoic acid hemihydrate (1b) can be synthesized following the methods described in Scheme 1 and Scheme 2 below. Additionally, the individual diastereomers of crystalline (3R)-4-{[(±)-2-methyl-1-(2-methylpropanoyloxy)propoxy]carbonylamino}-3-(4-chlorophenyl)butanoic acid can be separated efficiently via the methods described in Scheme 1. Crystalline (3R)-4-{[(1S)-2-methyl-1-(2-methylpropanoyloxy)propoxy]carbonylamino}-3-(4-chlorophenyl)butanoic acid anhydrate (1a) can be synthesized following the methods described in Scheme 3 and Scheme 4 below.

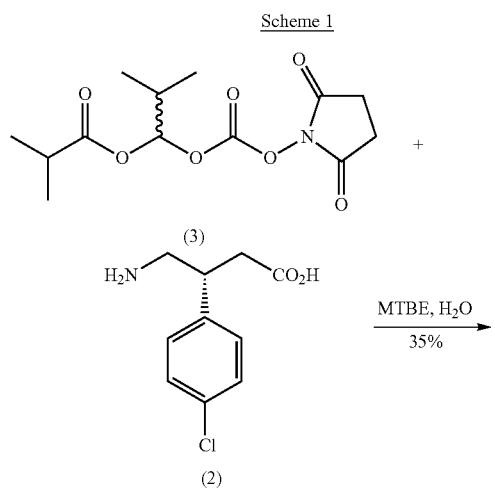

Scheme 1

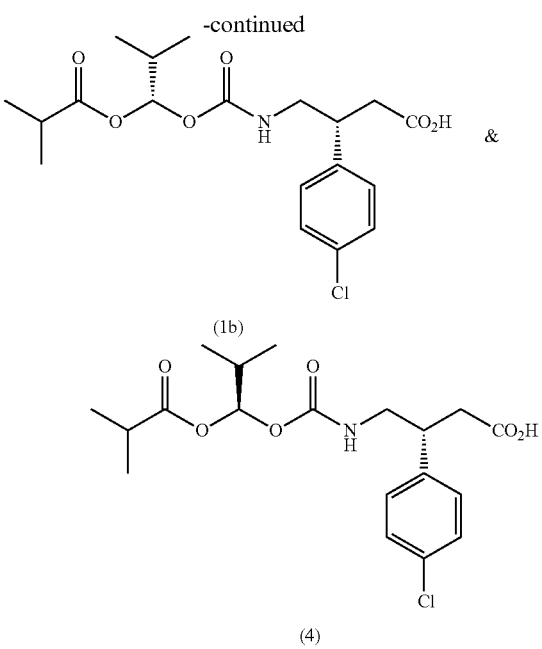

In certain embodiments, crystalline (3R)-4-{[(1S)-2-methyl-1-(2-methylpropanoyloxy)propoxy]carbonylamino}-3-(4-chlorophenyl)butanoic acid hemihydrate (1b) can be prepared by steps comprising providing a solution or suspension comprising 1-((2,5-dioxopyrrolidin-1-yl-oxycarbonyloxy)-2-methylpropyl)-2-methylpropanoate (3) prepared as a racemic mixture of (R)-1-((2,5-dioxopyrrolidin-1-yl-oxycarbonyloxy)-2-methylpropyl)-2-methylpropanoate and (S)-1-((2,5-dioxopyrrolidin-1-yl-oxycarbonyloxy)-2-methylpropyl)-2-methylpropanoate, (R)-baclofen (2), water and a solvent; and adjusting the temperature of the solution or suspension to provide (3R)-4-{[(1S)-2-methyl-1-(2-methylpropanoyloxy)propoxy]carbonylamino}-3-(4-chlorophenyl)butanoic acid hemihydrate (1b) and (3R)-4-{[(1R)-2-methyl-1-(2-methylpropanoyloxy)propoxy]carbonylamino}-3-(4-chlorophenyl)butanoic acid (4).

In certain embodiments, the solvent is selected from methyl tert-butyl ether, acetonitrile, toluene, chlorobenzene, methylcyclohexane, heptane, methanol, ethanol, diethyl ether, tetrahydrofuran, tert-amyl methyl ether and combinations of the foregoing. In certain embodiments, the solvent is methyl tert-butyl ether. In certain embodiments, the solvent is not dimethylsulfoxide, dimethylformamide, or n-methylpyrrolidine. In certain embodiments, the solution is aqueous. In the exemplary embodiment depicted in Scheme 1, the solvent is methyl tert-butyl ether.

In certain embodiments, the solution comprises solvent in an amount ranging from about 20 v/v %-about 50 v/v %. In certain embodiments, the solution comprises solvent in an amount of about 35 v/v %. In the exemplary embodiment depicted in Scheme 1, the solution comprises methyl tert-butyl ether in an amount of about 35 v/v %. In certain embodiments, the solution comprises water in an amount ranging from about 50 v/v % to about 80 v/v %. In certain embodiments, the solution comprises water in an amount of about 65 v/v %. In certain embodiments, the solution comprises about 35 v/v % methyl tert-butyl ether and about 65% v/v water.

In certain embodiments, the combination and dissolution of 1-((2,5-dioxopyrrolidin-1-yl-oxycarbonyloxy)-2-methylpropyl)-2-methylpropanoate (3) prepared as a racemic mixture of (R)-1-((2,5-dioxopyrrolidin-1-yl-oxycarbonyloxy)-2- methylpropyl)-2-methylpropanoate and (S)-1-((2,5-dioxopyrrolidin-1-yl-oxycarbonyloxy)-2-methylpropyl)-2-methylpropanoate, and (R)-baclofen (2) in solution can be carried out at elevated temperature, up to and including the boiling point of the solvent used. Accordingly, in certain embodiments, racemic 1-((2,5-dioxopyrrolidin-1-yl-oxycarbonyloxy)-2-methylpropyl-2-methylpropanoate (3) and (R)-baclofen (2) can be dissolved in a solution with heating and optionally, with shaking and stirring. The heated solution may be maintained at elevated temperature to ensure complete dissolution of racemic 1-((2,5-dioxopyrrolidin-1-yl-oxycarbonyloxy)-2-methylpropyl-2-methylpropanoate (3) and (R)-baclofen (2). The heated solution may also be filtered at elevated temperature to remove any undissolved components. Then racemic 1-((2,5-dioxopyrrolidin-1-yl-oxycarbonyloxy)-2-methylpropyl-2-methylpropanoate (3) and (R)-baclofen (2) react in the solution to yield (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid (4).

(3R)-4-{[(1S)-2-methyl-1-(2-methylpropanoyloxy)propoxy]carbonylamino}-3-(4-chlorophenyl)butanoic acid hemihydrate can then be crystallized out of solution leaving (3R)-4-{[(1R)-2-methyl-1-(2-methylpropanoyloxy)propoxy]carbonylamino}-3-(4-chlorophenyl)butanoic acid (4) in solution. Crystallization of (3R)-4-{[(1S)-2-methyl-1-(2-methylpropanoyloxy)propoxy]carbonylamino}-3-(4-chlorophenyl)butanoic acid hemihydrate can occur by any number of conventional means and/or by the methods disclosed hereinbelow.

In certain embodiments, (R)-baclofen can be recycled from diastereomer (3R)-4-{[(1R)-2-methyl-1-(2-methylpropanoyloxy)propoxy]carbonylamino}-3-(4-chlorophenyl)butanoic acid (4) by hydrolysis of the (3R)-4-{[(1R)-2-methyl-1-(2-methylpropanoyloxy)propoxy]carbonylamino}-3-(4-chlorophenyl)butanoic acid (4) remaining in solution according to Scheme 2.

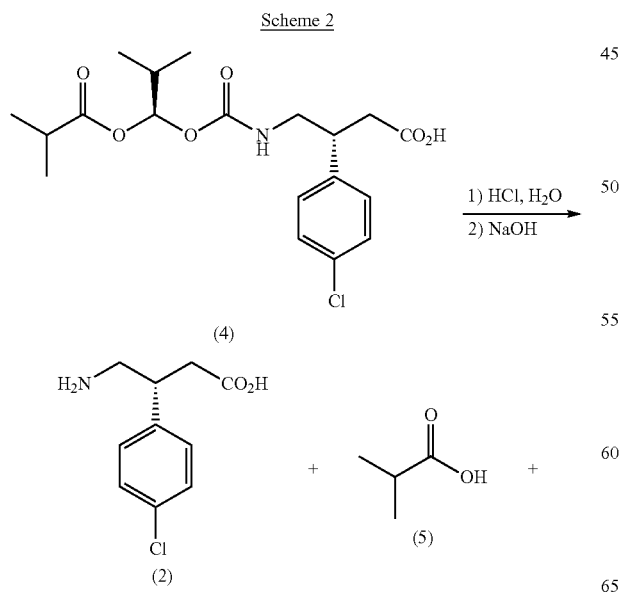

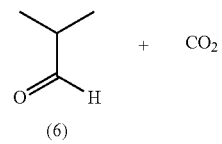

In Scheme 2, the hydrolysis of (3R)-4-{[(1R)-2-methyl-1-(2-methylpropanoyloxy)propoxy]carbonylamino}-3-(4-chlorophenyl)butanoic acid (4) yields (R)-baclofen (2), isobutyric acid (5), isobutyraldehyde (6), and carbon dioxide. The recycled (R)-baclofen (2) can then be reused in further syntheses of crystalline (3R)-4-{[(1S)-2-methyl-1-(2-methylpropanoyloxy)propoxy]carbonylamino}-3-(4-chlorophenyl)butanoic acid hemihydrate (1b) via the method of Scheme 1.

Hydrolysis can occur in one or two steps. In certain embodiments, the hydrolysis of (3R)-4-{[(1R)-2-methyl-1-(2-methylpropanoyloxy)propoxy]carbonylamino}-3-(4-chlorophenyl)butanoic acid (4) is achieved by adding a first solution comprising an acid and water to the resultant crystallization solution from Scheme 1; and thereafter adding a base.

Crystalline (3R)-4-{[(1S)-2-methyl-1-(2-methylpropanoyloxy)propoxy]carbonylamino}-3-(4-chlorophenyl)butanoic acid anhydrate (1a) can be synthesized following the methods described in Scheme 3 and Scheme 4 below.

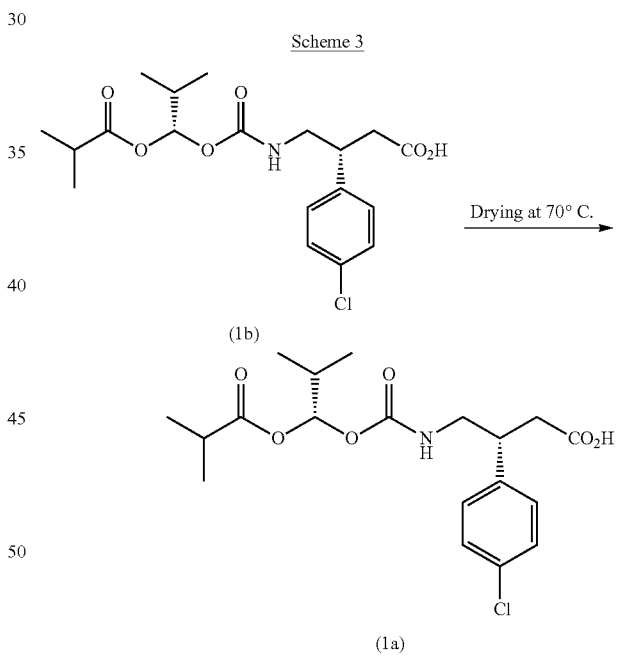

In Scheme 3, crystalline (3R)-4-{[(1S)-2-methyl-1-(2-methylpropanoyloxy)propoxy]carbonylamino}-3-(4-chlorophenyl)butanoic acid hemihydrate (1b) is dried to produce crystalline (3R)-4-{[(1S)-2-methyl-1-(2-methylpropanoyloxy)propoxy]carbonylamino}-3-(4-chlorophenyl)butanoic acid anhydrate (1a). Crystalline (3R)-4-{[(1S)-2-methyl-1-(2-methylpropanoyloxy)prop oxy]carbonylamino}-3-(4-chlorophenyl)butanoic acid hemihydrate (1b) may be produced, for example, according to the methods described above.

Drying can occur via any conventional means including, for example, air drying, drying under vacuum, drying at an elevated temperature, or any combination of the foregoing. In certain embodiments, the drying can be carried out at elevated temperature, up to but excluding the melting or thermal decomposition temperature of crystalline (3R)-4-{[(1S)-2-methyl-1-(2-methylpropanoyloxy)propoxy]carbonylamino}-3-(4-chlorophenyl)butanoic acid anhydrate (1a). In some embodiments, the drying can be carried out at a temperature range of about 30° C. to below about 90° C., and in certain embodiments at a temperature range of about 40° C. to 80° C. In the exemplary embodiment depicted in Scheme 3, the drying occurs at a temperature of about 70° C.

The drying of crystalline (3R)-4-{[(1S)-2-methyl-1-(2-methylpropanoyloxy)propoxy]carbonylamino}-3-(4-chlorophenyl)butanoic acid hemihydrate (1b) yields crystalline (3R)-4-{[(1S)-2-methyl-1-(2-methylpropanoyloxy)propoxy]carbonylamino}-3-(4-chlorophenyl)butanoic acid anhydrate (1a) as a white crystalline solid.

Scheme 4

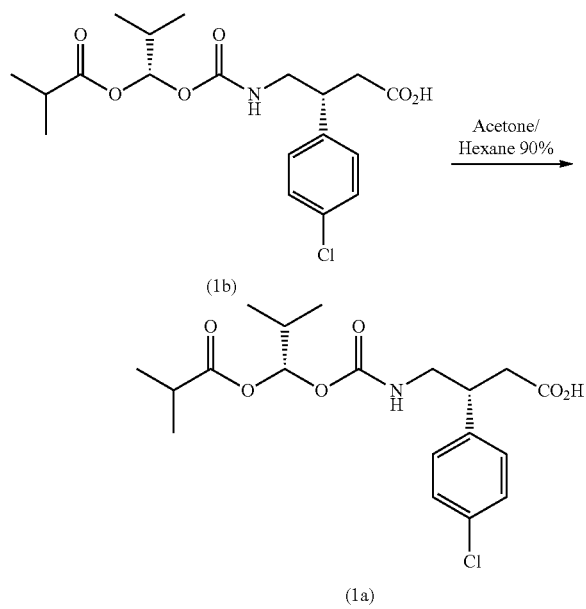

In certain embodiments, crystalline (3R)-4-{[(1S)-2-methyl-1-(2-methylpropanoyloxy)propoxy]carbonylamino}-3-(4-chlorophenyl)butanoic acid hemihydrate (1b) can be recrystallized to crystallize (3R)-4-{[(1S)-2-methyl-1-(2-methylpropanoyloxy)propoxy]carbonylamino}-3-(4-chlorophenyl)butanoic acid anhydrate (1a).

In certain embodiments, crystalline (3R)-4-{[(1S)-2-methyl-1-(2-methylpropanoyloxy)propoxy]carbonylamino}-3-(4-chlorophenyl)butanoic acid anhydrate (1a) can be prepared by steps comprising providing a solution or suspension comprising crystalline (3R)-4-{[(1S)-2-methyl-1-(2-methylpropanoyloxy)propoxy]carbonylamino}-3-(4-chlorophenyl)butanoic acid hemihydrate (1b) and a solvent; and adjusting the temperature of the solution or suspension to provide crystalline (3R)-4-{[(1S)-2-methyl-1-(2-methylpropanoyloxy)propoxy]carbonylamino}-3-(4-chlorophenyl)butanoic acid anhydrate (1a).

In certain embodiments, the solvent is selected from acetone, hexane, methyl tert-butyl ether, acetonitrile, toluene, chlorobenzene, methylcyclohexane, heptane, methanol, ethanol, diethyl ether, tetrahydrofuran, tert-amyl methyl ether and combinations of the foregoing. In certain embodiments, the solvent is a combination of acetone and hexane. In the exemplary embodiment depicted in Scheme 1, the solvent is a combination of acetone and hexane.

In certain embodiments, the solution comprises solvent in an amount ranging from about 70 v/v %-about 100 v/v %. In certain embodiments, the solution comprises solvent in an amount of about 90 v/v %. In the exemplary embodiment depicted in Scheme 1, the solution comprises a combination of acetone and hexane in an amount of about 90 v/v %. In certain embodiments, the solution comprises water in an amount ranging from about 0 v/v % to about 30 v/v %. In certain embodiments, the solution comprises water in an amount of about 15 v/v %. In certain embodiments, the solution comprises about 90 v/v % of a combination of acetone and hexane and about 10% v/v water.

In certain embodiments, crystalline (3R)-4-{[(1S)-2-methyl-1-(2-methylpropanoyloxy)propoxy]carbonylamino}-3-(4-chlorophenyl)butanoic acid hemihydrate (1b) can be maintained at ambient or room temperature to crystallize (3R)-4-{[(1S)-2-methyl-1-(2-methylpropanoyloxy)propoxy]carbonylamino}-3-(4-chlorophenyl)butanoic acid anhydrate (1a). Ambient or room temperature refers to a temperature to which humans are accustomed or have become acclimatized. In certain embodiments, room temperature includes temperatures in the range of about 20° C.-27° C. and/or temperatures in the range of about 68° F.-80° F. In certain embodiments, room temperature is 20° C., in certain embodiments 25° C., in certain embodiments 68° F., and in certain embodiments 77° F. Other methods known to those of skill in the crystallization arts, (e.g., solvent evaporation, drowning, chemical reaction, seeding with a small quantity of the desired crystal form, etc.) may also be employed to crystallize (3R)-4-{[(1S)-2-methyl-1-(2-methylpropanoyloxy)propoxy]carbonylamino}-3-(4-chlorophenyl)butanoic acid anhydrate (1a).

In certain embodiments, the recrystallization of (3R)-4-{[(1S)-2-methyl-1-(2-methylpropanoyloxy)propoxy]carbonylamino}-3-(4-chlorophenyl)butanoic acid anhydrate (1a) from a solution comprising crystalline (3R)-4-{[(1S)-2-methyl-1-(2-methylpropanoyloxy)propoxy]carbonylamino}-3-(4-chlorophenyl)butanoic acid hemihydrate (1b) and a solvent can be carried out at elevated temperature, up to and including the boiling point of the solvent used. Accordingly, in certain embodiments, crystalline (3R)-4-{[(1S)-2-methyl-1-(2-methylpropanoyloxy)propoxy]carbonylamino}-3-(4-chlorophenyl)butanoic acid hemihydrate (1b) can be dissolved in a solvent by heating and optionally, with shaking and stirring. The heated solution may be maintained at elevated temperature to ensure complete dissolution of crystalline (3R)-4-{[(1S)-2-methyl-1-(2-methylpropanoyloxy)propoxy]carbonylamino}-3-(4-chlorophenyl)butanoic acid hemihydrate (1b). The heated solution may also be filtered at elevated temperature to remove any undissolved components. Then (3R)-4-{[(1S)-2-methyl-1-(2-methylpropanoyloxy)propoxy]carbonylamino}-3-(4-chlorophenyl)butanoic acid anhydrate (1a) crystallizes out of the solution.

The recrystallization of crystalline (3R)-4-{[(1S)-2-methyl-1-(2-methylpropanoyloxy)propoxy]carbonylamino}-3-(4-chlorophenyl)butanoic acid hemihydrate (1b) yields crystalline (3R)-4-{[(1S)-2-methyl-1-(2-methylpropanoyloxy)propoxy]carbonylamino}-3-(4-chlorophenyl)butanoic acid anhydrate (1a) as a white crystalline solid.

Crystallization of (3R)-4-{[(1S)-2-methyl-1-(2-methylpropanoyloxy)propoxy]carbonylamino}-3-(4-chlorophenyl)butanoic acid hemihydrate In certain embodiments, the solution comprising 1-((2,5-dioxopyrrolidin-1-yl-oxycarbonyloxy)-2-methylpropyl)-2-methylpropanoate (3) prepared as a racemic mixture of (R)-

1-((2,5-dioxopyrrolidin-1-yl-oxycarbonyloxy)-2-methylpropyl)-2-methylpropanoate and (S)-1-((2,5-dioxopyrrolidin-1-yl-oxycarbonyloxy)-2-methylpropyl)-2-methylpropanoate, and (R)-baclofen (2) can be slowly cooled to crystallize (3R)-4-{[(1S)-2-methyl-1-(2-methylpropanoyloxy)propoxy]carbonylamino}-3-(4-chlorophenyl)butanoic acid hemihydrate (1b). Compound (1b) may be separated from (3R)-4-{[(1R)-2-methyl-1-(2-methylpropanoyloxy)propoxy]carbonylamino}-3-(4-chlorophenyl)butanoic acid (4) and residual solvent by filtration and/or drying under reduced pressure. In certain embodiments, the solution can be cooled to a temperature ranging from about 0° C. to about 25° C. to crystallize (3R)-4-{[(1S)-2-methyl-1-(2-methylpropanoyloxy)propoxy]carbonylamino}-3-(4-chlorophenyl)butanoic acid hemihydrate (1b).

In certain embodiments, the solution comprising racemic 1-((2,5-dioxopyrrolidin-1-yl-oxycarbonyloxy)-2-methylpropyl-2-methylpropanoate (3) and (R)-baclofen (2) can be maintained at ambient or room temperature to crystallize (3R)-4-{[(1S)-2-methyl-1-(2-methylpropanoyloxy)propoxy]carbonylamino}-3-(4-chlorophenyl)butanoic acid hemihydrate (1b), which may be separated from (3R)-4-{[(1R)-2-methyl-1-(2-methylpropanoyloxy)propoxy]carbonylamino}-3-(4-chlorophenyl)butanoic acid (4) and residual solvent by filtration and/or drying under reduced pressure. Ambient or room temperature refers to a temperature to which humans are accustomed or have become acclimatized. In certain embodiments, room temperature includes temperatures in the range of about 20° C.-27° C. and/or temperatures in the range of about 68° F.-80° F. In certain embodiments, room temperature is 20° C., in certain embodiments 25° C., in certain embodiments 68° F., and in certain embodiments 77° F. Other methods known to those of skill in the crystallization arts, (e.g., solvent evaporation, drowning, chemical reaction, seeding with a small quantity of the desired crystal form, etc.) may also be employed to crystallize 3R)-4-{[(1S)-2-methyl-1-(2-methylpropanoyloxy)propoxy]carbonylamino}-3-(4-chlorophenyl)butanoic acid hemihydrate (1b).

Crystallization of (3R)-4-{[(1S)-2-methyl-1-(2-methylpropanoyloxy)propoxy]carbonylamino}-3-(4-chlorophenyl)butanoic acid hemihydrate (1b) from the solution affords crystalline (3R)-4-{[(1S)-2-methyl-1-(2-methylpropanoyloxy)propoxy]carbonylamino}-3-(4-chlorophenyl)butanoic acid hemihydrate (1b) as a white crystalline solid.

In certain embodiments, crystalline (3R)-4-{[(1S)-2-methyl-1-(2-methylpropanoyloxy)propoxy]carbonylamino}-3-(4-chlorophenyl)butanoic acid hemihydrate (1b) can be prepared by steps comprising providing a solution comprising 1-((2,5-dioxopyrrolidin-1-yl-oxycarbonyloxy)-2-methylpropyl-2-methylpropanoate (3) prepared as a racemic mixture, (R)-baclofen (2), water and methyl tert-butyl ether; and adjusting the temperature of the solution to provide crystalline (3R)-4-{[(1S)-2-methyl-1-(2-methylpropanoyloxy)propoxy]carbonylamino}-3-(4-chlorophenyl)butanoic acid hemihydrate (1b) and (3R)-4-{[(1R)-2-methyl-1-(2-methylpropanoyloxy)propoxy]carbonyl amino}-3-(4-chlorophenyl)butanoic acid (4).

In certain embodiments, crystalline (3R)-4-{[(1S)-2-methyl-1-(2-methylpropanoyloxy)propoxy]carbonylamino}-3-(4-chlorophenyl)butanoic acid hemihydrate (1b) can be prepared by steps comprising providing a solution comprising 1-((2,5-dioxopyrrolidin-1-yl-oxycarbonyloxy)-2-methylpropyl-2-methylpropanoate (3) prepared as a racemic mixture, (R)-baclofen (2), about 65% v/v water and about 35% v/v methyl tert-butyl ether; and adjusting the temperature of the solution to provide crystalline (3R)-4-{[(1S)-2-methyl-1-(2-methylpropanoyloxy)propoxy]carbonylamino}-3-(4-chlorophenyl)butanoic acid hemihydrate (1b) and (3R)-4-{[(1R)-2-methyl-1-(2-methylpropanoyloxy)propoxy]carbonylamino}-3-(4-chlorophenyl)butanoic acid (4).

In certain embodiments, crystalline (3R)-4-{[(1S)-2-methyl-1-(2-methylpropanoyloxy)propoxy]carbonylamino}-3-(4-chlorophenyl)butanoic acid hemihydrate (1b) can be prepared by steps comprising providing a first solution comprising 1-((2,5-dioxopyrrolidin-1-yl-oxycarbonyloxy)-2-methylpropyl-2-methylpropanoate (3) prepared as a racemic mixture, (R)-baclofen (2), about 65% v/v water and about 35% v/v methyl tert-butyl ether; increasing the temperature of the first solution to create a second solution comprising (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid (4); and decreasing the temperature of the second solution to provide crystalline (3R)-4-{[(1S)-2-methyl-1-(2-methylpropanoyloxy)propoxy]carbonylamino}-3-(4-chlorophenyl)butanoic acid hemihydrate (1b) and (3R)-4-{[(1R)-2-methyl-1-(2-methylpropanoyloxy)propoxy]carbonylamino}-3-(4-chlorophenyl)butanoic acid (4).

(3R)-4-{[(1R)-2-methyl-1-(2-methylpropanoyloxy)propoxy]carbonylamino}-3-(4-chlorophenyl)butanoic acid (4) is a diastereomer of (3R)-4-{[(1S)-2-methyl-1-(2-methylpropanoyloxy)propoxy]carbonylamino}-3-(4-chlorophenyl)butanoic acid. In certain embodiments, the solvent or combination of solvents is selected so that (3R)-4-{[(1R)-2-methyl-1-(2-methylpropanoyloxy)propoxy]carbonylamino}-3-(4-chlorophenyl)butanoic acid (4) remains in solution during crystallization of (3R)-4-{[(1S)-2-methyl-1-(2-methylpropanoyloxy)propoxy]carbonylamino}-3-(4-chlorophenyl)butanoic acid hemihydrate (1b). In this way, crystalline (3R)-4-{[(1S)-2-methyl-1-(2-methylpropanoyloxy)propoxy]carbonylamino}-3-(4-chlorophenyl)butanoic acid hemihydrate (1b) can be readily separated from the diastereomer (3R)-4-{[(1R)-2-methyl-1-(2-methylpropanoyloxy)propoxy]carbonylamino}-3-(4-chlorophenyl)butanoic acid (4) in a single crystallization step. Other methods known to those of skill in the crystallization arts, (e.g., high performance liquid chromatography, reverse-phase high performance liquid chromatography, extraction, distillation extraction, chromatography, the use of immobilized sorbents, etc.) may also be employed to separate crystalline (3R)-4-{[(1S)-2-methyl-1-(2-methylpropanoyloxy)propoxy]carbonylamino}-3-(4-chlorophenyl)butanoic acid hemihydrate (1b) from the diastereomer (3R)-4-{[(1R)-2-methyl-1-(2-methylpropanoyloxy)propoxy]carbonylamino}-3-(4-chlorophenyl)butanoic acid (4).

As used herein, the terms solution and suspension are used interchangeably and are meant to include embodiments in which a compound is in a solvent or solvent mixture regardless of solubility. A solvent combination can be such that a compound in solution exhibits temperature-dependent solubility. In general, solvent combinations in which a compound is soluble within a first temperature range, and poorly soluble within a second temperature range, can be used in the crystallization methods disclosed herein. Mixtures of a "good" solvent and an "anti-solvent" can also be used with temperature dependent solubilization, i.e., dissolving at elevated temperature and crystallizing at room temperature. Examples of suitable "good" solvents, i.e., solvents in which (3R)-4-{[(1S)-2-methyl-1-(2-methylpropanoyloxy)propoxy]carbonylamino}-3-(4-chlorophenyl)butanoic acid is soluble, include methanol, ethanol, isopropanol, acetone, methyl isobutyl ketone, tetrahydrofuran, 2-methyl tetrahydrofuran, 1,4-dioxane, 1,2-ethandiol, 1,2-propanediol, 2-methoxyethanol, 2-ethoxyethanol, and a mixture of any of the foregoing. Examples of suitable "anti-solvents", i.e., solvents in which (3R)-4-{[(1S)-2-methyl-1-(2-methylpropanoyloxy)propoxy]carbonylamino}-3-(4-chlorophenyl)butanoic acid exhibits poor solubility, include water, diethyl ether, diisopropyl ether, methyl t-butyl ether, toluene, chlorobenzene, alkanes such as pentane, hexane, heptane, octane, nonane, decane, undecane, dodecane, cis- or trans-decalin, cyclohexane, methylcyclohexane, and a mixture of any of the foregoing.

Therapeutic Uses

The high (R)-baclofen oral bioavailability following administration of compound (1) favors the efficacious use of compound (1) in oral dosage forms, including sustained-release oral dosage forms, and the use of such oral dosage forms for treating diseases such as spasticity and gastroesophageal reflux disease (van Herwaarden et al., *Aliment. Pharmacol. Ther.* 2002, 16(9), 1655-62; Ciccaglione and Marzio, *Gut* 2003, 52(4), 464-70; Andrews et al., U.S. Pat. No. 6,117,908; and Fara et al., International Publication No. WO 02/096404); in promoting alcohol abstinence in alcoholics (Gessa et al., International Publication No. WO 01/26638); in promoting smoking cessation (Gessa et al., International Publication No. WO 01/08675); in reducing addiction liability of narcotic agents (Robson et al., U.S. Pat. No. 4,126,684); in the treatment of emesis (Bountra et al., U.S. Pat. No. 5,719,185); as an anti-tussive for the treatment of cough (Kreutner et al., U.S. Pat. No. 5,006,560); as well as for treating movement disorders such as dystonia and hiccups; peripheral nerve disorders such as muscle stimulation disorders; spinal cord disorders such as spastic paraparesis; cranial nerve disorders such as glossopharyngeal neuralgia and trigeminal neuralgia; multiple sclerosis; and cerebral palsy.

The pharmacological activity of (R)-baclofen, (R)-4-amino-3-(4-chlorophenyl)butanoic acid, is believed to be effected through selective activation of $GABA_B$ receptors, resulting in neuronal hyperpolarization. $GABA_B$ receptors are located in laminae I-IV of the spinal cord, where primary sensory fibers end. $GABA_B$ receptors are G-protein coupled receptors that activate conductance by $K^+$-selective ion channels and can reduce currents mediated by $Ca^{2+}$ channels in certain neurons. Baclofen has a pre-synaptic inhibitory effect on the release of excitatory neurotransmitters and also acts postsynaptically to decrease motor neuron firing (see Bowery, *Trends Pharmacol. Sci.* 1989, 10, 401-407; and Misgeld et al., *Prog. Neurobiol.* 1995, 46, 423-462).

A principal pharmacological effect of baclofen in mammals is reduction of muscle tone and consequently the drug is frequently used in the treatment of spasticity. Spasticity is associated with damage to the corticospinal tract and is a common complication of neurological disease. Diseases and conditions in which spasticity may be a prominent symptom include cerebral palsy, multiple sclerosis, stroke, head and spinal cord injuries, traumatic brain injury, anoxia, and neurodegenerative diseases. Patients with spasticity complain of stiffness, involuntary spasm, and pain. These painful spasms may be spontaneous or triggered by a minor sensory stimulus, such as touching the patient.

Baclofen is also useful in controlling gastro-esophageal reflux disease (van Herwaarden et al., *Aliment. Pharmacol. Ther.* 2002, 16(9), 1655-62; Ciccaglione and Marzio, *Gut* 2003, 52(4), 464-70; Andrews et al., U.S. Pat. No. 6,117,908; and Fara et al., International Publication No. WO 02/096404); in promoting alcohol abstinence in alcoholics (Gessa et al., International Publication No. WO 01/26638); in promoting smoking cessation (Gessa et al., International Publication No. WO 01/08675); in reducing addiction liability of narcotic agents (Robson et al., U.S. Pat. No. 4,126,684); in the treatment of emesis (Bountra et al., U.S. Pat. No. 5,719,185); as an anti-tussive for the treatment of cough (Kreutner et al., U.S. Pat. No. 5,006,560); in treating neuropathic pain (see e.g., Fromm et al., Neurology 1981, 31(6), 683-7; and Ringel and Roy, *Ann Neurol* 1987, 21(5), 514-5); and in treating musculoskeletal pain (see e.g., Hering-Hanit, *Cephalalgia* 1999, 19(6), 589-591; Hering-Hanit and Gadoth, *Headache* 2000, 40(1), 48-51; Freitag, *CNS Drugs* 2003, 17(6), 373-81; Slonimski et al., *Reg Anesth Pain Med* 2004, 29(3), 269-76).

Accordingly, administering crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, both of which are the (R)-baclofen prodrugs, to a patient can be expected to be useful in treating diseases and disorders associated with the $GABA_B$ receptor and/or any of the diseases and disorders (R)-baclofen is known to treat.

The suitability of the (R)-baclofen prodrugs crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate in treating the above-listed diseases may be determined by methods described in the art (see, e.g., Bowery, *Trends Pharmacol. Sci.* 1989, 10, 401-407; Misgeld et al., *Prog. Neurobiol.* 1995, 46, 423-462; van Herwaarden et al., *Aliment. Pharmacol. Ther.* 2002, 16(9), 1655-62; Ciccaglione and Marzio, *Gut* 2003, 52(4), 464-470; Andrews et al., U.S. Pat. No. 6,117,908; Fara et al., International Publication No. WO 02/096404; Gessa et al., International Publication No. WO 01/26638; Gessa et al., International Publication No. WO 01/08675); Robson et al., U.S. Pat. No. 4,126,684; Bountra et al., U.S. Pat. No. 5,719, 185; and Kreutner et al., U.S. Pat. No. 5,006,560; Katz, *Am. J. Phys. Med. Rehabil.* 1988, 67(3), 108-16; Krach, *J. Child Neurol.* 2001, 16(1), 31-6; Bryans et al., International Publication No. WO 01/90052; Bryans et al., EP 1178034; Cundy et al., U.S. Application Publication No. 2002/0151529; Gallop et al., U.S. Application Publication No. 2003/0176398; Gallop et al., U.S. Application Publication No. 2003/0171303; Gallop et al., U.S. Application Publication No. 2004/0006132; and Raillard et al., U.S. Application Publication No. 2004/0014940).

A suitable dose of crystalline (3R)-4-{[(1S)-2-methyl-1-(2-methylpropanoyloxy)propoxy]carbonylamino}-3-(4-chlorophenyl)butanoic acid anhydrate and/or a suitable dose of crystalline (3R)-4-{[(1S)-2-methyl-1-(2-methylpropanoyloxy)propoxy]carbonylamino}-3-(4-chlorophenyl)butanoic acid hemihydrate to be administered to a patient in need of (R)-baclofen therapy may be estimated based on the mass equivalent of (R)-baclofen and the enhanced oral bioavailability of (R)-baclofen provided by crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate.

In various aspects, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, or pharmaceutical compositions comprising either of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, may be administered to a patient, such as a human, suffering from treating a disease or disorder chosen from spasticity, gastroesophageal reflux disease, emesis, cough, substance addiction and abuse, neuropathic pain and musculoskeletal pain.

Further, in certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, or pharmaceutical compositions comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, can be administered to a patient, such as a human, as a preventative measure against various diseases or disorders. Crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, or pharmaceutical compositions comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, may be administered as a preventative measure to a patient having a predisposition for spasticity, gastroesophageal reflux disease, emesis, cough, substance addiction and abuse, neuropathic pain and musculoskeletal pain. Accordingly, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, or pharmaceutical compositions comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, may be used for the prevention of one disease or disorder and concurrently for the treatment of another (e.g., prevention of spasticity while treating a narcotic addiction; prevention of neuropathic pain while treating gastroesophageal reflux disease).

Both crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate may be more efficacious than the parent drug molecule (i.e. baclofen) in treating spasticity, gastroesophageal reflux disease, emesis, cough, substance addiction and abuse, neuropathic pain and musculoskeletal pain because, when administered orally, the compound provides for sustained therapeutically effective blood concentrations of (±)-4-amino-3-(4-chlorophenyl)butanoic acid. It is believed that metabolites of both crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate are absorbed from the gastrointestinal lumen into the blood by a different mechanism than that by which baclofen and other known GABA analogs are absorbed. For example, pregabalin is believed to be actively transported across the gut wall by a carrier transporter localized in the human small intestine. In contrast, the compounds disclosed herein, and/or metabolites thereof, are believed to be absorbed across the gut wall along a greater portion of the gastrointestinal tract, including the colon.

Because metabolites of both crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate can be absorbed throughout the gastrointestinal tract, including the colon, both compounds can be advantageously formulated in sustained release oral formulations that provide for sustained release of one or both of the compounds over a period of hours into the gastrointestinal tract. The ability of both crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate to be used in sustained release oral dosage forms can facilitate therapeutic regimens having a reduced dosing frequency necessary to maintain a therapeutically effective baclofen concentration in the blood.

In certain embodiments, crystalline (3R)-4-{[(1S)-2-methyl-1-(2-methylpropanoyloxy)propoxy]carbonylamino}-3-(4-chlorophenyl)butanoic acid anhydrate, crystalline (3R)-4-{[(1S)-2-methyl-1-(2-methylpropanoyloxy)propoxy]carbonylamino}-3-(4-chlorophenyl)butanoic acid hemihydrate, combinations thereof, and/or pharmaceutical compositions thereof, can be administered to a patient for treating a disease or disorder selected from spasticity, gastroesophageal reflux disease, emesis, cough, substance addiction and abuse, neuropathic pain and musculoskeletal pain.

Spasticity

In certain embodiments, crystalline (3R)-4-{[(1S)-2-methyl-1-(2-methylpropanoyloxy)propoxy]carbonylamino}-3-(4-chlorophenyl)butanoic acid anhydrate can be administered to a patient to treat spasticity. In certain embodiments, crystalline (3R)-4-{[(1S)-2-methyl-1-(2-methylpropanoyloxy)propoxy]carbonylamino}-3-(4-chlorophenyl)butanoic acid hemihydrate can be administered to a patient to treat spasticity.

Spasticity is estimated to affect about 500,000 people in the United States and more than 12 million people worldwide. Spasticity is an involuntary, velocity-dependent, increased resistance to stretch. Spasticity is characterized by muscle hypertonia in which there is increased resistance to externally imposed movement with increasing speed of stretch (Lance et al., *Trans Am. Neurol. Assoc.* 1970, 95, 272-274; and Sanger et al., *Pediatrics* 2003, 111, e89-e97). Spasticity can be caused by lack of oxygen to the brain before, during, or after birth (cerebral palsy); physical trauma (brain or spinal cord injury); blockage of or bleeding from a blood vessel in the brain (stroke); certain metabolic diseases; adrenolekodystrophy; phenylketonuria; neurodegenerative diseases such as Parkinson's disease and amyotrophic lateral sclerosis; and neurological disorders such as multiple sclerosis. Spasticity is associated with damage to the corticospinal tract and is a common complication of neurological disease. Diseases and conditions in which spasticity may be a prominent symptom include cerebral palsy, multiple sclerosis, stroke, head and spinal cord injuries, traumatic brain injury, anoxia, and neurodegenerative diseases. Patients with spasticity complain of stiffness, involuntary spasm, and pain. These painful spasms may be spontaneous or triggered by a minor sensory stimulus, such as touching the patient.

Symptoms of spasticity can include hypertonia (increased muscle tone), clonus (a series of rapid muscle contractions), exaggerated deep tendon reflexes, muscle spasms, scissoring (involuntary crossing of the legs), deformities with fixed joints, stiffness, and/or fatigue caused by trying to force the limbs to move normally. Other complications include urinary tract infections, chronic constipation, fever or other systemic illnesses, and/or pressure sores. The degree of spasticity can vary from mild muscle stiffness to severe, painful, and uncontrollable muscle spasms. Spasticity may coexist with other conditions but is distinguished from rigidity (involuntary bidirectional non-velocity-dependent resistance to movement), clonus (self-sustaining oscillating movements secondary to hypertonicity), dystonia (involuntary sustained contractions resulting in twisting abnormal postures), athetoid movement (involuntary irregular confluent writhing movements), chorea (involuntary, abrupt, rapid, irregular, and unsustained movements), ballisms (involuntary flinging movements of the limbs or body), and tremor (involuntary rhythmic repetitive oscillations, not self-sustaining). Spasticity can lead to orthopedic deformity such as hip dislocation, contractures, or scoliosis; impairment of daily living activities such as dressing, bathing, and toileting; impairment of mobility such as inability to walk, roll, or sit; skin breakdown secondary to positioning difficulties and shearing pressure; pain or abnormal sensory feedback; poor weight gain secondary to high caloric expenditure; sleep disturbance; and/or depression that is secondary to lack of functional independence.

Treatment of spasticity includes physical and occupational therapy such as functional based therapies, rehabilitation, facilitation such as neurodevelopmental therapy, proprioceptive neuromuscular facilitation, and sensory integration; biofeedback: electrical stimulation; and orthoses. Oral medications useful in treating spasticity include baclofen, benzodiazepines such as diazepam, dantrolene sodium; imidazolines such as clonidine and tizanidine; and gabapentin. Intrathecal medications useful in treating spasticity include baclofen. Chemodenervation with local anesthetics such as lidocaine and xylocalne; type A botulinum toxin and type B botulinum toxin; phenol and alcohol injection can also be useful in treating spasticity. Surgical treatments useful in treating spasticity include neurosurgery such as selective dorsal rhizotomy; and orthopedic operations such as contracture release, tendon or muscle lengthening, tendon transfer, osteotomy, and arthrodesis.

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy] carbonylamino}-3-(4-chlorophenyl)butanoic acid hemihydrate for the treatment of spasticity can be assessed using animal models of spasticity and in clinically relevant studies of spasticity of different etiologies. Animal models of spasticity are known (see e.g., Eaton, *J Rehab Res Dev* 2003, 40(4), 41-54; Kakinohana et al., *Neuroscience* 2006, 141, 1569-1583; Ligresti et al., *British J Pharm* 2006, 147, 83-91; Zhang et al., *Chinese J Clin Rehab*, 2006, 10(38), 150-151; Hefferan et al., *Neuroscience Letters* 2006, 403, 195-200; and Li et al., *J Neurophysiol* 2004, 92, 2694-2703). For example, animal models of spasticity include: (a) the mutant spastic mouse (Chai et al., *Proc. Soc. Exptl. Biol. Med.* 1962, 109, 491); (b) the acute/chronic spinally transected rat and the acute decerebrate rat (see e.g., Wright and Rang, *Clin Orthop Relat Res* 1990, 253, 12-19; Shimizu et al., *J Pharmacol Sci* 2004, 96, 444-449; and Li et al., *J Neurophysiol* 2004, 92, 2694-2703); (c) primary observation Irwin Test in the rat (Irwin, *Psychopharmacologia* 1968, 13, 222-57); and d) Rotarod Test in the rat and mouse (Dunham et al., *J. Am. Pharm. Assoc.* 1957, 46, 208-09). Other animal models include spasticity induced in rats following transient spinal cord ischemia (Kakinohana et al., *Neuroscience* 2006, 141, 1569-1583; and Hefferan et al., *Neuroscience Letters* 2006, 403, 195-200), spasticity in mouse models of multiple sclerosis (Ligresti et al., *British J Pharmacol* 2006, 147, 83-91); and spasticity in rat models of cerebral palsy (Zhang et al., *Chinese J Clin Rehabilitation* 2006, 10(38), 150-151). The maximal electroshock seizure (MES) threshold test in rodents is sensitive for detecting potential anticonvulsant properties (Loscher and Schmidt, *Epilepsy Res* 1988, 2(3), 145-181). In this model, anticonvulsant agents elevate the threshold to electrically-induced seizures while proconvulsants lower the seizure threshold.

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy] carbonylamino}-3-(4-chlorophenyl)butanoic acid hemihydrate for treating spasticity may also be assessed in humans using double blind placebo-controlled clinical trials (see e.g., Priebe et al., Spinal Cord 1997, 35(3), 171-5; Gruenthal et al., *Spinal Cord* 1997, 35(10), 686-9; Tuszynski et al., *Spinal Cord* 2007, 45, 222-231 and Steeves et al., *Spinal Cord* 2007, 45, 206-221 for examples of the conduct and assessment of clinical trials for spasticity caused by spinal cord injury). Clinical trial outcome measures for spasticity include the Ashworth Scale, the modified Ashworth Scale, muscle stretch reflexes, presence of clonus and reflex response to noxious stimuli. Spasticity can be assessed using methods and procedures known in the art such as a combination of clinical examination, rating scales such as the Ashworth Scale, the modified Ashworth scale the spasm frequency scale and the reflex score, biomechanical studies such as the pendulum test, electrophysiologic studies including electromyography, and functional measurements such as the Fugl-Meyer Assessment of Sensorimotor Impairment scale. Other measures can be used to assess spasticity associated with a specific disorder such as the Multiple Sclerosis Spasticity Scale (Hobart et al., *Brain* 2006, 129(1), 224-234).

Gastroesophageal Reflux Disease

In certain embodiments, crystalline (3R)-4-{[(1S)-2-methyl-1-(2-methylpropanoyloxy)propoxy]carbonylamino}-3-(4-chlorophenyl)butanoic acid anhydrate can be administered to a patient to treat gastroesophageal reflux disease. In certain embodiments, crystalline (3R)-4-{[(1S)-2-methyl-1-(2-methylpropanoyloxy)propoxy]carbonylamino}-3-(4-chlorophenyl)butanoic acid hemihydrate can be administered to a patient to treat gastroesophageal reflux disease.

Gastroesophageal reflux disease (GERD) is defined as chronic symptoms or mucosal damage produced by abnormal reflux in the esophagus. Symptoms of GERD include heartburn, esophagitis, strictures, dysphagia, chronic chest pain, cough, hoarsness, voice changes, chronic ear ache, burning chest pains, nausea, and sinusitis.

Tonic contraction of the lower esophageal sphincter is the principal factor preventing the reflux of gastric contents into the esophagus. Transient lower esophageal sphincter relaxation (TLESR) is the major mechanism underlying reflux in normal subjects and patients with GERD. GABA$_B$ agonists such as R-baclofen have been shown to reduce TLESRs in humans (Lidums et al., *Gastroenterology* 2000, 118(1), 7-13; Vela et al., *Aliment Pharmacol Ther* 2003, 17(2), 243-51; Ciccaglione and Marzio, *Gut* 2003, 52(4), 464-70; and Zhang et al., *Gut* 2002, 50(1), 19-24). Reduction of the frequency of TLESRs by baclofen is believed to be due to inhibition of vagal afferents, information transfer between the nucleus tractus solitarious and dorsal motor nucleus of the vagus, and vagal efferent outflow (Hornby et al., *Gastroenterol Clin N Am* 2002, 31(4 Suppl), S11-S20).

More specifically, (3R)-4-{[(1S)-2-methyl-1-(2-methylpropanoyloxy)propoxy]carbonylamino}-3-(4-chlorophenyl)butanoic acid (1) has been shown to reduce reflux episodes in clinical trials (Castell et al., *Am J. Gastroenterology* 2006, 101(suppl 2)(52), S59 and poster presentation at American College of Gastroenterology 2006 Annual Meeting, Oct. 20-25, 2006, Las Vegas, Nev.; and Castell et al., *Gastroenterology* 2007, suppl. A, 486 and poster presentation at Digestive Disease Week Meeting, May 19-24, 2007, Washington D.C.).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating GERD may be assessed using animal models such as those described by Blackshaw et al., *Am. J. Physiol.* 1999, 277, G867-G874; Lehmann et al., *Gastroenterology* 1999, 117, 1147-1154; and Stakeberg and Lehmann, *Neurogastroenterol. Mot.* 1999, 11, 125-132; and in clinical trials.

Emesis

In certain embodiments, crystalline (3R)-4-{[(1S)-2-methyl-1-(2-methylpropanoyloxy)propoxy]carbonylamino}-3-(4-chlorophenyl)butanoic acid anhydrate can be administered to a patient to treat emesis. In certain embodiments, crystalline (3R)-4-{[(1S)-2-methyl-1-(2-methylpropanoyloxy)propoxy]carbonylamino}-3-(4-chlorophenyl)butanoic acid hemihydrate can be administered to a patient to treat emesis.

Nausea, vomiting, and retching are basic human protective reflexes against the absorption of toxins as well as responses to certain stimuli. Nausea is a subjectively unpleasant wave-like sensation in the back of the throat or epigastrium associated with pallor or flushing, tachycardia, and an awareness of the urge to vomit. Sweating, excess salivation, and a sensation of being cold or hot may also occur. Vomiting is characterized by contraction of the abdominal muscles, descent of the diaphragm, and opening of the gastric cardia, resulting in forceful expulsion of stomach contents from the mouth. Retching involves spasmodic contractions of the diaphragm and the muscles of the thorax and abdominal wall without expulsion of gastric contents. Emesis is used herein to refer to nausea, vomiting, and/or retching.

Baclofen has been shown to suppress the retching and vomiting induced by morphine, thereby indicating the involvement of the GABA$_B$ receptor in the emetic control pathway (Suzuki et al., *Neuropharmacology* 2005, 49(8), 1121-31). Baclofen has also been shown to antagonize emesis induced by nicotine and motion in animal models (Chan et al., *Eur J Pharmacology* 2007, 559(2-3), 196-201).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating emesis can be assessed using appropriate animal models and using clinical trials. For example, efficacy in treating emesis induced by chemotherapeutic agents can be determined based on effects indicative of emesis such as pica, gastric stasis, and reduced food intake in rats, mice, or ferrets (see, e.g., Liu et al., *Physiology & Behavior*, 2005, 85, 271-277; Endo et al., *Biogenic Amines*, 2004, 18(3-6), 419-434; and Malik et al., *Eur. J. Pharmacol*, 2007, 555, 164-173). In clinical trials, assessment instruments such as the Duke Descriptive Scale, Visual Analog Scales, Morrow Assessment of Nausea and Emesis, Rhodes Index of Nausea and Vomiting Form-2, and Functional Living Index Emesis can be used to measure efficacy (see, e.g., Rhodes et al., *CA Cancer J Clin*, 2001, 51, 232-248 and references therein). In general, adequately controlled, double blind placebo controlled trails may be used to evaluate efficacy in humans.

Cough

In certain embodiments, crystalline (3R)-4-{[(1S)-2-methyl-1-(2-methylpropanoyloxy)propoxy]carbonylamino}-3-(4-chlorophenyl)butanoic acid anhydrate can be administered to a patient to treat cough. In certain embodiments, crystalline (3R)-4-{[(1S)-2-methyl-1-(2-methylpropanoyloxy)propoxy]carbonylamino}-3-(4-chlorophenyl)butanoic acid hemihydrate can be administered to a patient to treat cough.

Cough reflex, elicited by activation of cough receptors located in the respiratory tract, clears inhaled irritants and foreign substances from the respiratory tract and, in conjunction with the mucociliary system, can expel excessive airway secretion produced under abnormal conditions from the respiratory tract. Cough can be caused by mild acuate upper respiratory tract infections, allergies, asthma, chronic obstructive pulmonary disease, lung cancer, gastroesophageal reflux disease, post-nasal drip, and heart or ear disorders. However, chronic non-productive cough having no identifiable cause accounts for a significant percent of patients presenting with cough. Chronic cough is associated with exacerbation of asthmatic symptoms, rib fractures, breathlessness, ruptured abdominal muscles, pneumothorax, syncope, second and third degree heart block, and loss of consciousness. Persistent and uncontrollable cough can lead to morbidity and severely impairs the quality of life of these patients.

Cough includes acute and chronic cough of any type, etiology, or pathogenesis, and in particular cough associated with laryngeal sensory neuropathy.

The anti-tussive effects of baclofen are well-known (see e.g., Dicpinigaitis and Dobkin, *Chest* 1997, 111(4), 996-9; Dicpinigaitis and Rauf, *Respiration* 1998, 65(1), 86-8; Dicpinigaitis et al., *J Clin Pharmacol* 1998, 38(4), 364-7; and Kreutner et al., U.S. Pat. No. 5,006,560 and International Publication No. WO 91/08740).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating cough can be assessed using appropriate animal models and using clinical trials. Animal models of cough are reviewed by Lewis et al., *Pulmonary Pharmacology & Therapeutics* 2007, 20, 325-333.

Substance Addiction or Abuse

In certain embodiments, crystalline (3R)-4-{[(1S)-2-methyl-1-(2-methylpropanoyloxy)propoxy]carbonylamino}-3-(4-chlorophenyl)butanoic acid anhydrate can be administered to a patient to treat substance addiction or abuse. In certain embodiments, crystalline (3R)-4-{[(1S)-2-methyl-1-(2-methylpropanoyloxy)propoxy]carbonylamino}-3-(4-chlorophenyl)butanoic acid hemihydrate can be administered to a patient to treat substance addiction or abuse.

In clinical trials, (R)-baclofen has been shown to be effective in treating cocaine addiction (Brebner et al., *Alcohol & Alcoholism* 2002, 37(5), 478-84; and Haney et al., *Neuropsychopharmacology* 2006, 31, 1814-21); methamphetamine dependence (Heinzerling et al., *Drug Alcohol Depend* 2006, 85(3), 177-84); opioid dependence (Assadi et al., *BMC Psychiatry* 2003, 3(16); and Ahmadi-Abhari et al., *J Clin Pharm Therapeutics* 2001, 26(1), 67-71); alcohol craving and intake (Addolorato et al., *Alcohol & Alcoholism* 2002, 37(5), 504-8; and Flannery et al., *Alcohol Clin Exp Res* 2004, 28(10), 1517-23); nicotine use (Markou et al., *Ann N.Y. Acad Sci* 2004, 1025, 491-503); and drug addiction generally (Cousins et al., *Drug Alcohol Dependence* 2002, 65(3), 209-20).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating substance addiction and abuse can be assessed using animal models and in clinical trials. Animal models of substance abuse disorders are known (see e.g., Fattore et al., *Alcohol & Alcoholism* 2002, 37(5), 495-498 (nicotine); Spano et al., *Neuropharmacology* 2007, 52, 1555-1562 (opiate addiction); and Maccioni et al., *Alcohol* 2005, 36, 161-168 (alcohol abuse)).

Neuropathic Pain

In certain embodiments, crystalline (3R)-4-{[(1S)-2-methyl-1-(2-methylpropanoyloxy)propoxy]carbonylamino}-3-(4-chlorophenyl)butanoic acid anhydrate can be administered to a patient to treat neuropathic pain. In certain embodiments, crystalline (3R)-4-{[(1S)-2-methyl-1-(2-methylpropanoyloxy)propoxy]carbonylamino}-3-(4-chlorophenyl)butanoic acid hemihydrate can be administered to a patient to treat neuropathic pain.

It is estimated that neuropathic pain affects over 6 million patients in the U.S. and Europe and over 26 million patients worldwide. Neuropathic pain involves an abnormal processing of sensory input usually occurring after direct injury or damage to nerve tissue. Neuropathic pain is a collection of disorders characterized by different etiologies including infection, inflammation, disease such as diabetes and multiple sclerosis, trauma or compression to major peripheral nerves, and chemical or irradiation-induced nerve damage (Jensen et al., *Eur J Pharmacol* 2001, 429, 1-11). Neuropathic pain typically persists long after tissue injury has resolved. Prodrugs of $GABA_B$ agonists provided by the present disclosure can be used to treat neuropathic pain. In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate can be used to treat neuropathic pain including, for example, post-herpetic neuralgia, peripheral neuropathy, trigeminal neuralgia, painful diabetic neuropathy, HIV-related neuropathic pain, cancer-related pain, and/or fibromyalgia.

The International Association for the Study of Neuropathic Pain defines neuropathic pain states as disorders that are characterized by lesions or dysfunction of the neural system(s) which, under normal conditions, transmit noxious information to the central nervous system. The mechanisms underlying neuropathic pain conditions are highly heterogeneous, however all types of neuropathic pain are presumed to involve nerve injury and certain common aberrations in somatosensory processing in the central and/or peripheral nervous system (Baron, *Nat Clin Pract Neurol* 2006, 2, 95-106; and Beggs and Salter, *Drug Dev Res* 2006, 67, 289-301). Potential causes of neuropathic pain include physical damage, infection, and chemical exposure. Neuropathic pain can be generally classified as a focal/multifocal lesion of the peripheral nervous system, e.g., post-herpetic neuralgia, a generalized lesion of the peripheral nervous system, painful diabetic neuropathy, HIV-related neuropathic pain, a lesion of the central nervous system, or a more complex neuropathic disorder. Peripheral neuropathic pain can arise as a consequence of trauma and surgery related nerve injury, e.g., brachial plexus injury; entrapment neuropathies such as lumbar disc compression, carpal tunnel syndrome; disease-related neuropathies, e.g., diabetes and HIV-AIDS; radiculopathy; complex regional pain syndrome; and/or tumor growth leading to nerve compression or infiltration. Central neuropathic pain can be the result of stroke, multiple sclerosis, post-ischemic myelopathy; post-herpetic neuralgia; and/or post-traumatic spinal cord injury.

An essential part of neuropathic pain is a partial or complete loss of afferent sensory function and the paradoxical presence of certain hyperphenomena in the painful area. The nerve tissue lesion may be found in the brain, spinal cord, or the peripheral nervous system. Symptoms vary depending on the condition and can manifest as hyperalgesia (the lowering of pain threshold and an increased response to noxious stimuli), allodynia (the evocation of pain by non-noxious stimuli such as cold, warmth, or touch), hyperpathia (an explosive pain response that is suddenly evoked from cutaneous areas with increased sensory detection threshold when the stimulus intensity exceeds sensory threshold), paroxysms (a type of evoked pain characterized by shooting, electric, shock-like or stabbing pain that occur spontaneously, or following stimulation by an innocuous tactile stimulus or by a blunt pressure), paraesthesia (abnormal but non-painful sensations, which can be spontaneous or evoked, often described as pins and needles), dysesthesia (abnormal unpleasant but not necessarily painful sensation, which can be spontaneous or provoked by external stimuli), referred pain and abnormal pain radiation (abnormal spread of pain), and wind-up like pain and after sensations (the persistence of pain long after termination of a painful stimulus).

Patients with neuropathic pain typically describe burning, lancinating, stabbing, cramping, aching, and sometimes vice-like pain. The pain can be paroxysmal or constant. Pathological changes to the peripheral nerve(s), spinal cord, and brain have been implicated in the induction and maintenance of chronic pain. Patients suffering from neuropathic pain typically endure chronic, debilitating episodes that are refractory to current pharmacotherapies and profoundly affect their quality of life. Currently available treatments for neuropathic pain, including tricyclic antidepressants and gabapentin, typically show limited efficacy in the majority of patients (Sindrup and Jensen, *Pain* 1999, 83, 389-400).

There are several types of neuropathic pain. A classification that relates to the type of damage or related pathophysiology causing a painful neuropathy includes neuropathies associated with mechanical nerve injury such as carpal tunnel syndrome, vertebral disk herniation, entrapment neuropathies, ulnar neuropathy, and neurogenetic thoracic outlet syndrome; metabolic disease associated neuropathies such as diabetic polyneuropathy; neuropathies associated with neurotropic viral disease such as herpes zoster and human immunodeficiency virus disease; neuropathies associated with neurotoxicity such as chemotherapy of cancer or tuberculosis, radiation therapy, drug-induced neuropathy, and alcoholic neuropathy; neuropathies associated with inflammatory and/or immunologic mechanisms such as multiple sclerosis, anti-sulfatide antibody neuropathies, neuropathy associated with monoclonal gammopathy, Sjogren's disease, lupus, vasculitic neuropathy, polyclonal inflammatory neuropathies, Guillain-Barre syndrome, chronic inflammatory demyelinating neuropathy, multifocal motor neuropathy, paraneoplastic autonomic neuropathy, ganglinoic acetylcholine receptor antibody autonomic neuropathy, Lambert-Eaton myasthenic syndrome and myasthenia gravis; neuropathies associated with nervous system focal ischemia such as thalamic syndrome (anesthesia dolorosa); neuropathies associated with multiple neurotransmitter system dysfunction such as complex regional pain syndrome; neuropathies associated with chronic/neuropathic pain such as osteoarthritis, low back pain, fibromyalgia, cancer bone pain, chronic stump pain, phantom limb pain, and paraneoplastic neuropathies; toxic neuropathies (e.g., exposure to chemicals such as exposure to acrylamide, 3-chlorophene, carbamates, carbon disulfide, ethylene oxide, n-hexane, methyl n-butylketone, methyl bromide, organophosphates, polychlorinated biphenyls, pyriminil, trichlorethylene, or dichloroacetylene), focal traumatic neuropathies, phantom and stump pain, monoradiculopathy, and trigeminal neuralgia; and central neuropathies including ischemic cerebrovascular injury (stroke), multiple sclerosis, spinal cord injury, Parkinson's disease, amyotrophic lateral sclerosis, syringomyelia, neoplasms, arachnoiditis, and post-operative pain; mixed neuropathies such as diabetic neuropathies (including symmetric polyneuropathies such as sensory or sensorimotor polyneuropathy, selective small-fiber polyneuropathy, and autonomic neuropathy; focal and multifocal neuropathies such as cranial neuropathy, limb mononeuropathy, trunk mononeuropathy, mononeuropathy multiplex, and asymmetric lower limb motor neuropathy) and sympathetically maintained pain. Other neuropathies include focal neuropathy; glosopharyngeal neuralgia; ischemic pain; trigeminal neuralgia; atypical facial pain associated with Fabry's disease, Celiac disease, hereditary sensory neuropathy, or B12-deficiency; mono-neuropathies; polyneuropathies; hereditary peripheral neuropathies such as Carcot-Marie-Tooth disease, Refsum's disease, Strumpell-Lorrain disease, and retinitis pigmentosa; acute polyradiculoneuropathy; and chronic polyradiculoneuropathy. Paraneoplastic neuropathies include paraneoplastic subacute sensory neuropathy, paraneoplastic motor neuron disease, paraneoplastic neuromyotonia, paraneoplastic demyelinating neuropathies, paraneoplastic vasculitic neuropathy, and paraneoplastic autonomic insufficiency. Prodrugs of $GABA_B$ agonists, such as crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, can be used to treat any of the foregoing types of neuropathic pain. In certain embodiments, the neuropathic pain is chosen from post-herpetic neuralgia, peripheral neuropathy, trigeminal neuralgia, painful diabetic neuropathy, HIV-related neuropathic pain, cancer-related pain, and fibromyalgia. In certain embodiments, the neuropathic pain is chosen from post-herpetic neuralgia and trigeminal neuralgia.

The $GABA_B$ agonist (R)-baclofen has long been known to have antinociceptive activity in models of acute pain and recent studies have shown that baclofen inhibits allodynia and hyperalgesia in the chronic constriction injury and spinal nerve ligation models of persistent neuropathic pain at doses lower than those required to produce sedation and impairment of motor activity (see e.g., Hwang and Yaksh, Pain 1997, 70(1), 15-22; Smith et al., Neruopharmacology 1994, 33(9), 1103-8; Patel et al., Pain 2001, 90(3), 217-26; Balerio and Rubio, Pharmacol Res 2002, 46(3), 281-6; and Reis and Duarte, Br J Pharmacol 2006, 149(6), 733-9).

In clinical studies, intrathecal baclofen administration has been shown to be effective in treating neuropathic pain associated with spinal-cord injury and multiple sclerosis (Herman et al., Clin J Pain 1992, 8(4), 338-45), painful extremity paresthesias (Gatscher et al., Acta Neurochir Suppl 2002, 79, 75-76), sympathetically maintained pain (Van Hilten et al., N Engl J Med 2000, 343(9), 625-30; Becker et al., J Clin Neurosci 2000, 7(4), 316-9; and Zuniga et al., Reg Anesth Pain Med 2002, 27(1), 90-3). $GABA_B$ agonists such as baclofen have also been shown to be effective in trigeminal, gloospharyngeal, vagoglossopharyngeal, and ophthalmic-postherpetic neuralgias (Fromm et al., Neurology 1981, 31(6), 683-7; and Ringel and Roy, Ann Neurol 1987, 21(5), 514-5); and in patients with diabetic neuropathy (Anghinah et al., Muscle Nerve 1994, 17(8), 958-59). Doses of baclofen from about 50 mg/day to about 60 mg/day have been shown to be effective in treating trigeminal neuralgia (Fromm et al., Ann Neurol 1984, 15(3), 240-4).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating one or more types of neuropathic pain can be assessed in animal models of neuropathic pain and in clinical trials (see e.g., Beggs and Salter, Drug Dev Res 2006, 67, 829-301). Useful animal models of neuropathic pain include peripheral nerve injury by ligation or transection including dorsal rhizotomy (Lombard et al., Pain 1979, 6(2), 163-174); spinal nerve ligation (Kim and Chung, Pain 1992, 50, 355-363; and Hwang and Yaksh, Pain 1997, 70(1), 15-22); sciatic nerve transaction (Wall et al., Pain 1979, 7, 103-111); sciatic nerve cuff (Mosconi and Kruger, Pain 1996, 64, 37-57); partial nerve ligation (Seltzer et al., Pain 1990, 43, 205-218); chronic constriction (Bennett and Xie, Pain 1988, 33, 87-107); rat spinal cord ischemia model (Hao et al., Pain 1991, 45, 175-185; and von Heijne et al., Eur J Pain 2001, 5, 1-10); and spared nerve injury (Decosterd and Woolf, Pain 2000, 87, 149-158). Other animal models of neuropathies involving immune system activation and metabolic and chemically induced neuropathies include sciatic cyroneurolysis (DeLeo et al., Pain 1994, 56, 9-16); zymosan-induced neuritis (Chacur et al., Pain 2001, 94, 231-244); HIV gp120-induced pain model (Herzberg and Sagen, J Neuroimmunol 2001, 116, 29-39); photochemical ischemia (Kupers et al., Pain 1998, 76(1-2), 45-59); anti-ganglioside antibody (Slart et al., Pain 1997, 69, 119-125); streptozotocin-neuropathy (Fox et al., Pain 1999, 81, 307-316); DDI-induced myelinopathy (Joseph et al., Pain 2004, 107, 147-158); formalin phase 2 model of hyperalgesic pain (Dirig and Yaksy, J Pharmacology Exper Ther 1995, 275, 219-227); vincristine-induced pain model (Aley et al., Neuroscience 1996, 73, 259-265); paclitaxel-induced pain model (Cavaletti et al., Exp Neurol 1995, 133, 64-72); and cisplatin-induced pain model (Authier et al., Neurosci Lett 2000, 25, 2576-2585).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating various types of neuropathic pain can also be assessed in clinical trials using, for example, randomized double-blind placebo controlled methods. End points used in clinical trials for neuropathic pain can be determined using validated neuropathic pain criteria such as the Brief Pain Inventory, Categorical Scale, Gracety Pain Scale, Likert Scale, Neuropathic Pain Scale, Numerical Pain Scale, Short Form McGill Pain Questionnaire, Verbal Pain Scale, Visual Analog Scale (VAS), VAS Pain Intensity Scale, and/or VAS Pain Relief Scale.

Musculoskeletal Pain

In certain embodiments, crystalline (3R)-4-{[(1S)-2-methyl-1-(2-methylpropanoyloxy)propoxy]carbonylamino}-3-(4-chlorophenyl)butanoic acid anhydrate can be administered to a patient to treat musculoskeletal pain. In certain embodiments, crystalline (3R)-4-{[(1S)-2-methyl-1-(2-methylpropanoyloxy)propoxy]carbonylamino}-3-(4-chlorophenyl)butanoic acid hemihydrate can be administered to a patient to treat musculoskeletal pain.

Musculoskeletal conditions causing tenderness, musculoskeltal pain and muscle spasms include fibromyalgia, tension headaches, myofascial pain syndrome, facet joint pain, internal disk disruption, somatic dysfunction, spinal fractures, vertebral osteomyelitis, polymyalgia rheumatica, atlantoaxial instability, atlanto-occipital joint pain, osteoporotic vertebral compression fracture, Scheuermann's disease, spondyloysis, spondylolisthesis, kissing spines, sacroiliac joint pain, sacral stress fracture, coccygodynia, failed back syndrome, and mechanical low back or neck pain (see, e.g., Meleger and Krivickas, *Neurol Clin* 2007, 25, 419-438. In these conditions, muscle spasm is related to local factors involving the affected muscle groups without the increased tone or reflex characteristic of spasticity. Muscle, tendon, ligament, intervertebral disc, articular cartilage, and bone can be involved in musculoskeletal pain. Disorders that can produce neck and back pain include muscle strain, ligament sprain, myofascial pain, fibromyalgia, facet joint pain, internal disc disruption, somatic dysfunction, spinal fracture, verterbral osteomyelitis, and polymyalgia rheumatica, atlantoaxial instability and atlanto-occipital joint pain. (see e.g., Meleger and Krivickas, *Neurological Clinics* 2007, 25(2), 419-438).

Studies have shown that $GABA_B$ agonists can be effective in treating muscular pain and/or spasms associated with peripheral musculoskeletal conditions. Baclofen has been shown to be effective in treating migraine (Hering-Hanit, *Cephalalgia* 1999, 19(6), 589-91; and Hering-Hanit and Gadoth, *Headache* 2000, 40(1), 48-51) and specifically in tension-type headaches (Freitag, *CNS Drugs* 2003, 17(6), 373-81); and in low-back pain and radiculopathy (Slonimski et al., *Reg Anesth Pain Med* 2004, 29(3), 269-76; Dapas et al., *Spine* 1985, 10(4), 345-9; and Raphael et al., *BMC Musculoskeletal Disorders* 2002, 3(17).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating one or more types of musculoskeletal pain can be assessed in animal models of neuropathic pain and in clinical trials. For example, Kehl et al. disclose an animal model of muscle hyperplasia that employs intramuscular injection of carrageenan as useful for assessing the mechanisms and management of musculoskeletal pain (Kehl et al., *Pain* 2000, 85, 333-343).

Low back pain generally occurs in the lumbar region of the back in the location of lumbar vertebrae L1-L5. Pain in the lower back can be caused by a sprain, strain, or spasm to one of the muscles, ligaments, facet joints, and/or sacroiliac joints in the back; spinal sprain or overcompression; or disc rupture or bulge. Low back pain may also reflect nerve or muscle irritation or bone lesions. Most low back pain follows injury or trauma to the back, but pain may also be caused by degenerative conditions such as arthritis or disc disease, osteoporosis, or other bone diseases, viral infections, irritation to joints and discs, or congenital abnormalities in the spine. Obesity, smoking, weight gain during pregnancy, stress, poor physical condition, posture inappropriate for the activity being performed, and poor sleeping position also may contribute to low back pain. Additionally, scar tissue created when the injured back heals itself does not have the strength or flexibility of normal tissue. Buildup of scar tissue from repeated injuries eventually weakens the back and can lead to more serious injury. Occasionally, low back pain may indicate a more serious medical problem. Pain accompanied by fever or loss of bowel or bladder control, pain when coughing, and progressive weakness in the legs may indicate a pinched nerve or other serious condition. People with diabetes may have severe back pain or pain radiating down the leg related to neuropathy. Low back pain can be caused by bulging disc(s) (e.g., protruding, herniated, or ruptured disc), sciatica, spinal degeneration, spinal stenosis, osteoporosis, osteoarthritis, compression fractures, skeletal irregularities, fibromyalgia, spondylolysis and/or spondylolisthesis. Less common spinal conditions that can cause low back pain include ankylosing spondylitis, bacterial infections, osteomyelitis, spinal tumors, Paget's disease, and Scheuermann's disease. Clinical results suggest that $GABA_B$ agonists such as baclofen can be effective in treating low back pain (Dapas et al., *Spine* 1985, 10(4), 345-9; and Raphael et al., *BMC Musculoskeletal Disorders* 2002, 3(17). For example, doses of baclofen from about 20 mg/day to about 80/mg day have been shown to be effective in treating acute low back pain (Dapas et al., *Spine* 1985, 10(4), 345-9).

In certain embodiments, methods of treating low back pain provided by the present disclosure comprises treating disorders, conditions, and/or symptoms associated with low back pain such as muscle spasms. Symptoms of low back pain can depend on the cause. For example, symptoms of back sprain or back strain include muscle spasms, cramping, stiffness, and pain centered in the back and buttocks. Symptoms of nerve-root pressure include leg pain, also referred to as sciatica, and nerve-related manifestations such as tingling, numbness, or weakness in one leg or in the foot, lower leg, or both legs. Symptoms of arthritis of the spine include pain and stiffness that are worse in the back and hip.

Fibromyalgia is a condition characterized by aching and pain in muscles, tendons and joints all over the body, but especially along the spine. The body also is tender to touch in specific areas referred to as tender or trigger points. Other symptoms of fibromyalgia include sleep disturbance, depression, daytime tiredness, headaches, alternating diarrhea and constipation, numbness and tingling in the hands and feet, feelings of weakness, memory difficulties, and dizziness. Although the etiology of fibromyalgia is not known, stress, disordered sleep patterns, abnormal production of pain-related chemicals in the nervous system, and/or low levels of growth hormone are believed to contribute to the onset of fibromyalgia.

Fibromyalgia usually occurs in people between 20 and 60 years of age and is estimated to affect 3.4% of women and 0.5% of men. The incidence of juvenile primary fibromyalgia in school age girls is estimated to be about 1.2%.

Current treatment of fibromyalgia is based on symptoms, with the goals of alleviating pain, restoring sleep, and improving general quality of life. Several nonpharmacologic treatments include exercise, education, behavioral therapy and physical therapy. Pharmacologic treatments include tricyclic compounds, serotonin reuptake inhibitors, analgesics, muscle relaxants, and acetylcholine esterase inhibitors. There is evidence suggesting that $GABA_B$ agonists such as baclofen may be useful in improving fibromyalgia symptoms (Taylor-Gjevre and Gjevre, *Lupus* 2005, 14(6), 486-8).

The efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate for treating fibromyalgia may be assessed using animal models of fibromyalgia and in clinical results (see e.g., Dooley et al., U.S. Patent Application Publication Nos. 2004/0180959 and 2004/0138305; Crofford et al., *Arthritis & Rheumatism* 2005, 52, 4, 1264-1273; Eaton, *J Rehabilitation Research and Development* 2003, 40(4), 41S-54S; Guay, *Am J Geriatr Pharmacother* 2005, 3, 274-287; Freynhagen et al., *Pain* 2005, 115, 254-263; Backonja et al., *Clin Ther.* 2003, 25, 81-104; Gidal et al., *Am J Manag Care.* 2006, 12, S269-S278; and Argoff, *JAOA,* 2002, Suppl. 3, 102(9), S21-S26). In particular, animal models of neuropathic pain or clinically relevant studies of different types of neuropathic pain have been found useful in assessing therapeutic activity for treating fibromyalgia, such as are disclosed, for example, in Bennett and Xie, *Pain* 1988, 33, 87-107; Chaplan et al., *J. Neurosci. Meth.* 1994, 53, 55-63; Fox et al., *Pain* 2003, 105, 355-362; Milligan et al., *Brain Res.* 2000, 861, 105-116; De Vry et al., *Eur. J. Pharmacol.* 2004, 491, 137-148; and Polomano et al., *Pain* 2001, 94, 293-304.

Modes of Administration

Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, may be advantageously used in human medicine. Additionally, crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may be advantageously used in human medicine. As disclosed herein, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, are useful for the treatment of spasticity, gastroesophageal reflux disease, emesis, cough, substance addiction and abuse, neuropathic pain and musculoskeletal pain.

When used to treat the above diseases, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may be administered or applied singly, or in combination with other agents. Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may also be administered or applied singly or in combination with other pharmaceutically active agents, including other GABA analogs.

Methods of treatment include administering to a patient in need of such treatment a therapeutically effective amount of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or administering to a patient in need of such treatment a therapeutically effective amount of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof. The patient may be an animal, such as a mammal, for example, a human.

Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be administered orally. Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may also be administered by any other convenient route, for example, by infusion or bolus injection, or by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or that can be used to administer crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes or skin.

In certain embodiments, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may be delivered via sustained release systems, such as an oral sustained release system.

Both crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, exhibit enhanced bioavailability as (R)-baclofen compared to the bioavailability of (R)-baclofen when administered in an equivalent dosage form of R-baclofen and/or racemate. The enhanced bioavailability of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, is believed to be due the efficient absorption of crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate throughout the gastrointestinal tract, including the colon, via passive and/or active transport mechanisms.

Both crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, provide (R)-baclofen upon in vivo administration to a patient. Crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, or a metabolite thereof, may be absorbed into the systemic circulation from the gastrointestinal tract either by passive diffusion, active transport or by both passive and active processes.

Following administration to a patient, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, provide (R)-baclofen in the systemic circulation of a patient. Crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be absorbed from the gastrointestinal tract and enter the systemic circulation where the promoiety is cleaved to release (R)-baclofen.

When administered to a patient, for example, by a patient swallowing a dosage form comprising the compounds disclosed herein, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate provide a sustained therapeutically effective concentration of (R)-baclofen in the blood of a patient during a continuous period of time. In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may provide a concentration of (R)-baclofen in the blood of a patient that is greater than a minimum therapeutically effective concentration and less than a minimum adverse concentration of (R)-baclofen in the blood of the patient. In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate provide a therapeutically effective concentration of (R)-baclofen in the blood of a patient for a continuous period of time without exceeding the minimum adverse concentration of (R)-baclofen. In certain embodiments, the concentration of (R)-baclofen in the blood of a patient does not exceed a minimum adverse concentration at any time after crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is administered to a patient.

The promoiety of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be cleaved either chemically and/or enzymatically. One or more enzymes present in the stomach, intestinal lumen, intestinal tissue, blood, liver, brain or any other tissue of a mammal may cleave the promoiety of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate. The promoiety of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). When the promoiety of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is cleaved prior to absorption by the gastrointestinal tract, baclofen may be absorbed into the systemic circulation conventionally (e.g., mediated, in part, via the large neutral amino acid transporter located in the small intestine). When the promoiety of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is cleaved after absorption by the gastrointestinal tract, these baclofen prodrugs may be absorbed into the systemic circulation either by passive diffusion, active transport, or by both passive and active processes.

When the promoiety of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is cleaved after absorption by the gastrointestinal tract, these baclofen prodrugs may be absorbed into the systemic circulation from the large intestine. When absorbed by the large intestine, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be advantageously administered as a sustained release system. In certain embodiments, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be delivered by oral sustained release administration. When administered using a sustained release formulation, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be administered once per day, twice per day, or in some embodiments more than twice per day.

Crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate can provide a therapeutically effective concentration of (R)-baclofen in the blood of a patient for a continuous period of time while reducing or eliminating adverse drug effects associated with high blood concentrations of (R)-baclofen, e.g., at concentrations above the minimum adverse concentration, that are observed following dosing of (R)-baclofen itself. The high bioavailability of (R)-baclofen that is achievable by administering crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may facilitate the use of lower mass equivalents of (R)-baclofen in a dose to achieve a sustained therapeutically effective concentration of (R)-baclofen in the blood of a patient, as compared to the amount of (R)-baclofen in a dosage form comprising (R)-baclofen itself.

In certain embodiments, administration of a sustained release dosage form comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate can provide a therapeutically effective concentration of (R)-4-amino-3-(4-chlorophenyl)butanoic acid in the blood plasma of a patient for a time period of at least about 4 hours after administration of the dosage form, in certain embodiments for a time period of at least about 8 hours, in certain embodiments for a time period of at least about 12 hours, in certain embodiments for a time period of at least about 16 hours, in certain embodiments for a time period of at least about 20 hours, and in certain embodiments, for a time period of at least about 24 hours.

In certain embodiments, the concentration of (R)-baclofen in the blood of a patient will not exceed a minimum adverse concentration at any time after crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is administered to the patient. For example, the concentration of (R)-baclofen in the blood of a patient will not reach a concentration that causes adverse events in the patient. A therapeutically effective concentration of (R)-baclofen in the blood of a patient may range from about 50 ng/mL to about 1,000 ng/mL, and in certain embodiments, from about 100 ng/mL to about 500 ng/mL. The pharmacokinetic profile of the blood (R)-baclofen concentration achievable upon administration of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate to a patient can be characterized by a lower $C_{max}/C_{12}$ ratio, and a lower $C_{max}/$dose, as compared to formulations comprising (R)-baclofen itself that provide a similar (R)-baclofen blood $AUC_{inf}$.

Pharmaceutical Compositions

Pharmaceutical compositions provided by the present disclosure contain crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate together with a suitable amount of a pharmaceutically acceptable vehicle so as to provide a form for proper oral administration to a patient. In certain embodiments, pharmaceutical compositions provided by the present disclosure contain a therapeutically effective amount of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate together with a suitable amount of a pharmaceutically acceptable vehicle so as to provide a form for proper oral administration to a patient. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. Pharmaceutical compositions provided by the present disclosure may also contain minor amounts of wetting or emulsifying agents or pH buffering agents. In addition, auxiliary, stabilizing, thickening, lubricating and coloring agents may be used.

Pharmaceutical compositions comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be manufactured by means of mixing, dissolving, granulating, dragee-making, levigating, emulsifying, encapsulating, entrapping, lyophilizing, or other process known to those skilled in the art of pharmaceutical formulation. Pharmaceutical compositions may be formulated using one or more pharmaceutically acceptable vehicles that facilitate processing crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate into oral dosage formulations, such as sustained release oral dosage formulations.

Pharmaceutical compositions provided by the present disclosure can take the form of solutions, aqueous or oily suspensions, emulsion, tablets, pills, pellets, capsules, capsules containing liquids, granules, powders, sustained-release formulations, suppositories, emulsions, syrups, elixirs or any other form suitable for oral administration. Orally administered pharmaceutical compositions may contain one or more optional agents, for example, sweetening agents such as fructose, aspartame or saccharin, flavoring agents such as peppermint, oil of wintergreen or cherry coloring agents and preserving agents, to provide a pharmaceutical palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administering the compounds and compositions disclosed herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions can include pharmaceutically acceptable vehicles such as mannitol, lactose, starch, magnesium stearate, sodium saccharine, cellulose, magnesium carbonate, and the like.

For oral liquid preparations such as, for example, suspensions, elixirs and solutions, suitable vehicles include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

Crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be formulated in rectal or vaginal compositions such as suppositories or retention enemas, e.g., containing conventional suppository bases such as cocoa butter or other glycerides.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate can be formulated as a single active agent. In certain embodiments, crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate can be formulated as a mixture. In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate can be formulates as a mixture with one or more other baclofen prodrugs or salts thereof such as, for example, (3R)-4-{[(1S)-2-methyl-1-(2-methylpropanoyloxy)propoxy]carbonylamino}-3-(4-chlorophenyl)butanoic acid.

Kits

Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may be included in a kit that may be used to administer either compound, or both, to a patient for treating a disease. A kit can include a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate suitable for administration to a patient and instructions for administering the pharmaceutical composition to a patient. A kit can include one or more containers for containing one or more pharmaceutical compositions and may include divided containers such as a divided bottle or a divided foil packet. A container can be any appropriate shape or form made of a pharmaceutically acceptable material. A particular container can depend on the dosage form and the number of dosage forms provided. Instructions provided with a kit can include directions for administration and may include a memory aid. Instructions supplied with a kit may be printed and/or supplied, for example, as an electronic-readable medium, a video cassette, an audiotape, a flash memory device, or may be published on an internet web site or distributed to a patient as an electronic mail. A memory aid may be a written memory aid, which contains information and/or instructions for the physician, pharmacist, and/or patient to facilitate compliance with a dosing regimen. A memory aid may also be mechanical or electronic. When a therapeutic regimen includes administration of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate and at least one other therapeutic agent, a kit can include the at least one other therapeutic agent in the same or separate container as the crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating a disease chosen from spasticity, gastroesophageal reflux disease, emesis, cough, substance addiction and abuse, neuropathic pain and musculoskeletal pain. In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating a disease chosen from spasticity, gastroesophageal reflux disease, emesis, cough, substance addiction and abuse, neuropathic pain and musculoskeletal pain.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating spasticity. In certain embodiments, a kit comprises a pharmaceutical composition comprising crystalline (3R)-4-{[(1S)-2-methyl-1-(2-methylpropanoyloxy)

propoxy]carbonylamino}-3-(4-chlorophenyl)butanoic acid hemihydrate and instructions for administering the pharmaceutical composition to a patient in need thereof for treating spasticity.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating gastroesophageal reflux disease. In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating gastroesophageal reflux disease.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating substance addiction or abuse. In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating substance addiction or abuse.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating cough. In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating cough.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating emesis. In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating emesis.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating neuropathic pain. In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating neuropathic pain.

In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate and instructions for administering the pharmaceutical composition to a patient in need thereof for treating musculoskeletal pain. In certain embodiments, a kit comprises a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate and instructions for administering the pharmaceutical composition to a patient in need thereof for treating musculoskeletal pain.

Dose

Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can generally be used in an amount that is effective to achieve the intended purpose, such as to treat a disease or disorder selected from spasticity, gastroesophageal reflux disease, emesis, cough, substance addiction and abuse, neuropathic pain and/or musculoskeletal pain. Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, can be administered in a therapeutically effective amount. Crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be administered in a therapeutically effective amount.

The amount of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or the amount of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, that will be effective in the treatment of a particular disease or disorder will depend on the nature of the disorder or condition, and can be determined by standard clinical techniques known in the art as previously described. In addition, in vitro or in vivo assays may optionally be employed to help identify optimal dosage ranges. The amount of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or the amount of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, administered will depend on, among other factors, the subject being treated, the weight of the subject, the severity of the affliction, the manner of administration and the judgment of the prescribing physician.

A dose of crystalline (3R)-4-{[(1S)-2-methyl-1-(2-methylpropanoyloxy)propoxy]carbonylamino}-3-(4-chlorophenyl)butanoic acid anhydrate and/or a dose of crystalline (3R)-4-{[(1S)-2-methyl-1-(2-methylpropanoyloxy)propoxy]carbonylamino}-3-(4-chlorophenyl)butanoic acid hemihydrate can be adjusted to provide an equivalent molar quantity or mass equivalent dose of (R)-baclofen. A dose can comprise multiple dosage forms. Therapeutically effective doses of (R)-baclofen are generally from about 0.03 mg to about 1 mg per kilogram body weight per day. In certain embodiments, a daily dose can comprise a mass equivalent of (R)-baclofen ranging from about 1 mg to about 100 mg, in certain embodiments, from about 5 mg to about 80 mg, in certain embodiments, from about 5 mg to about 60 mg, and in certain embodiments, from about 10 mg to about 40 mg. In certain embodiments, a dose of crystalline (3R)-4-{[(1S)-2-methyl-1-(2-methylpropanoyloxy)propoxy]carbonylamino}-3-(4-chlorophenyl)butanoic acid anhydrate and/or a dose of crystalline (3R)-4-{[(1S)-2-methyl-1-(2-methylpropanoyloxy)propoxy]carbonylamino}-3-(4-chlorophenyl)butanoic acid hemihydrate is less than a dose that causes moderate sedation and impairment of motor activity in a patient. The dose of crystalline (3R)-4-{[(1S)-2-methyl-1-(2-methylpropanoyloxy)propoxy]carbonylamino}-3-(4-chlorophenyl)butanoic acid anhydrate and/or the dose of crystalline (3R)-4-{[(1S)-2-methyl-1-(2-methylpropanoyloxy)propoxy]carbonylamino}-3-(4-chlorophenyl)butanoic acid hemihydrate, and appropriate dosing intervals, can be selected to maintain a sustained therapeutically effective concentration of (R)-baclofen in the blood of a patient, and in certain embodiments, without exceeding a minimum adverse concentration.

A dose may be delivered in a pharmaceutical composition by a single administration or by multiple applications of one or more dosage forms. In certain embodiments, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be delivered by oral sustained release administration. A sustained release formulation comprising crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or a sustained release formulation comprising crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be administered once per day, twice per day and, in certain embodiments, at intervals greater than twice per day. Dosing may be repeated intermittently, may be provided alone or in combination with other drugs, and may continue as long as required for effective treatment of the disease or disorder. Dosing includes administering a dosage form to a mammal, such as a human, in a fed or fasted state.

Appropriate dosage ranges for treating a particular disease may be readily determined by methods known to the skilled artisan.

In certain embodiments, a dose or multiple doses of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or a dose or multiple doses of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can provide between about 10 mg/day and about 2,000 mg/day of (R)-baclofen, in certain embodiments between about 50 mg/day and about 1,000 mg/day of (R)-baclofen, and in certain embodiments, between about 100 mg/day and about 600 mg/day of (R)-baclofen.

In certain embodiments, a dose or multiple doses of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or a dose or multiple doses of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, is administered to a patient at a dose of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate ranging from about 5 mg to about 140 mg, and in certain embodiments, from about 10 mg to about 120 mg. In certain embodiments, the dose of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate administered is less than a dose of crystalline (3R)-4-{[(1S)-2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate that causes moderate sedation and impairment of motor activity in a patient.

A dosage regimen employing oral administration of a dose or multiple doses of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or a dose or multiple doses of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may be developed to maintain a concentration of (R)-baclofen in the blood of a patient that is greater than a minimum therapeutically effective concentration and less than a minimum adverse concentration for a prolonged period of time. In certain embodiments, a minimum therapeutically effective concentration of (R)-baclofen may range from about 1 ng/mL to about 200 ng/mL, and in certain embodiments, can range from about 10 ng/mL to about 100 ng/mL. In certain embodiments, a minimum adverse concentration can range from about 200 ng/mL to about 2,000 ng/mL, and in certain embodiments, can range from about 500 ng/mL to about 1,000 ng/mL. A minimum therapeutic concentration and a minimum adverse concentration will depend on a number of factors such as the disease being treated, the severity of the disease, the intended clinical outcome, the condition of the patient being treated, and so forth. An appropriate interval of dosing may depend, for example, on the amount of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate in the dosage form, the composition of the dosage form, the release characteristics of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate from the dosage form, the disease being treated, the condition of the patient, the potential adverse effects, and the judgment of the prescribing physician. Dosage regimens may include repeated administration of the same dosage form at each interval or different dosage forms at different intervals. For example, a twice-daily dosage regimen can include the administration of a first dosage form in the morning, and a second dosage form in the evening.

Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be assayed in vitro and in vivo, for the desired therapeutic or prophylactic activity, prior to use in humans. A therapeutically effective dose of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or a therapeutically effective dose of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can provide therapeutic benefit without causing substantial toxicity and/or adverse side effects. The toxicity and adverse side effects of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may be determined using standard pharmaceutical procedures and may be readily ascertained by the skilled artisan. The dose ratio between toxic and adverse side effects and therapeutic effect is the therapeutic index. A dose of crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or a dose of crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can provide a circulating concentration of (R)-baclofen that is within a therapeutically effective concentration with little or no toxicity or adverse side effects.

Combination Therapy

Dosage forms comprising crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and/or dosage forms comprising crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, may further comprise one or more pharmaceutically active compounds in addition to crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate. Such compounds may be provided to treat the same disease or a different disease than the disease being treated with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate.

In certain embodiments, crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, can be used in combination therapy with at least one other therapeutic agent. Crystalline (3R)-4-{[(1S)-2-methyl-1-(2-methylpropanoyloxy)propoxy]carbonylamino}-3-(4-chlorophenyl)butanoic acid anhydrate, or a pharmaceutical composition thereof, and the at least one other therapeutic agent can act additively or synergistically.

In certain embodiments, crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, can be used in combination therapy with at least one other therapeutic agent. Crystalline (3R)-4-{[(1S)-2-methyl-1-(2-methylpropanoyloxy)propoxy]carbonylamino}-3-(4-chlorophenyl)butanoic acid hemihydrate, or a pharmaceutical composition thereof, and the at least one other therapeutic agent can act additively or synergistically.

In certain embodiments, a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate can be administered concurrently with the administration of another therapeutic agent, which can be part of the same pharmaceutical composition as crystalline (3R)-4-{[(1S)-2-methyl-1-(2-methylpropanoyloxy)propoxy]carbonylamino}-3-(4-chlorophenyl)butanoic acid anhydrate, or the other therapeutic agent can be in a different pharmaceutical composition. In certain embodiments, a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate can be administered concurrently with the administration of another therapeutic agent, which can be part of the same pharmaceutical composition as crystalline (3R)-4-{[(1S)-2-methyl-1-(2-methylpropanoyloxy)propoxy]carbonylamino}-3-(4-chlorophenyl)butanoic acid hemihydrate, or the other therapeutic agent can be in a different pharmaceutical composition. In certain embodiments, a pharmaceutical composition comprising crystalline (3R)-4-{[(1S)-2-methyl-1-(2-methylpropanoyloxy)propoxy]carbonylamino}-3-(4-chlorophenyl)butanoic acid anhydrate, and/or a pharmaceutical composition comprising crystalline (3R)-4-{[(1S)-2-methyl-1-(2-methylpropanoyloxy)propoxy]carbonylamino}-3-(4-chlorophenyl)butanoic acid hemihydrate, can be administered prior to or subsequent to administration of another therapeutic agent.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered in combination with an amorphous form of (3R)-4-{[(1S)-2-methyl-1-(2-methylpropanoyloxy)propoxy]carbonylamino}-3-(4-chlorophenyl)butanoic acid; other crystalline form(s) of (3R)-4-{[(1S)-2-methyl-1-(2-methylpropanoyloxy)propoxy]carbonylamino}-3-(4-chlorophenyl)butanoic acid; baclofen; (R)-baclofen; or a combination of any of the foregoing.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be used in combination with at least one other therapeutic agent. In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient together with another compound for treating movement disorders such as spasticity, digestive disorders such as gastro-esophageal reflux disease and emesis, or addictive or abuse disorders such as nicotine addiction or abuse, alcohol addiction or abuse, narcotic addiction or abuse, cough, neuropathic pain, or musculoskeletal pain. In certain embodiments, the at least one other therapeutic agent may be a different (R)-baclofen prodrug. Crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate and the at least one other therapeutic agent may act additively or, in certain embodiments, synergistically.

Accordingly, methods provided by the present disclosure can further include, in addition to administering crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, administering one or more therapeutic agents effective for treating the same disease as, or a different disease than, the disease being treated by crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate. Methods provided by the present disclosure include administration of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate and one or more other therapeutic agents, provided, however, that the combined administration does not inhibit the therapeutic efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate and/or does not produce adverse combination effects.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered concurrently with the administration of another therapeutic agent, which may be part of the same dosage form as, or in a different dosage form than that comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate. Crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered prior to, or subsequent to, administration of another therapeutic agent. In certain embodiments of combination therapy, the combination therapy may comprise alternating between: administering crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate; and administering a composition comprising another therapeutic agent, e.g., to minimize adverse drug effects associated with a particular drug. When crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is administered concurrently with another therapeutic agent that may potentially produce an adverse drug effect including, but not limited to, toxicity, the other therapeutic agent may advantageously be administered at a dose that falls below the threshold at which the adverse drug reaction is elicited.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered with one or more substances to enhance, modulate and/or control release, bioavailability, therapeutic efficacy, therapeutic potency, stability, and the like of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate. For example, to enhance the therapeutic efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate or the metabolite of such compounds, (R)-baclofen, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be co-administered with, or a dosage form comprising crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may comprise, one or more active agents that act to increase the absorption or diffusion of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate or (R)-baclofen from the gastrointestinal tract to the systemic circulation, or to inhibit degradation of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate or (R)-baclofen in the blood of a patient. In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be co-administered with an active agent having pharmacological affects that enhance the therapeutic efficacy of crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2- methyl-1-(2-methylpropanoyloxy)propoxy]carbonylamino}-3-(4-chlorophenyl)butanoic acid hemihydrate.

Additionally, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be used in combination with other drugs that are themselves known to cause spasticity, gastroesophageal reflux disease, emesis, cough, substance addiction and abuse, neuropathic pain and/or musculoskeletal pain as an adverse effect, thereby preventing or reducing the occurrence of such adverse effects.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating a movement disorder such as spasticity in combination with a therapy or another therapeutic agent known or believed to be effective in treating a movement disorder such as spasticity. Examples of drugs for treating movement disorders such as spasticity and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include levodopa; mild sedatives such as benzodiazepines including alprazolam, chlordiazepoxide, clonazepam, clorazepate, diazepam, lorazepam, and oxazepam; muscle relaxants such as baclofen; anticholinergic drugs such as trihexyphenidyl and diphenhydramine; antipsychotics such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; and antidepressants such as amitriptyline.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating a gastrointestinal disorder such as gastro-esophageal reflux disease in combination with a therapy or another therapeutic agent known or believed to be effective in treating a gastrointestinal disorder such as gastro-esophageal reflux disease. Examples of drugs for treating gastrointestinal disorders such as gastro-esophageal reflux disease and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include $H_2$-receptor inhibitors such as cimetidine, famotidine, nizatidine, and ranitidine; proton pump inhibitors such as omeprazole, lansoprazole, pantoprazole, rabeprazole, and exomeprazole; and prokinetics such as cisparide, bethanechol, and metoclopramide.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating emesis in combination with a therapy or another therapeutic agent known or believed to be effective in treating emesis. Examples of drugs for treating emesis (nausea and vomiting) and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include benzamines such as metoclopramide; phenothiazines such as prochlorperazine, perphenazine, chlorpromazine, promethazine, and thiethylperazine; butyrophenones such as droperidol and haloperidol; dopamine 2 antagonists such as metoclorpamide; 5-$HT_3$ antagonists such as ondansetron, granisetron, dolasetron, palonosetron; NK-1 receptor antagonists such as aprepitant, corticosteroids such as dexamethazone; antihistamines such as diphenhydramine and hydroxyzine; cannabinoids such as dronabinol; and benzodiazepines such as lorazepam, midazolam, alprazolam, and olanzapine.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating alcohol addiction or abuse in combination with a therapy or another therapeutic agent known or believed to be effective in treating alcohol addiction or abuse. Examples of drugs for treating alcohol addiction or abuse and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include disulfuram, naltrexone, clonidine, methadone, 1-alpha-acetylmethadol, buprenorphine, and bupropion.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating narcotic addiction or abuse in combination with a therapy or another therapeutic agent known or believed to be effective in treating narcotic addiction or abuse. Examples of drugs for treating narcotic addiction or abuse and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include buprenorphine, tramadol, methadone, and naltrexone.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating nicotine addiction or abuse in combination with a therapy or another therapeutic agent known or believed to be effective in treating nicotine addiction or abuse. Examples of drugs for treating nicotine addiction or abuse and which may be administered in conjunction with crystalline (3R)-4-{[(1S)-2-methyl-1-(2-methylpropanoyloxy)propoxy]carbonylamino}-3-

(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include bupropion, clonidine, and nicotine.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating cough in combination with a therapy or another therapeutic agent known or believed to be effective in treating cough. Examples of drugs for treating cough and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include dextromethorphan, guaifenesin, hydrocodone, benzonatate, diphenhydramine, pseudoephedrine, acetaminophen, and carbinoxamine.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating neuropathic pain in combination with a therapy or another therapeutic agent known or believed to be effective in treating neuropathic pain. Examples of drugs useful for treating pain and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include opioid analgesics such as morphine, codeine, fentanyl, meperidine, methadone, propoxyphene, levorphanol, hydromorphone, oxycodone, oxymorphone, tramadol and pentazocine; nonopioid analgesics such as aspirin, ibuprofen, ketoprofen, naproxen, and acetaminophen; non-steroidal anti-inflammatory drugs such as aspirin, choline magnesium trisalicylate, diflunisal, salsalate, celecoxib, rofecoxib, valdecoxib, diclofenac, etodolac, fenoprofen, flubiprofen, ibuprofen, indomethacin, ketoprofen, ketorolac, meclofanamate, mefenamic acid, meloxicam, nabumetone, naproxen, oxaprozin, piroxicam, sulindac, and tometin; antiepileptics such as gabapentin, pregabalin, carbamazepine, phenyloin, lamotrigine, and topiramate; antidepressants such as duloxetine, amitriptyline, venlafaxine, nortryptyline, imipramine, and desipramine; local anesthetics such as lidocaine, and mexiletine; NMDA receptor antagonists such as dextropethorphan, memantine, and ketamine; N-type calcium-channel blockers such as ziconotide; vanilloid receptor-1 modulators such as capsaicin; cannabinoid receptor modulators such as sativex; neurokinin receptor antagonists such as lanepitant; other analgesics such as neurotropin; and other drugs such as desipramine, clonazepam, divalproex, oxcarbazepine, divalproex, butorphanol, valdecoxib, vicoprofen, pentazocine, propoxyhene, fenoprofen, piroxicam, indometnacin, hydroxyzine, buprenorphine, benzocaine, clonidine, flurbiprofen, meperidine, lacosamide, desvenlafaxine, and bicifadine.

In certain embodiments, a drug useful for treating neuropathic pain and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is chosen from propoxyphene, meperidine, hydromorphone, hydrocodone, morphine, codeine, 2-piperidinol-1-alkanol, eliprodil, ifenprodil, rofecoxib, celecoxib, salicylic acid, diclofenac, piroxicam indomethacin, ibuprofen, naproxen, gabapentin, carbemazepine, pregabalin, topiramate, valproic acid, sumatriptan, elitriptan, rizatriptan, zolmitriptan, naratriptan, flexeril, carisoprodol, robaxisal, norgesic, dantrium, diazepam, chlordiazepoxide, alprazolam, lorazepam, acetaminophen, nitrous oxide, halothane, lidocaine, etidocaine, ropivacaine, chloroprocaine, sarapin, bupivacaine, capsicin, desipramine, amitriptyline, doxepin, perphenazine, protriptyline, tranylcypromine, baclofen, clonidine, mexelitine, diphenhydramine, hydroxyzine, caffeine, prednisone, methyl-prednisone, decadron, sertraline, paroxetine, fluoxetine, tramadol, levodopa, dextromethorphan, substance P antagonists, and botulinum toxin.

In certain embodiments, a drug useful for treating neuropathic pain and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is chosen from a nicotine receptor partial agonist and an analgesic agent as disclosed by Coe et al., U.S. Patent Application Publication No. 2003/0133951; a 1-aryl-3-azabicyclo[3.1.0] hexane as disclosed by Lippa et al., U.S. Patent Application Publication No. 2007/00892939; and a nitro(cyano)vinylpiperazine compound as disclosed by Sun and Tafesse, U.S. Patent Application Publication No. 2007/0032500.

Non-pharmacological therapies for treating neuropathic pain and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include transcutaneous electrical nerve stimulation, percutaneous electrical nerve stimulation, and acupuncture.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating fibromyalgia in combination with a therapy or another therapeutic agent known or believed to be effective in treating fibromyalgia, or in certain embodiments, a disease, disorder, or condition associated with fibromyalgia. Drug therapy for fibromyalgia may be tailored to the severity and frequency of fibromyalgia episodes. For occasional episodes, acute treatment may be indicated. For fibromyalgia episodes occurring two or more times per month, or when attacks greatly impact the patient's daily life, chronic therapy on an ongoing basis may be appropriate.

Treatments for fibromyalgia that reduce the frequency of episodes and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include non-steroidal anti-inflammatory agents (NSAIDs), adrenergic beta-blockers, calcium channel blockers, tricyclic antidepressants, selective serotonin reuptake inhibitors, anticonvulsants, NMDA receptor antagonists, dopamine agonists, selective 5-HT$_3$ receptor antagonists, opioids, muscle relaxants, sedative hypnotics, and other therapy. Examples of NSAIDs useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include aspirin, ibuprofen, fenoprofen, flurbiprofen, ketoprofen, mefenamic acid, and naproxen. Examples of adrenergic beta-blockers useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include acebutolol, atenolol, imilol, metoprolol, nadolol, pindolol, propranolol, and timolol. Examples of calcium channel blockers useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include amlodipine, diltiazem, dotarizine, felodipine, flunarizine, nicardipine, nifedipine, nimodipine, nisoldipine, and verapamil. Examples of tricyclic antidepressants useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include amitriptyline, desipramine, doxepin, imipramine, nortriptyline, cyclobenzaprine, and protriptyline. Examples of selective serotonin reuptake inhibitors useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include fluoxetine, methysergide, nefazodone, paroxetine, sertraline, citalopram, and venlafaxine. Examples of other antidepressants useful for treating g fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include bupropion, nefazodone, norepinephrine, venlafaxine, duloxetine, and trazodone. Examples of anticonvulsants (antiepileptics) useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include divalproex sodium, felbamate, gabapentin, lamotrigine, levetiracetam, oxcarbazepine, tiagabine, topiramate, valproate, and zonisamide. Examples of NMDA receptor antagonists useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include dextromethorphan, magnesium, and ketamine. Examples of dopamine agonists useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include α-dihydroergocryptine. Examples of opioids useful for preventing fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate are tramadol, oxycodone, and methadone. An example of a muscle relaxant useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate is cyclobenzaprine. Examples of therapies useful for treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include exercise, interferon, growth hormone, hormone therapy, diet low in animal fat and high in fiber, and complementary therapies such as counseling/psychotherapy, relaxation training, progressive muscle relaxation, guided imagery, diaphragmatic breathing, biofeedback, acupuncture, and physical and massage therapy.

Acute fibromyalgia treatments intended to eliminate or reduce the severity of muscular/skeletal pain and any associated symptoms, and which may be administered in conjunction with crystalline (3R)-4-{[(1S)-2-methyl-1-(2-methylpropanoyloxy)propoxy]carbonylamino}-3-(4-chlorophenyl) butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate, include serotonin receptor agonists, such as triptans (5-hydroxytryptophan (5-HTP) agonists), for example, almotriptan, eletriptan, frovatriptan, naratriptan, rizatriptan, sumatriptan, and zolmitriptan; ergotamine-based compounds such as dihydroergotamine and ergotamine; antiemetics such as metoclopramide and prochlorperazine; and compounds that provide analgesic effects.

Other examples of drugs useful in treating fibromyalgia and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include acetaminophen-aspirin, caffeine, cyproheptadine, methysergide, valproic acid; NSAIDs such as diclofenac, flurbiprofen, ketaprofen, ketorolac, ibuprofen, indomethacin, meclofenamate, and naproxen sodium; opioids such as codeine, meperidine, and oxycodone; and glucocorticoids such as dexamethasone, prednisone, and methylprednisolone.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating musculoskeletal pain in combination with a therapy or another therapeutic agent known or believed to be effective in treating musculoskeletal pain. Examples of drugs useful for treating musculoskeletal pain and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include cyclobenzaprine, dantrolene, methocarbamol, orphenadrine, tizanidrine, metaxalone, carisoprodol, chlorphenesin, chlorzoxazone, alprazolam, bromazepam, chlordiazepoxide, clorazepate, diazepam, flunitriazepam, lorazepam, medazepam, midazolam, oxazepam, prazepam, triazolam, temazepam, and botulinum toxin. In certain embodiments, any of the drugs useful for treating neuropathic pain may be coadminstered with a prodrug of a $GABA_B$ agonist for treating musculskeletal pain.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating low back pain in combination with a therapy or another therapeutic agent known or believed to be effective in treating low back pain. Examples of drugs useful for treating low back pain and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include NSAIDs such as aspirin, naproxen, and ibuprofen; anticonvulsants; antidepressants such as amitriptyline and desipramine; and opioids such as codeine, oxycodone, hydrocodone, and morphine. In certain embodiments, any of the drugs useful for treating neuropathic pain may be coadministered with a prodrug of a $GABA_B$ agonist for treating low back pain. Therapies for low back pain and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include the use of cold and hot compresses, bed rest, exercise, spinal manipulation, acupuncture, biofeedback, interventional therapy, traction, transcutaneous electrical nerve stimulation, ultrasound, vertebroplasty, kyphoplasty, discectomy, foraminotomy, intradiscal electrothermal therapy, nucleoplasty, radiofrequency lesioning, spinal fusion, and spinal laminectomy.

In certain embodiments, crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate may be administered to a patient for treating low back pain in combination with a therapy or other therapeutic agent for treating muscle spasms, for example muscle spasms associated with low back pain, such as muscle relaxants. Examples of drugs useful as muscle relaxants for treating muscle spasms and which may be administered in conjunction with crystalline (3R)-4-{[(1S)-2-methyl-1-(2-methylpropanoyloxy)propoxy]carbonylamino}-3-(4-chlorophenyl)butanoic acid anhydrate and/or crystalline (3R)-4-{[(1S)-2-methyl-1-(2-methylpropanoyloxy)propoxy]carbonylamino}-3-(4-chlorophenyl)butanoic acid hemihydrate include baclofen, carisoprodol, chlorzoxazone, cyclobenzaprine, diazepam, metaxalone, methocarbamol, orphenadrine, and tizanidine.

EXAMPLES

The following examples describe in detail the preparation, properties, and uses of crystalline (3R)-4-{[(1S)-2-methyl-1-(2-methylpropanoyloxy)propoxy]carbonylamino}-3-(4-chlorophenyl)butanoic acid anhydrate and crystalline (3R)-4-{[(1S)-2-methyl-1-(2-methylpropanoyloxy)propoxy]carbonylamino}-3-(4-chlorophenyl)butanoic acid hemihydrate. It will be apparent to those skilled in the art that many modifications, both to materials and methods, may be practiced without departing from the scope of the disclosure.

Example 1

Synthesis of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid; and Separation by Crystallization To 3 moles of 2-methyl-1-(methylthiocarbonyloxy)propyl isobutyrate is added N-hydroxysuccinimide and a mixture of dichloromethane and peracetic acid. The mixture is cooled to 15° C. during the addition of the mixture of dichloromethane and peracetic acid. 1-((2,5-dioxopyrrolidin-1-yl-oxycarbonyloxy)-2-methylpropyl)-2-methylpropanoate (3) is extracted from the final solution via cold water extraction. To the extracted compound (3) a 1:1 mixture of isopropyl alcohol:hexane is added and the mixture cooled in a dry-ice bath. Compound (3) crystallizes in this reaction mixture. The product is collected by filtration and dried to afford 470 g (53%) of crystalline 1-((2,5-dioxopyrrolidin-1-yl-oxycarbonyloxy)-2-methylpropyl)-2-methylpropanoate (3).

To a 500 mL, round bottomed flask, is added 21.3 g (R)-baclofen (2) and 30.1 g compound (3). The two compounds are mixed and a mixture of 100 mL acetonitrile and 100 mL water is added at room temperature. The reaction is stirred at room temperature for 4 hours. The reaction mixture is diluted with 500 mL methyl tert-butyl ether, washed twice with 200 mL water, and washed once with 100 mL of brine. The methyl tert-butyl ether layer is dried to afford a mixture of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid.

To 40 g of the mixture of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid is added 800 mL of a 1:1 mixture of toluene:methylcyclohexane. (3R)-4-{[(1S)-2-methyl-1-(2-methylpropanoyloxy)propoxy]carbonylamino}-3-(4-chlorophenyl)butanoic acid (1) crystallizes in this reaction mixture to afford 13 g (65%) of crystalline compound (I). This crystallization reaction separates (3R)-4-{[(1S)-2-methyl-1-(2-methylpropanoyloxy)propoxy]carbonylamino}-3-(4-chlorophenyl)butanoic acid (1) from (3R)-4-{[(1R)-2-methyl-1-(2-methylpropanoyloxy)propoxy]carbonylamino}-3-(4-chlorophenyl)butanoic acid.

Example 2

Separation of (3R)-4-{[(1S)-2-methyl-1-(2-methylpropanoyloxy)propoxy]carbonylamino}-3-(4-chlorophenyl)butanoic acid (1) from (3R)-4-{[(1R)-2-methyl-1-(2-methylpropanoyloxy)propoxy]carbonylamino}-3-(4-chlorophenyl)butanoic acid by Crystallization From 3:1 Toluene:Methylcyclohexane A portion of the mixture of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid produced according to Example 1 is separated as follows: to 110 g of the mixture of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid is added 3.3 L of a 3:1 mixture of toluene:methylcyclohexane. (3R)-4-{[(1S)-2-methyl-1-(2-methylpropanoyloxy)propoxy]carbonylamino}-3-(4-chlorophenyl)butanoic acid (1) crystallizes in this reaction mixture to afford 88 g (80%) of crystalline compound (I).

A second crystallization is performed as follows: to 20 g of the mixture of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid produced according to Example 1 is added 400 mL of a 3:1 mixture of toluene:methylcyclohexane. (3R)-4-{[(1S)-2-methyl-1-(2-methylpropanoyloxy)propoxy]carbonylamino}-3-(4-chlorophenyl)butanoic acid (1) crystallizes in this reaction mixture to afford 5 g (25%) of crystalline compound (1).

From 1.5:1 Methanol:Water

A portion of the mixture of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid produced according to Example 1 is separated as follows: 40 g of the mixture of (3R)-4-{[(1S)-2-methyl-1-(2-methylpropanoyloxy)propoxy]carbonylamino}-3-(4-chlorophenyl)butanoic acid (1) and (3R)-4-{[(1R)-2-methyl-1-(2-methylpropanoyloxy)propoxy]carbonylamino}-3-(4-chlorophenyl)butanoic acid is dissolved in a mixture of 150 mL methanol and 100 mL water. The mixture is heated to 60° C. and then cooled to room temperature. The heating and cooling procedure is performed 5 times in succession to yield 6 g (30%) of crystalline (3R)-4-{[(1S)-2-methyl-1-(2-methylpropanoyloxy)propoxy]carbonylamino}-3-(4-chlorophenyl)butanoic acid (1).

Example 3

Crystallization of (3R)-4-{[(1S)-2-methyl-1-(2-methylpropanoyloxy)propoxy]carbonylamino}-3-(4-chlorophenyl)butanoic acid hemihydrate (1b)

A 2,500 L reaction vessel was charged with 313 L of methyl tert-butyl ether (MTBE) and 224 L of water, to which was added 100 kg of (R)-baclofen and 134 kg of 1-((2,5-dioxopyrrolidin-1-yl-oxycarbonyloxy)-2-methylpropyl)-2-methylpropanoate (3) at 20° C. The charging lock and the reactor walls were each rinsed with 67 liters of MTBE. The reaction mixture was heated to 45° C. and stirred for 6.25 hours. The reaction mixture was then cooled to 20° C., the aqueous phase was separated and discarded. The organic phase was washed with 224 kg of 1N hydrochloric acid, followed by two washes with 224 kg of water each. The product-containing organic phase was filtered through a charcoal cartridge. The reactor and lines were rinsed with 137 liters of MTBE, which was also filtered through the charcoal filter and combined with the previous filtrate. The combined organic phase was washed once more with 224 kg of water.

To the filtrate was added 277 L of methylcyclohexane, and 67 L of MTBE followed by an additional 768 L of methylcyclohexane. The resulting mixture was heated to 50° C. to dissolve all solids. The solution was then cooled to 35° C. within one hour and seeded with 0.25 kg of (3R)-4-{[(1S)-2-methyl-1-(2-methylpropanoyloxy)propoxy]carbonylamino}-3-(4-chlorophenyl)butanoic acid hemihydrate (1b). The resulting mixture was cooled to 5° C. over a period of ten hours. Crystalline (3R)-4-{[(1S)-2-methyl-1-(2-methylpropanoyloxy)propoxy]carbonylamino}-3-(4-chlorophenyl)butanoic acid hemihydrate (1b) was isolated via centrifugation, washed with a mixture of 34.4 kilograms of MTBE and 82.6 kg of methylcyclohexane, and dried at a temperature between 45° C. to 75° C. using a vacuum of 25 to 50 mbar. This resulted in 51.75 kg of crystalline (3R)-4-{[(1S)-2-methyl-1-(2-methylpropanoyloxy)propoxy]carbonylamino}-3-(4-chlorophenyl)butanoic acid hemihydrate (1b).

Example 4

Crystallization of (3R)-4-{[(1S)-2-methyl-1-(2-methylpropanoyloxy)propoxy]carbonylamino}-3-(4-chlorophenyl)butanoic acid anhydrate (1a)

To a 2,500 L reactor was added 51.1 kg of crystalline (3R)-4-{[(1S)-2-methyl-1-(2-methylpropanoyloxy)propoxy]carbonylamino}-3-(4-chlorophenyl)butanoic acid hemihydrate (1b) and 104.4 kg of acetone, at 35° C. To this mixture was added 247.15 kg of hexane and the mixture was heated to 50° C. and stirred for 10 minutes at this temperature. The temperature was then reduced to 45° C. Thereafter 98 kg of hexane was added, followed by 50 g of (3R)-4-{[(1S)-2-methyl-1-(2-methylpropanoyloxy)propoxy]carbonylamino}-3-(4-chlorophenyl)butanoic acid anhydrate seed crystals. A further 488.4 kg of hexane was added at 45° C. and the mixture was cooled to 0° C. within 2.5 hours. Crystalline (3R)-4-{[(1S)-2-methyl-1-(2-methylpropanoyloxy)propoxy]carbonylamino}-3-(4-chlorophenyl)butanoic acid anhydrate was isolated via centrifugation, washed with a mixture of 168.1 kg of hexane in 23 L of acetone, and dried at 50° C. using a vacuum of 22-49 mbar for 15 hours. This resulted in 45.15 kg of (3R)-4-{[(1S)-2-methyl-1-(2-methylpropanoyloxy)propoxy]carbonylamino}-3-(4-chlorophenyl)butanoic acid anhydrate.

Example 5

Differential Scanning Calorimetry of Crystalline (3R)-4-{[(1S)-2-methyl-1-(2-methylpropanoyloxy)propoxy]carbonylamino}-3-(4-chlorophenyl)butanoic acid hemihydrate (1b)

Differential scanning calorimetry was performed using a Perkin Elmer DSC-7 instrument. DSC on the hemihydrate was carried out in a gold sample pan sealed in air. Heating occurred at a rate of 20 K/min over a temperature range of 0° C.-150° C.

Crystalline (3R)-4-{[(1S)-2-methyl-1-(2-methylpropanoyloxy)propoxy]carbonylamino}-3-(4-chlorophenyl)butanoic acid hemihydrate prepared according to Example 3 exhibited two distinct melt transitions. The first melt transition occurred from about 70° C. to about 110° C., with a peak maximum at about 100° C. and a ΔH of about 58.3 J/g. The second melt transition occurred from about 110° C. to about 125° C., with a peak maximum at about 115° C. and a ΔH of about 39.1 J/g.

The lower melting peak near 100° C. corresponds to melting of crystalline (3R)-4-{[(1S)-2-methyl-1-(2-methylpropanoyloxy)propoxy]carbonylamino}-3-(4-chlorophenyl)butanoic acid hemihydrate, while the second melting peak near 115° C. corresponds to the melting of crystalline (3R)-4-{[(1S)-2-methyl-1-(2-methylpropanoyloxy)propoxy]carbonylamino}-3-(4-chlorophenyl)butanoic acid anhydrate, which exhibits a depressed melting point in this case, because of the presence of water released from the hemihydrate.

Example 6

Thermogravimetric Analysis of Crystalline (3R)-4-{[(1S)-2-methyl-1-(2-methylpropanoyloxy)propoxy]carbonylamino}-3-(4-chlorophenyl)butanoic acid hemihydrate (1b)

Thermogravimetric measurements were carried out with a Netzsch Thermo-Microbalance TG 209 coupled to a Bruker FTIR Spectrometer Vector 22. The sample was contained in sample pans with a pinhole, under a $N_2$ atmosphere. The heating rate was set at 10 K/min.

Crystalline (3R)-4-{[(1S)-2-methyl-1-(2-methylpropanoyloxy)propoxy]carbonylamino}-3-(4-chlorophenyl)butanoic acid hemihydrate prepared according to Example 3 exhibited a weight loss of about 2.1% up to 170° C. when heated at a scan rate of 10 K/min. This weight loss, which occurred predominantly between 80° C. and 130° C., is attributable to water.

Under the conditions used for TG-FTIR thermal decomposition began slowly at about 170° C. and increased strongly above 190° C.

Example 7

X-Ray Powder Diffraction Analysis of Crystalline (3R)-4-{[(1S)-2-methyl-1-(2-methylpropanoyloxy)propoxy]carbonylamino}-3-(4-chlorophenyl)butanoic acid hemihydrate (1b)

X-ray powder diffraction analyses were performed using a Bruker D8 Advance powder X-ray diffractometer using CuKα radiation. 2θ values are accurate within an error of ±0.1-0.2°. The tube voltage and amperage were set to 35 kV and 45 mA, respectively. The step size was set at 0.017° (2θ), the step time was set at 105±5 sec, and the scanning range was 2°-50° (2θ). The samples were rotated. Differential radiation was detected by a VANTEC1 detector having an opening angle of 3° and a total number of active channels of 360±10. The y-axis (counts or CPS) of the diffractogram depicted in FIG. 1 does not show the total intensity(/sec) but rather the value intensity/number of active detector channels(/sec). Sample holders were silicon single crystal and sample dimensions were a depth/diameter: 0.1 mm/~12 mm.

The X-ray powder diffractogram for crystalline (3R)-4-{[(1S)-2-methyl-1-(2-methylpropanoyloxy)propoxy]carbonylamino}-3-(4-chlorophenyl)butanoic acid hemihydrate prepared according to Example 3 is shown in FIG. 1. The characteristic scattering angles for the same crystalline preparation shown in FIG. 1 are presented in Table 1.

TABLE 1

| XRPD Scattering Angles. 2θ (deg) |
|---|
| 4.04° ± 0.2° |
| 6.47° ± 0.2° |
| 7.97° ± 0.2° |
| 9.46° ± 0.2° |
| 10.10° ± 0.2° |
| 10.87° ± 0.2° |
| 12.88° ± 0.2° |
| 15.68° ± 0.2° |
| 16.72° ± 0.2° |
| 18.16° ± 0.2° |
| 18.91° ± 0.2° |
| 19.33° ± 0.2° |
| 19.96° ± 0.2° |
| 20.23° ± 0.2° |
| 20.62° ± 0.2° |
| 21.76° ± 0.2° |
| 22.42° ± 0.2° |
| 23.55° ± 0.2° |
| 24.02° ± 0.2° |
| 25.13° ± 0.2° |
| 25.61° ± 0.2° |
| 26.09° ± 0.2° |
| 28.07° ± 0.2° |
| 28.53° ± 0.2° |
| 29.87° ± 0.2° |
| 30.45° ± 0.2° |
| 30.74° ± 0.2° |
| 31.52° ± 0.2° |
| 32.60° ± 0.2° |
| 35.94° ± 0.2° |
| 36.63° ± 0.2° |

Example 8

Raman Spectroscopy Analysis of Crystalline (3R)-4-{[(1S)-2-methyl-1-(2-methylpropanoyloxy)propoxy]carbonylamino}-3-(4-chlorophenyl)butanoic acid hemihydrate (1b)

FT-Raman spectra were recorded on a Bruker RFS 100 FT-Raman system with a near infrared Nd:YAG laser operating at 1064 nm and a liquid nitrogen-cooled germanium detector. A total of 64 scans with a resolution of 2 $cm^{-1}$ were accumulated in the range from 3500 to 50 $cm^{-1}$. In general, 100 mW laser power was used. Dispersive Raman spectra were taken on a Renishaw RM 1000 System using a 20× long working distance objective lens in conjunction with a diode laser operating at 785 nm. The measurements were carried out over the range 2000 $cm^{-1}$ to 100 $cm^{-1}$.

The Raman spectrum for crystalline (3R)-4-{[(1S)-2-methyl-1-(2-methylpropanoyloxy)propoxy]carbonylamino}-3-(4-chlorophenyl)butanoic acid hemihydrate prepared according to Example 3 is shown in FIG. 2.

The most prominent bands were found at 1744 $cm^{-1}$, 1600 $cm^{-1}$, 1453 $cm^{-1}$, 1290 $cm^{-1}$, 1238 $cm^{-1}$, 1201 $cm^{-1}$, 954 $cm^{-1}$, 872 $cm^{-1}$, 779 $cm^{-1}$, 635 $cm^{-1}$, 362 $cm^{-1}$, 315 $cm^{-1}$, 110 $cm^{-1}$, and 84 $cm^{-1}$. The band at 110 $cm^{-1}$ was the strongest Raman spectrum band displayed.

Example 9

Differential Scanning calorimetry of Crystalline (3R)-4-{[(1S)-2-methyl-1-(2-methylpropanoyloxy)propoxy]carbonylamino}-3-(4-chlorophenyl)butanoic acid anhydrate (1a)

Differential scanning calorimetry was performed using a Perkin Elmer DSC-7 instrument. DSC on the hemihydrate was carried out in a gold sample pan sealed under nitrogen. Heating occurred at a rate of 20K/min over a temperature range of 0° C.-150° C.

Crystalline (3R)-4-{[(1S)-2-methyl-1-(2-methylpropanoyloxy)propoxy]carbonylamino}-3-(4-chlorophenyl)butanoic acid anhydrate prepared according to the methods of the present disclosure exhibited a single melt transition from about 120° C. to about 145° C., with a peak maximum at about 131° C. and a ΔH of about 92.6 J/g.

Example 10

Thermogravimetric Analysis of Crystalline (3R)-4-{[(1S)-2-methyl-1-(2-methylpropanoyloxy)propoxy]carbonylamino}-3-(4-chlorophenyl)butanoic acid anhydrate (1a)

Thermogravimetric measurements were carried out with a Netzsch Thermo-Microbalance TG 209 coupled to a Bruker FTIR Spectrometer Vector 22. The sample was contained in sample pans with a pinhole, under a $N_2$ atmosphere. The heating rate was set at 10 K/min.

Crystalline (3R)-4-{[(1S)-2-methyl-1-(2-methylpropanoyloxy)propoxy]carbonylamino}-3-(4-chlorophenyl)butanoic acid anhydrate prepared according to the methods of the present disclosure showed very little weight loss up to 180° C. when heated at a scan rate of 10 K/min.

Under the conditions used for TG-FTIR, thermal decomposition began slowly at about 170° C. and increased strongly above 190° C.

Example 11

X-Ray Powder Diffraction Analysis of Crystalline (3R)-4-{[(1S)-2-methyl-1-(2-methylpropanoyloxy)propoxy]carbonylamino}-3-(4-chlorophenyl)butanoic acid anhydrate (1a)

X-ray powder diffraction analyses were performed using a Bruker D8 Advance powder X-ray diffractometer using CuKα radiation. 2θ values are accurate within an error of ±0.1-0.2°. The tube voltage and amperage were set to 35 kV and 45 mA, respectively. The step size was set at 0.017° (2θ), the step time was set at 105±5 sec, and the scanning range was 2°-50° (2θ). The samples were rotated. Differential radiation was detected by a VANTEC1 detector having an opening angle of 3° and a total number of active channels of 360±10. The y-axis (counts or CPS) of the diffractogram depicted in FIG. 3 does not show the total intensity(/sec) but rather the value intensity/number of active detector channels(/sec). Sample holders were silicon single crystal and sample dimensions were a depth/diameter: 0.1 mm/~12 mm.

The X-ray powder diffractogram for crystalline (3R)-4-{[(1S)-2-methyl-1-(2-methylpropanoyloxy)propoxy]carbonylamino}-3-(4-chlorophenyl)butanoic acid anhydrate prepared according to the methods of the present disclosure is shown in FIG. 3. The characteristic scattering angles for the same crystalline preparation shown in FIG. 3 are presented in Table 2.

TABLE 2

| XRPD Scattering Angles. θ2θ (deg) |
| --- |
| 4.33° ± 0.2° |
| 4.76° ± 0.2° |
| 5.83° ± 0.2° |
| 6.93° ± 0.2° |
| 9.07° ± 0.2° |
| 9.46° ± 0.2° |
| 10.54° ± 0.2° |
| 11.06° ± 0.2° |
| 11.61° ± 0.2° |
| 12.94° ± 0.2° |
| 15.25° ± 0.2° |
| 16.55° ± 0.2° |
| 17.46° ± 0.2° |
| 17.84° ± 0.2° |
| 18.01° ± 0.2° |
| 18.41° ± 0.2° |
| 18.69° ± 0.2° |
| 18.93° ± 0.2° |
| 19.36° ± 0.2° |
| 20.01° ± 0.2° |
| 20.46° ± 0.2° |
| 21.26° ± 0.2° |
| 21.75° ± 0.2° |
| 22.19° ± 0.2° |
| 22.56° ± 0.2° |
| 23.35° ± 0.2° |
| 23.85° ± 0.2° |
| 24.84° ± 0.2° |
| 25.96° ± 0.2° |
| 26.78° ± 0.2° |
| 27.29° ± 0.2° |
| 28.69° ± 0.2° |
| 29.39° ± 0.2° |
| 31.22° ± 0.2° |
| 32.35° ± 0.2° |
| 33.47° ± 0.2° |
| 34.62° ± 0.2° |
| 36.08° ± 0.2° |

Example 12

Raman Spectroscopy Analysis of Crystalline (3R)-4-{[(1S)-2-methyl-1-(2-methylpropanoyloxy)propoxy]carbonylamino}-3-(4-chlorophenyl)butanoic acid anhydrate (1a)

FT-Raman spectra were recorded on a Bruker RFS 100 FT-Raman system with a near infrared Nd:YAG laser operating at 1064 nm and a liquid nitrogen-cooled germanium detector. A total of 64 scans with a resolution of 2 $cm^{-1}$ were accumulated in the range from 3500 to 50 $cm^{-1}$. In general, 100 mW laser power was used. Dispersive Raman spectra were taken on a Renishaw RM 1000 System using a 20× long working distance objective lens in conjunction with a diode laser operating at 785 nm. The measurements were carried out over the range 2000 $cm^{-1}$ to 100 $cm^{-1}$.

The Raman spectrum for crystalline (3R)-4-{[(1S)-2-methyl-1-(2-methylpropanoyloxy)propoxy]carbonylamino}-3-(4-chlorophenyl)butanoic acid anhydrate prepared according to the methods of the present disclosure is shown in FIG. 4.

The most prominent bands were found at 1747 $cm^{-1}$, 1599 $cm^{-1}$, 1447 $cm^{-1}$, 1412 $cm^{-1}$, 1335 $cm^{-1}$, 1203 $cm^{-1}$, 1092 $cm^{-1}$, 954 $cm^{-1}$, 868 $cm^{-1}$, 798 $cm^{-1}$, 637 $cm^{-1}$, 401 $cm^{-1}$, 348 $cm^{-1}$, 317 $cm^{-1}$, 244 $cm^{-1}$, 119 $cm^{-1}$, and 85 $cm^{-1}$. The band at 119 $cm^{-1}$ was the strongest Raman spectrum band displayed.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. Crystalline (3R)-4-{[(1S)-2-methyl-1-(2-methylpropanoyloxy)propoxy]carbonylamino}-3-(4-chlorophenyl)butanoic acid hemihydrate, which exhibits characteristic scattering angles (2θ) at least at 4.04°±0.2°, 6.47°±0.2°, 15.68°±0.2°, 18.91°±0.2° and 22.42°±0.2° in an X-ray powder diffractogram measured using Cu—K$_\alpha$ radiation.

2. The crystalline (3R)-4-{[(1S)-2-methyl-1-(2-methylpropanoyloxy)propoxy]carbonylamino}-3-(4-chlorophenyl) butanoic acid hemihydrate of claim 1, comprising characteristic scattering angles (2θ) at least at 9.46°±0.2°, 10.10°±0.2°, 10.87°±0.2°, 12.88°±0.2°, 19.96°±0.2°, 20.23°±0.2°, 28.07°±0.2° and 28.53°±0.2° in an X-ray powder diffractogram measured using Cu—K$_\alpha$ radiation.

3. The crystalline (3R)-4-{[(1S)-2-methyl-1-(2-methylpropanoyloxy)propoxy]carbonylamino}-3-(4-chlorophenyl) butanoic acid hemihydrate of claim 1, comprising characteristic scattering angles (2θ) at least at 7.97°±0.2°, 9.46°±0.2°, 10.10°±0.2°, 10.87°±0.2°, 12.88°±0.2°, 16.72°±0.2°, 18.16°±0.2°, 19.33°±0.2°, 19.96°±0.2°, 20.23°±0.2°, 20.62°±0.2°, 21.76°±0.2°, 23.55°±0.2°, 24.02°±0.2°, 25.13°±0.2°, 25.61°±0.2°, 26.09°±0.2°, 28.07°±0.2°, 28.53°±0.2°, 29.87°±0.2°, 30.45°±0.2°, 30.74°±0.2°, 31.52°±0.2°, 32.60°±0.2°, 35.94°±0.2° and 36.63°±0.2° in an X-ray powder diffractogram measured using Cu—K$_\alpha$ radiation.

4. The crystalline (3R)-4-{[(1S)-2-methyl-1-(2-methylpropanoyloxy)propoxy]carbonylamino}-3-(4-chlorophenyl) butanoic acid hemihydrate of claim 1, comprising the characteristic scattering angles (2θ) in an X-ray powder diffractogram measured using Cu—K$_\alpha$ radiation shown in FIG. 1.

5. The crystalline (3R)-4-{[(1S)-2-methyl-1-(2-methylpropanoyloxy)propoxy]carbonylamino}-3-(4-chlorophenyl) butanoic acid hemihydrate of claim 1, comprising from about 2 wt % water to about 3 wt % water.

6. The crystalline (3R)-4-{[(1S)-2-methyl-1-(2-methylpropanoyloxy)propoxy]carbonylamino}-3-(4-chlorophenyl) butanoic acid hemihydrate of claim 1, which exhibits a first phase transition at a temperature of from about 90° C. to about 110° C., and a second phase transition at a temperature of from about 105° C. to about 125° C. using differential scanning calorimetry at a heating rate of 20 K/min.

7. The crystalline (3R)-4-{[(1S)-2-methyl-1-(2-methylpropanoyloxy)propoxy]carbonylamino}-3-(4-chlorophenyl) butanoic acid hemihydrate of claim 6, which loses about 2.1% of its total weight in the first phase transition.

8. The crystalline (3R)-4-{[(1S)-2-methyl-1-(2-methylpropanoyloxy)propoxy]carbonylamino}-3-(4-chlorophenyl) butanoic acid hemihydrate of claim 1, wherein the first phase transition occurs at 100° C., and the second phase transition occurs at 115° C.

9. A pharmaceutical composition comprising the crystalline (3R)-4-{[(1S)-2-methyl-1-(2-methylpropanoyloxy)propoxy]carbonylamino}-3-(4-chlorophenyl)butanoic acid hemihydrate of claim 1 and a pharmaceutically acceptable vehicle.

10. The pharmaceutical composition of claim 9, wherein the pharmaceutical composition is a sustained release oral dosage formulation.

11. A method of treating a disease or disorder in a patient comprising administering to a patient in need of such treatment a therapeutically effective amount of the pharmaceutical composition of claim 9, wherein the disease or disorder is selected from spasticity, gastroesophageal reflux disease, emesis, cough, substance addiction and abuse, neuropathic pain and musculoskeletal pain.

12. The method of claim 11, wherein the pharmaceutical composition is a sustained release oral dosage formulation.

13. A kit comprising the pharmaceutical composition of claim 9 and instructions for administering the pharmaceutical composition to a patient in need thereof for treating a disease or disorder selected from spasticity, gastroesophageal reflux disease, emesis, cough, substance addiction and abuse, neuropathic pain and musculoskeletal pain.

14. A method of making crystalline (3R)-4-{[(1S)-2-methyl-1-(2-methylpropanoyloxy)propoxy]carbonylamino}-3-(4-chlorophenyl)butanoic acid anhydrate, comprising:
    a) forming a solution of diastereomers comprising (i) (3R)-4-{[(1S)-2-methyl-1-(2-methylpropanoyloxy)propoxy]carbonylamino}-3-(4-chlorophenyl)butanoic acid and (ii) (3R)-4-{[(1R)-2-methyl-1-(2-methylpropanoyloxy)propoxy]carbonylamino}-3-(4-chlorophenyl)butanoic acid;
    b) selectively crystallizing the (3R)-4-{[(1S)-2-methyl-1-(2-methylpropanoyloxy)propoxy]carbonylamino}-3-(4-chlorophenyl)butanoic acid diastereomer as a hemihydrate; and
    c) separating the crystalline (3R)-4-{[(1S)-2-methyl-1-(2-methylpropanoyloxy)propoxy]carbonylamino}-3-(4-chlorophenyl)butanoic acid hemihydrate diastereomer from the solution.

15. The method of claim 14, comprising converting the crystalline (3R)-4-{[(1S)-2-methyl-1-(2-methylpropanoyloxy)propoxy]carbonylamino}-3-(4-chlorophenyl)butanoic acid hemihydrate into crystalline (3R)-4-{[(1S)-2-methyl-1-(2-methylpropanoyloxy)propoxy]carbonylamino}-3-(4-chlorophenyl)butanoic acid anhydrate.

16. The method of claim 14, wherein the diastereomers are in aqueous solution.

17. The method of claim 14, wherein the solution comprises solvent in an amount ranging from about 20 v/v % to about 50 v/v % and water in an amount ranging from about 50 v/v % to about 80 v/v %.

18. The method of claim 17, wherein the solvent is selected from methyl tert-butyl ether, acetonitrile, toluene, chlorobenzene, methylcyclohexane, heptane, methanol, ethanol, diethyl ether, tetrahydrofuran, tert-amyl methyl ether and combinations of the foregoing.

19. The method of claim 15, wherein the converting comprises drying the crystalline (3R)-4-{[(1S)-2-methyl-1-(2-methylpropanoyloxy)propoxy]carbonylamino}-3-(4-chlorophenyl)butanoic acid hemihydrate.

20. The method of claim 15, wherein the converting comprises recrystallizing the crystalline (3R)-4-{[(1S)-2-methyl-1-(2-methylpropanoyloxy)propoxy]carbonylamino}-3-(4-chlorophenyl)butanoic acid hemihydrate.

* * * * *